US008207347B2

(12) United States Patent
Khanzhin et al.

(10) Patent No.: US 8,207,347 B2
(45) Date of Patent: Jun. 26, 2012

(54) PYRIDONE DERIVATIVES AS NK3 ANTAGONISTS

(75) Inventors: Nikolay Khanzhin, Humlebaek (DK); Søren Møller Nielsen, Hillerød (DK); Karsten Juhl, Greve (DK); Lars Kyhn Rasmussen, København S (DK)

(73) Assignee: H. Lundbeck A/S, Valby (DK)

( * ) Notice: Subject to any disclaimer, the term of this patent is extended or adjusted under 35 U.S.C. 154(b) by 70 days.

(21) Appl. No.: 12/967,414

(22) Filed: Dec. 14, 2010

(65) Prior Publication Data

US 2011/0144164 A1    Jun. 16, 2011

Related U.S. Application Data

(60) Provisional application No. 61/286,442, filed on Dec. 15, 2009.

(30) Foreign Application Priority Data

Dec. 15, 2009  (DK) .................................. 2009 01320

(51) Int. Cl.
*A61K 31/44* (2006.01)
*C07D 211/72* (2006.01)

(52) U.S. Cl. ........................................ 546/290; 514/345

(58) Field of Classification Search .................. None
See application file for complete search history.

(56) References Cited

U.S. PATENT DOCUMENTS

| 2002/0091265 | A1 | 7/2002 | Bos et al. |
| 2006/0281746 | A1 | 12/2006 | Kehler et al. |
| 2009/0143402 | A1 | 6/2009 | Simonsen et al. |
| 2011/0130407 | A1 | 6/2011 | Khanzhin et al. |
| 2011/0130420 | A1 | 6/2011 | Khanzhin et al. |

FOREIGN PATENT DOCUMENTS

| WO | 9532948 A1 | 12/1995 |
| WO | 2005014575 A1 | 2/2005 |
| WO | 2006050991 A1 | 5/2006 |
| WO | 2006050992 A1 | 5/2006 |
| WO | 2006130080 A2 | 12/2006 |
| WO | 2008131779 A1 | 11/2008 |
| WO | 2009130240 A1 | 10/2009 |
| WO | 2009/156339 A1 | 12/2009 |
| WO | 2010/028655 A1 | 3/2010 |
| WO | 2010/045948 A1 | 4/2010 |
| WO | 2011/110183 A1 | 9/2011 |

OTHER PUBLICATIONS

Weix, D. J. and Ellman, A. E. 2005, (RS)-(+)-2-Methyl-2-Propanesulfinamide [tert-Butylsulfinamide] Organic Syntheses 82 157.
Giardina: Guiseppe A. M. et al., 1997. Discovery of a Novel Class of Selective Non-Peptide Antagonists for the Human Neurokinin-3 Reeceptor. 1. Identification of the 4-Quinolinecarboxamide Framework, Journal of Medicinal Chemistry, vol. (40) No. 12, p. 1794-1807.
Giardina, G.A.M. et al., 1999. Replacement of the quinoline system in 2-phenyl-4-quinolinecarboxamide NK-3 receptor antagonists, Il Farmaco, 54, 364-374.
Albert, J. S., 2004, Neurokinin antagonists and their potential role in treating depression and other stress disorders, Expert Opin. Ther. Patents, 14(10):1421-1433.
Amato J. S. et al., 2005, Synthesis of 1-tert-Butyl-4-chloropiperidine: Generation of an N-tert-Butyl Group by the Reaction of a Dimethyliminium Salt with Methylmagnesium Chloride, J.Org.Chem., 70:1930-1933.
Berge S. M., et al., 1977, Pharmaceutical Salts, Journal of Pharmaceutical Sciences, 66(1):1-19.
Cogan D. A., et al., 1999, Asymetric Synthesis of Chiral Amines by Highly Diastereoselective 1,2-Additions of Organometallic Reagents to N-tert-Butanesulfinyl Imines, Tetrahedron, 55:8883-8904.
Dai Q., et al., 2005, Efficient Rhodium-Catalyzed Asymmetric Hydrogenation for the Synthesis of a New Class of N-Aryl beta-Amino Acid Derivatives, Org. Lett., 7(23):5343-5345.
Daoui, S., et al., 1998, Involvement of Tachykinin NK3 Receptors in Citric Acid-induced Cough and Bronchial Responses in Guinea Pigs, Am.J.Respir.Crit.Care Med., 158:42-48.
Evangelista, S., 2005, Talnetant, Curr.Opion.Invest.Drug, 6:717-721.
Fioramonti, J., et al., 2003, Intestinal anti-nociceptive behaviour of NK3 receptor antagonism in conscious rats: evidence to support a peripheral mechanism of action, Neurogastroenterol.Motil.,15:363-369.
Glossop, S. C., 2007, A Microwave-Assisted Alternative Synthesis of 8-Amino-2-methyl-3,4-dhydroisoquinolin-1-one, Synthesis, 7:0981-0983.
Kemel, M. L., et al., Mar. 1, 2002, Facilitation by Endogenous Tachykins of the NMDA-Evoked Release of Acetylcholine after Acute and Chronic Suppression of Dopaminergic Transmission in the Matrix of the Rat Striatum, J. Neurosci., 22(5):1929-1936.
Langlois X., et al., 2001, Use of the Beta-Imager for Rapid ex vivo Autoradiography Exemplified with Central Nervous System Penetrating Neurokinin 3 Antagonists, J.Pharm.Exp.Ther., 299:712-717.
Liu D., et al., 1999, Synthesis of Enantiomerically Pure N-tert-Butanesulfinyl Imines (tert-Butanesulfinimines) by the Direct Condensation of tert-Butanesulfinamide with Aldehydes and Ketones, J.Org.Chem., 64:1278-1284.
Maubach, K. A. et al., 1998, Tachykinins May Modify Spontaneous Epileptiform Activity in the Rat Entorhinal Cortex in Vitro by Activating Gabaergic Inhibitiion, Neurosci., 83:1047-1062.
Mazelin, L. et al., 1998, Comparative Effects of Nonppeptide Tachykinin Receptor Antagonists on Experimental Gut Inflammation in Rats and Guinea-Pigs, Life Sci., 63(4):293-304.
Meltzer H. Y., et al, 2004, Placebo-Controlled Evaluation of Four Novel Compounds for the Treatment of Schizophrenia and Schizoaffective Disorder, Am.J.Psychiatry, 161:975-984.

(Continued)

*Primary Examiner* — Janet L. Andres
*Assistant Examiner* — Heidi Reese
(74) *Attorney, Agent, or Firm* — Stephen G. Kalinchak; Mary Catherine Di Nunzio; Kitae Lim

(57) ABSTRACT

The present invention relates to compounds useful in therapy, in particular in the treatment of psychosis, to compositions comprising said compounds, and to methods of treating diseases comprising the administration of said compounds.

20 Claims, No Drawings

OTHER PUBLICATIONS

Modi, A. R., et al., Oct. 1979, Isoquinolones: Part IV-Synthesis of 3-Methyl, 3-Formyl & Other 3-Substituted N-Arylisoquinolones, Indian J. Chem. 18B:304-306.

Spooren, W., Riemer, C., Meltzer, H., Dec. 2005, NK3 receptor antagonists: the next generation of antipsychotics? Nature Reviews, 4:967-975.

Sugaya T., et al. Jan. 1994, Synthesis of a 6H-Pyrazolo[4,5 1-de]acridin-6-one Derivative: A Useful Intermediate of anti-tumour Agents, Synthesis, 73-76.

Ukrainets, I. V., et al., Feb. 2006, 4-Hydroxyquinolones-2. 91*.Synthesis and Properties of Ethyl 1-R-4-Hydroxy-6-Methyl-2-Oxo-Dihydropyridine-5-Carboxylates. Chemistry of Heterocyclic Compounds, 42(2):191-196.

Yip J., Chahl, L. A., 1997, Localization of Fos-like immunoreactivity induced by the NK3 tachykinin receptor agonist, senktide, in the guinea-pig brain; Br.J.Phar., 122:715-722.

PYRIDONE DERIVATIVES AS NK3 ANTAGONISTS

CROSS-REFERENCE TO RELATED APPLICATION

The present application claims the benefit of priority under 35 U.S.C. §119(e) of U.S. Provisional Patent Application No. 61/286,442, filed Dec. 15, 2009, and claims the benefit of priority under 35 U.S.C. §119(a)-(d) of Danish Application No. PA200901320, filed Dec. 15, 2009. Each of these applications is hereby incorporated by reference in its entirety.

FIELD OF THE INVENTION

The present invention relates to compounds useful in therapy, in particular in the treatment of psychosis, to compositions comprising said compounds, and to methods of treating diseases comprising the administration of said compounds.

BACKGROUND OF THE INVENTION

The currently approved antipsychotic drugs share the common feature of reducing the dopamine signalling in the brain. This is achieved through either a dopamine D2 receptor antagonistic or partial agonistic effect. The first generation antipsychotics (also referred to as "typical") are often associated with extra-pyrimidal side effects wherefore the use of these agents have diminished. Second generation or "atypical" antipsychotics in addition to the D2 receptor affinity have affinity to the serotonin receptor 2A (5-$HT_{2A}$). Some atypical antipsychotics in addition have affinity for the 5-$HT_{2C}$, 5-$HT_6$, or 5-$HT_7$ receptors. Atypical antipsychotics give rise to fewer extra-pyrimidal side effects, but are still hampered by weight gain and $QT_C$ effects. Examples of atypicals are clozapine, olanzapine and risperidone.

More recently, neurokinin receptors have been suggested as targets for CNS diseases [Albert, *Expert Opin. Ther. Patents*, 14, 1421-1433, 2004]. Neurokinins (or tachykinins) are a family of neuropeptides, which include substance P(SP), neurokinin A (NKA), and neurokinin B (NKB). The biological effects of these substances are primarily effected through binding to and activation of the three neurokinin receptors NK1, NK2, and NK3. Although some cross reactivity probably exists, SP has the highest affinity and is believed to be the endogenous ligand for NK1, and likewise for NKA and NK2, and for NKB and NK3.

NK3 is primarily expressed centrally in regions including cortical regions, such as frontal, parietal and cingulated cortex; nuclei of the amygdale, such as the basal, central and lateral nuclei; the hippocampus; and mesencephalon structures, such as ventral tegmental area, substantia nigra pars compacta, and dorsal raphe nuclei [Spooren et al, *Nature Reviews*, 4, 967-975, 2005]. The NK3 receptor is expressed on dopaminergic neurons, and Spooren et al has suggested that the antipsychotic effects of NK3 antagonists are mediated by an inhibition of the dopamine tone, particularly at the D2 receptor combined with a reduction of the serotonergic tone, particularly at the 5-$HT_{2A}$ receptor.

Two structurally distinct NK3 antagonists, namely talnetant and osanetant, have been clinically tested for antipsychotic, and in particular antischizophrenic effects.

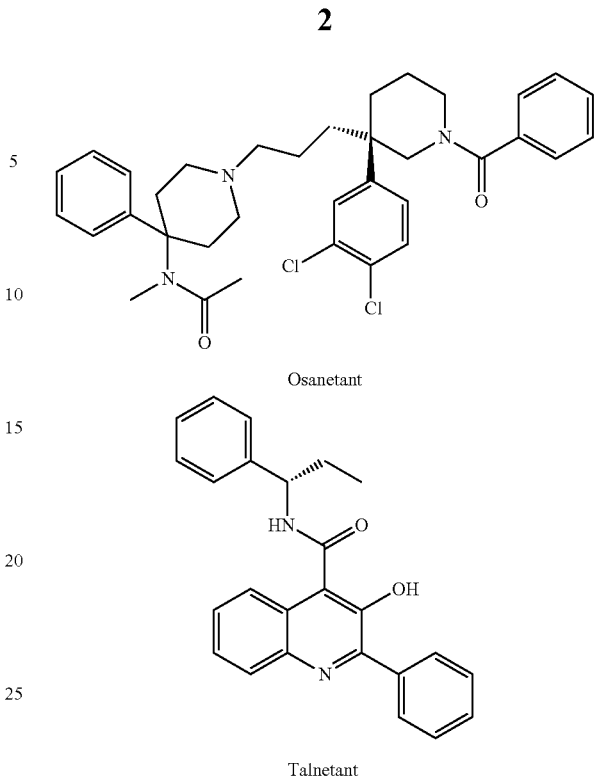

Osanetant

Talnetant

Osanetant proved superior to placebo in clinical trials, in particular on positive symptoms of psychosis, i.e. delusions, hallucinations and paranoia [*Am. J. Psychiatry*, 161, 2004, 975-984]. Similarly, talnetant has been shown in clinical trials to ameliorate the cognitive behaviour of schizophrenics [*Curr. Opion. Invest. Drug*, 6, 717-721, 2005]. Nevertheless, both compounds are hampered by poor pharmacokinetic and pharmacodynamic properties including poor solubility, poor bioavailability, relatively high clearance, and poor blood-brain barrier penetration [*Nature reviews*, 4, 967-975, 2005]. These results lend support to the notion that the NK3 receptor is a promising target for the treatment of e.g. psychosis, however emphasising the need for identifying compounds with adequate pharmacokinetic and pharmacodynamic properties.

WO95/32948 discloses a range of quinoline derivatives, including talnetant as NK3 antagonists.

More recently, WO 2006/130080 discloses compounds having the core structure

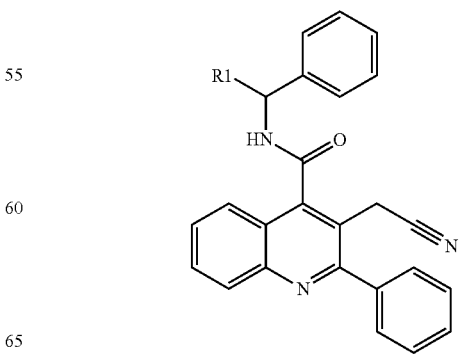

which compounds are said to be NK3 antagonists; and WO 2006/050991 and WO 2006/050992 disclose further quinolinecarboxamides derivatives, which derivatives are said to be NK3 antagonists.

WO 2005/014575 discloses compounds of the formula

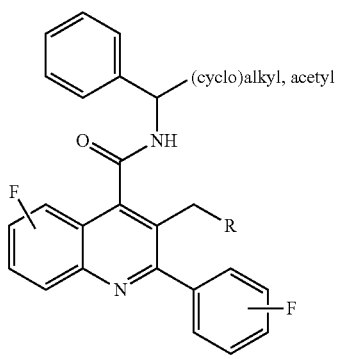

wherein R represents N-containing heterocycles, i.e. pyrazolyl, triazolyl and tetrazolyl.

WO 2008/131779 discloses that isoquinolone derivatives of the formula

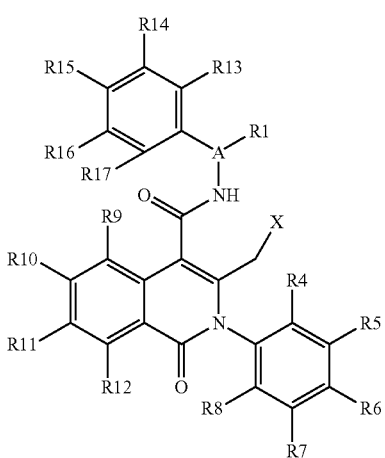

are NK3 antagonists.

Finally, *Chemistry of Heterocyclic Compounds, Vol.* 42 (2), 191-196, 2006 discloses a study on the synthesis of compounds with the following core structure

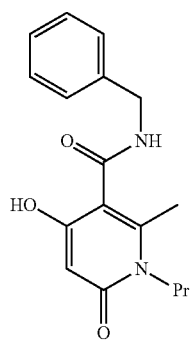

SUMMARY OF THE INVENTION

The present inventors have surprisingly found that certain pyridone derivatives are potent NK3 antagonists, which may as such be used in the treatment of e.g. psychosis. Accordingly, in one embodiment the invention relates to compounds of formula I

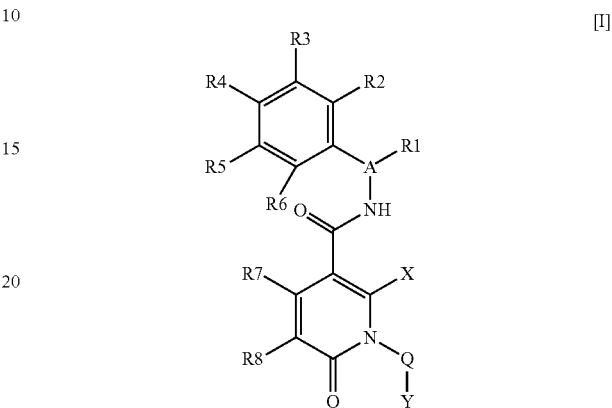

wherein A represents N, CH or $CR^1$;
each $R^1$ independently represents $C_{1-6}$alkyl, $C_{2-6}$alkenyl, $C_{2-6}$alkynyl;
X represents $C_{1-6}$alkyl;
Q represents a bond, —$CH_2$— or —NH—;
Y represents $C_{1-6}$ alkyl or Y represents heteroaryl with 5 ring atoms, wherein 1, 2 or 3 ring atoms are selected from O, N or S, or Y represents phenyl provided that Q is not —$CH_2$—, wherein said heteroaryl or phenyl may be substituted with one or more substituents selected from halogen, $C_{1-6}$alkyl, $C_{2-6}$alkenyl or $C_{2-6}$alkynyl;
each of $R^2$-$R^6$ independently represents hydrogen, $C_{1-6}$alkyl, $C_{2-6}$alkenyl, $C_{2-6}$alkynyl or halogen;
each of $R^7$-$R^8$ independently represents $C_{1-6}$alkyl, $C_{2-6}$alkenyl, $C_{2-6}$alkynyl, halogen, cyano, amine, wherein said $C_{1-6}$alkyl, $C_{2-6}$alkenyl or $C_{2-6}$alkynyl is optionally substituted with one or more halogens;
and pharmaceutically acceptable salts thereof;

In one embodiment, the invention relates to a compound of formula I and pharmaceutically acceptable salts thereof for use in therapy.

In one embodiment, the invention relates to a pharmaceutical composition comprising a compound of formula I and pharmaceutically acceptable salts thereof and one or more pharmaceutically acceptable carrier or excipient.

In one embodiment, the invention relates to a compound of formula I and pharmaceutically acceptable salts thereof for use in the treatment of a disease.

In one embodiment, the invention relates to the use of a compound of formula I and pharmaceutically acceptable salts thereof in the manufacture of a medicament.

In one embodiment, the invention relates to a method of treatment, said method comprising the administration of a therapeutically effective amount of a compound of formula I and pharmaceutically acceptable salts thereof to a patient in need thereof.

DEFINITIONS

In the present context, "alkyl" is intended to indicate a straight, branched and/or cyclic saturated hydrocarbon. In particular "$C_{1-6}$alkyl" is intended to indicate such hydrocarbon having 1, 2, 3, 4, 5, or 6 carbon atoms. Examples of $C_{1-6}$alkyl include methyl, ethyl, propyl, butyl, pentyl, hexyl, cyclopropyl, cyclobutyl, cyclopentyl, cyclohexyl, 2-methylpropyl, tert.-butyl, and cyclopropylmethyl.

In the present context, "alkenyl" is intended to indicate a non-aromatic, straight, branched and/or cyclic hydrocarbon comprising at least one carbon-carbon double bond. In particular "$C_{2-6}$alkenyl" is intended to indicate such hydrocarbon having 2, 3, 4, 5, or 6 carbon atoms. Examples of $C_{2-6}$alkenyl include ethenyl, 1-propenyl, 2-propenyl, 1-butenyl, 2-butenyl, 3-butenyl, and cyclohexenyl.

In the present context, "alkynyl" is intended to indicate a non-aromatic, straight, branched and/or cyclic hydrocarbon comprising at least one carbon-carbon triple bond and optionally also one or more carbon-carbon double bonds. In particular "$C_{2-6}$alkynyl" is intended to indicate such hydrocarbon having 2, 3, 4, 5, or 6 carbon atoms. Examples of $C_{2-6}$alkynyl include ethynyl, 1-propynyl, 2-propynyl, 1-butynyl, 2-butynyl, 3-butynyl and 5-but-1-en-3-ynyl.

In the present context "halogen" is intended to indicate members of the $7^{th}$ group of the periodic system, e.g. fluoro, chloro, bromo, and iodo.

In the present context, "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, pharmaceutically acceptable salts include pharmaceutically acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

DETAILED DESCRIPTION OF THE INVENTION

Accordingly, in one embodiment the invention relates to compounds of formula I

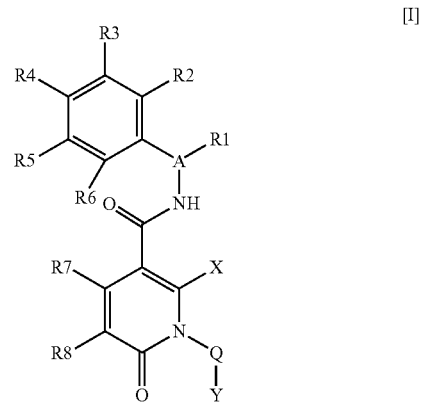

wherein A represents N, CH or $CR^1$;
each $R^1$ independently represents $C_{1-6}$alkyl, $C_{2-6}$alkenyl, $C_{2-6}$alkynyl;
X represents $C_{1-6}$alkyl;
Q represents a bond, —$CH_2$— or —NH—;
Y represents $C_{1-6}$ alkyl or Y represents heteroaryl with 5 ring atoms, wherein 1, 2 or 3 ring atoms are selected from O, N or S, or Y represents phenyl provided that Q is not —$CH_2$—, wherein said heteroaryl or phenyl may be substituted with one or more substituents selected from halogen, $C_{1-6}$alkyl, $C_{2-6}$alkenyl or $C_{2-6}$alkynyl;
each of $R^2$-$R^6$ independently represents hydrogen, $C_{1-6}$alkyl, $C_{2-6}$alkenyl, $C_{2-6}$alkynyl or halogen;
each of $R^7$-$R^8$ independently represents $C_{1-6}$alkyl, $C_{2-6}$alkenyl, $C_{2-6}$alkynyl, halogen, cyano, amine, wherein said $C_{1-6}$alkyl, $C_{2-6}$alkenyl or $C_{2-6}$alkynyl is optionally substituted with one or more halogens;
and pharmaceutically acceptable salts thereof;
In one embodiment, A represents CH.
In one embodiment, $R^1$ represents $C_{1-6}$alkyl, in a particular embodiment $R^1$ represents ethyl, 2-propyl, cyclopropyl, cyclobutyl, cyclopentyl or cyclohexyl.

In one embodiment, X represents methyl.

In one embodiment, Y is selected from $C_{1-6}$alkyl, phenyl or oxazole.

In one embodiment, Q is a bond and Y is selected from $C_{1-4}$alkyl or phenyl.

In one embodiment, Q is —NH— and Y represents $C_{1-4}$alkyl.

In one embodiment, each of $R^2$-$R^6$ independently represents hydrogen or halogen. In a particular embodiment, one or two of $R^2$-$R^6$ represents halogen.

In one embodiment, all of $R^2$-$R^6$ represent hydrogen.

In one embodiment, $R^7$ is selected from $C_{1-4}$alkyl or amine, wherein said $C_{1-4}$alkyl is optionally substituted with one or more halogens.

In one embodiment, $R^8$ represents halogen, cyano or ethynyl.

In one embodiment, $R^7$ represents $C_{1-6}$alkyl and $R^8$ represents halogen.

In one embodiment the invention relates to compounds of formula I'

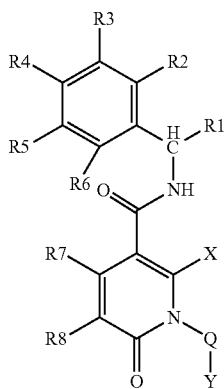

[I']

wherein each $R^1$ independently represents $C_{1-6}$alkyl, $C_{2-6}$alkenyl, $C_{2-6}$alkynyl;
X represents $C_{1-6}$alkyl;
Q represents a bond or —NH;
Y represents phenyl or $C_{1-6}$ alkyl; one or two of $R^2$-$R^6$ represents halogen;
$R^7$ represents $C_{1-4}$alkyl;
$R^8$ represents halogen, cyano or ethynyl;
and pharmaceutically acceptable salts thereof;

In one embodiment the compounds of the present invention are selected from the below list.

1a  5-Chloro-2,4-dimethyl-6-oxo-1-propylamino-1,6-dihydro-pyridine-3-carboxylic acid [(S)-cyclobutyl-(3-fluoro-phenyl)-methyl]-amide
1b  5-Bromo-2,4-dimethyl-6-oxo-1-propylamino-1,6-dihydro-pyridine-3-carboxylic acid [(S)-cyclopropyl-(4-fluoro-phenyl)-methyl]-amide
1c  5-Bromo-2,4-dimethyl-6-oxo-1-propylamino-1,6-dihydro-pyridine-3-carboxylic acid [(S)-(3-chloro-phenyl)-cyclopropyl-methyl]-amide
1d  5-Bromo-2,4-dimethyl-6-oxo-1-propylamino-1,6-dihydro-pyridine-3-carboxylic acid [(S)-(4-chloro-phenyl)-cyclopropyl-methyl]-amide
1e  5-Bromo-2,4-dimethyl-6-oxo-1-propylamino-1,6-dihydro-pyridine-3-carboxylic acid [(S)-1-(2-fluoro-phenyl)-propyl]-amide
1f  5-Bromo-2,4-dimethyl-6-oxo-1-propylamino-1,6-dihydro-pyridine-3-carboxylic acid [(S)-1-(3-fluoro-phenyl)-propyl]-amide
1g  5-Bromo-2,4-dimethyl-6-oxo-1-propylamino-1,6-dihydro-pyridine-3-carboxylic acid [(S)-1-(4-fluoro-phenyl)-propyl]-amide
1h  5-Bromo-2,4-dimethyl-6-oxo-1-propylamino-1,6-dihydro-pyridine-3-carboxylic acid ((S)-2-methyl-1-phenyl-propyl)-amide
1i  5-Bromo-2,4-dimethyl-6-oxo-1-propylamino-1,6-dihydro-pyridine-3-carboxylic acid ((S)-cyclobutyl-phenyl-methyl)-amide
1j  5-Bromo-2,4-dimethyl-6-oxo-1-propylamino-1,6-dihydro-pyridine-3-carboxylic acid ((S)-cyclopentyl-phenyl-methyl)-amide
1k  5-Bromo-2,4-dimethyl-6-oxo-1-propylamino-1,6-dihydro-pyridine-3-carboxylic acid [(S)-cyclobutyl-(4-fluoro-phenyl)-methyl]-amide
1l  5-Bromo-2,4-dimethyl-6-oxo-1-propylamino-1,6-dihydro-pyridine-3-carboxylic acid [(S)-cyclopropyl-(3-fluoro-phenyl)-methyl]-amide
1m  5-Bromo-2,4-dimethyl-6-oxo-1-propylamino-1,6-dihydro-pyridine-3-carboxylic acid ((S)-cyclopropyl-phenyl-methyl)-amide
1n  5-Bromo-2,4-dimethyl-6-oxo-1-propylamino-1,6-dihydro-pyridine-3-carboxylic acid [(S)-1-(4-chloro-phenyl)-propyl]-amide
1o  5-Bromo-2,4-dimethyl-6-oxo-1-propylamino-1,6-dihydro-pyridine-3-carboxylic acid [(S)-1-(3-chloro-phenyl)-propyl]-amide
1p  5-Bromo-2,4-dimethyl-6-oxo-1-propylamino-1,6-dihydro-pyridine-3-carboxylic acid ((S)-cyclohexyl-phenyl-methyl)-amide
1q  5-Bromo-2,4-dimethyl-6-oxo-1-propylamino-1,6-dihydro-pyridine-3-carboxylic acid ((S)-1-phenyl-propyl)-amide
1r  5-Bromo-2,4-dimethyl-6-oxo-1-propyl-1,6-dihydro-pyridine-3-carboxylic acid [(S)-cyclopropyl-(4-fluoro-phenyl)-methyl]-amide
1s  5-Bromo-2,4-dimethyl-6-oxo-1-propyl-1,6-dihydro-pyridine-3-carboxylic acid [(S)-(2-chloro-phenyl)-cyclopropyl-methyl]-amide
1t  5-Bromo-2,4-dimethyl-6-oxo-1-propyl-1,6-dihydro-pyridine-3-carboxylic acid [(S)-(3-chloro-phenyl)-cyclopropyl-methyl]-amide
1u  5-Bromo-2,4-dimethyl-6-oxo-1-propyl-1,6-dihydro-pyridine-3-carboxylic acid [(S)-(4-chloro-phenyl)-cyclopropyl-methyl]-amide
1v  5-Bromo-2,4-dimethyl-6-oxo-1-propyl-1,6-dihydro-pyridine-3-carboxylic acid [(S)-1-(2-fluoro-phenyl)-propyl]-amide
1w  5-Bromo-2,4-dimethyl-6-oxo-1-propyl-1,6-dihydro-pyridine-3-carboxylic acid [(S)-1-(3-fluoro-phenyl)-propyl]-amide
1x  5-Bromo-2,4-dimethyl-6-oxo-1-propyl-1,6-dihydro-pyridine-3-carboxylic acid [(S)-1-(4-fluoro-phenyl)-propyl]-amide
1y  5-Bromo-2,4-dimethyl-6-oxo-1-propyl-1,6-dihydro-pyridine-3-carboxylic acid ((S)-2-methyl-1-phenyl-propyl)-amide
1z  5-Bromo-2,4-dimethyl-6-oxo-1-propyl-1,6-dihydro-pyridine-3-carboxylic acid ((S)-cyclobutyl-phenyl-methyl)-amide
1aa  5-Bromo-2,4-dimethyl-6-oxo-1-propyl-1,6-dihydro-pyridine-3-carboxylic acid ((S)-cyclopentyl-phenyl-methyl)-amide
1ab  5-Bromo-2,4-dimethyl-6-oxo-1-propyl-1,6-dihydro-pyridine-3-carboxylic acid [cyclobutyl-(2-fluoro-phenyl)-methyl]-amide 1ac 5-Bromo-2,4-dimethyl-6-oxo-1-propyl-1,6-dihydro-pyridine-3-carboxylic acid [(S)-cyclobutyl-(4-fluoro-phenyl)-methyl]-amide
1ad 5-Bromo-2,4-dimethyl-6-oxo-1-propyl-1,6-dihydro-pyridine-3-carboxylic acid [(S)-cyclopropyl-(3-fluoro-phenyl)-methyl]-amide
1ae 5-Bromo-2,4-dimethyl-6-oxo-1-propyl-1,6-dihydro-pyridine-3-carboxylic acid ((S)-cyclopropyl-phenyl-methyl)-amide
1af 5-Bromo-2,4-dimethyl-6-oxo-1-propyl-1,6-dihydro-pyridine-3-carboxylic acid [(S)-1-(4-chloro-phenyl)-propyl]-amide
1ag 5-Bromo-2,4-dimethyl-6-oxo-1-propyl-1,6-dihydro-pyridine-3-carboxylic acid [(S)-1-(3-chloro-phenyl)-propyl]-amide
1ah 5-Bromo-2,4-dimethyl-6-oxo-1-propyl-1,6-dihydro-pyridine-3-carboxylic acid ((S)-1-phenyl-propyl)-amide
1ai 5-Bromo-2,4-dimethyl-6-oxo-1-propyl-1,6-dihydro-pyridine-3-carboxylic acid [(S)-cyclobutyl-(3,4-difluoro-phenyl)-methyl]-amide
1aj 5-Bromo-2,4-dimethyl-6-oxo-1-propyl-1,6-dihydro-pyridine-3-carboxylic acid ((S)-cyclohexyl-phenyl-methyl)-amide
1ak 5-Bromo-2,4-dimethyl-6-oxo-1-propyl-1,6-dihydro-pyridine-3-carboxylic acid [(S)-cyclobutyl-(3,5-difluoro-phenyl)-methyl]-amide
1al 5-Bromo-2,4-dimethyl-6-oxo-1-propyl-1,6-dihydro-pyridine-3-carboxylic acid [(S)-cyclopropyl-(3,4-difluoro-phenyl)-methyl]-amide
1am 5-Bromo-2,4-dimethyl-6-oxo-1-propyl-1,6-dihydro-pyridine-3-carboxylic acid [(R)-cyclopropyl-(3-fluoro-phenyl)-methyl]-amide
1an 4-Chloro-2-methyl-6-oxo-1-propyl-1,6-dihydro-pyridine-3-carboxylic acid [(5)-cyclobutyl-(3-fluoro-phenyl)-methyl]-amide
2a 5-Bromo-2,4-dimethyl-6-oxo-1-phenyl-1,6-dihydro-pyridine-3-carboxylic acid [(S)-cyclobutyl-(3-fluoro-phenyl)-methyl]-amide
2b 5-Bromo-2,4-dimethyl-6-oxo-1-propylamino-1,6-dihydro-pyridine-3-carboxylic acid [(S)-cyclobutyl-(3-fluoro-phenyl)-methyl]-amide
2c 5-Bromo-1-ethylamino-2,4-dimethyl-6-oxo-1,6-dihydro-pyridine-3-carboxylic acid [(S)-cyclobutyl-(3-fluoro-phenyl)-methyl]-amide
2d 5-Bromo-2,4-dimethyl-6-oxo-1-propyl-1,6-dihydro-pyridine-3-carboxylic acid [(S)-cyclobutyl-(3-fluoro-phenyl)-methyl]-amide
2e 5-Bromo-4-ethyl-2-methyl-6-oxo-1-phenyl-1,6-dihydro-pyridine-3-carboxylic acid [(S)-cyclobutyl-(3-fluoro-phenyl)-methyl]-amide
2f 5-Bromo-2-methyl-6-oxo-1-phenyl-4-propyl-1,6-dihydro-pyridine-3-carboxylic acid [(S)-cyclobutyl-(3-fluoro-phenyl)-methyl]-amide
2g 5-Bromo-2-methyl-6-oxo-1-phenyl-4-trifluoromethyl-1,6-dihydro-pyridine-3-carboxylic acid [(S)-cyclobutyl-(3-fluoro-phenyl)-methyl]-amide
2h 5-Bromo-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide
2i 5-Bromo-2-methyl-4-methylamino-6-oxo-1-propyl-1,6-dihydro-pyridine-3-carboxylic acid [(S)-cyclobutyl-(3-fluoro-phenyl)-methyl]-amide
2j 5-Chloro-2,4-dimethyl-6-oxo-1-phenyl-1,6-dihydro-pyridine-3-carboxylic acid [(S)-cyclobutyl-(3-fluoro-phenyl)-methyl]-amide
2k 5-Chloro-4-ethyl-2-methyl-6-oxo-1-phenyl-1,6-dihydro-pyridine-3-carboxylic acid [(S)-cyclobutyl-(3-fluoro-phenyl)-methyl]-amide
2l 5-Chloro-2-methyl-6-oxo-1-phenyl-4-propyl-1,6-dihydro-pyridine-3-carboxylic acid [(S)-cyclobutyl-(3-fluoro-phenyl)-methyl]-amide
2m 5-Chloro-2-methyl-6-oxo-1-phenyl-4-trifluoromethyl-1,6-dihydro-pyridine-3-carboxylic acid [(S)-cyclobutyl-(3-fluoro-phenyl)-methyl]-amide
2n 5-Chloro-2-methyl-4-methylamino-6-oxo-1-propyl-1,6-dihydro-pyridine-3-carboxylic acid [(S)-cyclobutyl-(3-fluoro-phenyl)-methyl]-amide
2o 5-Fluoro-2,4-dimethyl-6-oxo-1-phenyl-1,6-dihydro-pyridine-3-carboxylic acid [(S)-cyclobutyl-(3-fluoro-phenyl)-methyl]-amide
3a 5-Cyano-2,4-dimethyl-6-oxo-1-phenyl-1,6-dihydro-pyridine-3-carboxylic acid [(S)-cyclobutyl-(3-fluoro-phenyl)-methyl]-amide
3b 5-Cyano-2,4-dimethyl-6-oxo-1-propylamino-1,6-dihydro-pyridine-3-carboxylic acid [(S)-cyclobutyl-(3-fluoro-phenyl)-methyl]-amide
3c 5-Cyano-2,4-dimethyl-6-oxo-1-propyl-1,6-dihydro-pyridine-3-carboxylic acid [(S)-cyclobutyl-(3-fluoro-phenyl)-methyl]-amide
3d 5-Cyano-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide
3e 5-Ethynyl-2,4-dimethyl-6-oxo-1-phenyl-1,6-dihydro-pyridine-3-carboxylic acid [(S)-cyclobutyl-(3-fluoro-phenyl)-methyl]-amide
3f 5-Ethyl-2,4-dimethyl-6-oxo-1-phenyl-1,6-dihydro-pyridine-3-carboxylic acid [(5)-cyclobutyl-(3-fluoro-phenyl)-methyl]-amide
3g 2,4,5-Trimethyl-6-oxo-1-phenyl-1,6-dihydro-pyridine-3-carboxylic acid [(S)-cyclobutyl-(3-fluoro-phenyl)-methyl]-amide Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention. In particular, when A represents CH or CR$^1$, A may be an optical centre giving rise to two optical isomers, an R form and an S form.

In a particular embodiment, the compounds of the present invention have the following absolute configuration at A, A being CH

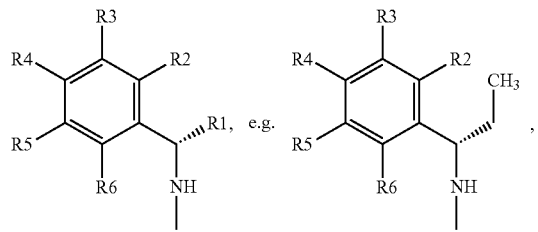

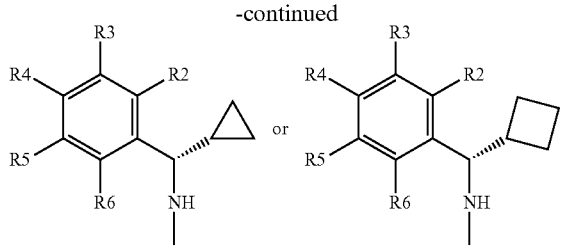

In this context is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

NK3 receptor antagonists have been implicated in various diseases in addition to psychosis and schizophrenia discussed above. Langlois et al in *J. Pharm. Exp. Ther.*, 299, 712-717, 2001, concludes that NK3 antagonists may be applicable in CNS diseases in general, and in anxiety and depression in particular. Yip et al in *Br. J. Phar.*, 122, 715-722, 1997 further implicates NK3 antagonists in diverse brain functions, such as cortical processing, learning and memory, neuroendocrine and behavioral regulation. Additional studies have shown that NKB and NK3 receptors are involved in pain, and that NK3 antagonists have an antinociceptive and analgesic effect [Fioramonti, *Neurogastroenterol. Motil.*, 15, 363-369, 2003]. Mazelin et al in *Life Sci.*, 63, 293-304, 1998 show that NK3 antagonists have an effect in gut inflammation and concludes that such antagonists may be used in the treatment of irritable bowel syndrome (IBS). In addition, NK3 antagonists have in in vivo models been demonstrated to be useful in the treatment of airway related diseases, such as asthma, airway hyperresponsiveness, cough, and bronchorestriction [Daoui, *Am. J. Respir. Crit. Care Med.*, 158, 42-48, 1998]. Maubach et al in *Neurosci.*, 83, 1047-1062, 1998 show that NKB and the NK3 agonist senktide increase the frequency and duration of epileptiform discharges, and thus by inference that NK3 antagonists have an anticonvulsive potential. Finally, Kernel et al in *J. Neurosci.*, 22, 1929-1936, 2002, suggests the use of NK3 antagonists in the treatment of Parkinson's Disease.

Accordingly, clinical, pre-clinical, in vivo and in vitro studies support that NK3 receptor antagonists are of relevance for the treatment or prevention of various disorders including psychosis, schizophrenia, depression, anxiety, cognitive impairment, obesity, Alzheimer's disease, Parkinson's disease, pain, convulsions, cough, asthma, airway hyperresponsiveness, microvascular hypersensitivity, bronchoconstriction, gut inflammation, and inflammatory bowel syndrome.

Schizophrenia is classified into subgroups. The paranoid type is characterised by delusions and hallucinations and absence of thought disorder, disorganized behavior, and affective flattening. The disorganized type, which is also named 'hebephrenic schizophrenia' in the ICD, in which thought disorder and flat affect are present together. The cataconic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics are fairly successful in treating the positive symptoms but fare less well for the negative and cognitive symptoms. Contrary to that, NK3 antagonists have been shown clinically to improve on both positive and negative symptoms in schizophrenics [*Am. J. Psychiatry*, 161, 975-984, 204], and according to the above discussion they are also expected to deliver an effect on the cognitive symptoms.

Cognitive impairment includes a decline in cognitive functions or cognitive domains, e.g. working memory, attention and vigilance, verbal learning and memory, visual learning and memory, reasoning and problem solving e.g. executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

In one embodiment, the present invention relates to the compounds of the present invention for use in therapy.

In one embodiment, the present invention relates to pharmaceutical compositions comprising compounds of formula I and pharmaceutically acceptable salts thereof in combination with one or more pharmaceutically acceptable carrier or excipient.

In one embodiment, the present invention relates to a method of treating a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTSD; dementia and agitation and delirium in the elderly. The method comprising the administration of a therapeutically effective amount of a compound of the present invention to a patient in need thereof.

In one embodiment, the present invention relates to a method for the treatment of schizophrenia, the method comprising the administration of a therapeutically effective amount of a compound of the present invention to a patient in need thereof. In particular, said treatment includes the treatment of the positive, negative and/or cognitive symptoms of schizophrenia.

In one embodiment, the present invention relates to a method of treating cognitive impairment, the method comprising the administration of a therapeutically effective amount of a compound of the present invention to a patient in need thereof. In particular, said cognitive impairment is manifested as a decline in working memory, attention and vigilance, verbal learning and memory, visual learning and memory, reasoning and problem solving e.g. executive function, speed of processing and/or social cognition.

The antipsychotic effect of typical and atypical anti-psychotics, in particular D2 antagonists is exerted via an inhibition of the post-synaptic D2 receptors. Pre-synaptic D2 auto-receptors, however, are also affected by the administration of these compounds giving rise to an increase in the dopamine neuron firing rate, which, in fact, counteracts the antipsychotic effects. The increased firing rate continues until the effect of the pre-synaptic auto-receptors is blocked (the depolarization block), typically after approximately 3 weeks of chronic treatment with typical or atypical anti-psychotics. This model explains the up to 3 weeks delay of clinical effect normally seen when D2 antagonist treatment is initiated. NK3 antagonists seem to inhibit the increase in the dopamine neuron firing mediated by the pre-synaptic D2 auto-receptors brought about by D2 antagonists, wherefore the combined administration of NK3 antagonists and D2 antagonists is expected to give rise to a faster onset of the clinical effect. Moreover, D2 antagonists are known to increase prolactin levels, which may give rise to serious side effects, such as osteoporosis. It is known that NK3 agonists give rise to an increase in prolactin from which it may be deduced that a NK3 antagonist will lower an increased, i.e. normalise the prolactin level. A combined use of NK3 antagonists and D2 antagonists may thus address some of the safety aspects associated with D2 antagonists administration. Similarly, NK3 antagonists may be administered together with antagonists/inverse agonists/negative modulators/partial agonists of one or more of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Such combined administration of compounds of the present invention and other anti-psychotic compounds, such as D2 antagonists, D2 partial agonists, PDE10 antagonists, 5-$HT_{2A}$ antagonists, 5-$HT_6$ antagonists or KCNQ4 antagonists may be sequential or concomitant. Examples of D2 antagonists or partial agonists include haloperidol, chlorpromazine, sulpirid, risperidone, ziprasidon, olanzapine, quetiapin, and clozapine.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

In one embodiment, the present invention relates to the use of the compounds of the present invention in the manufacture of a medicament for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTSD; dementia and agitation and delirium in the elderly.

In one embodiment, the present invention relates to the use of a compound of the present invention in the manufacture of a medicament for the treatment of schizophrenia. In particular, said treatment includes the treatment of the positive, negative and/or cognitive symptoms of schizophrenia.

In one embodiment, the present invention relates to the use of a compound of the present invention in the manufacture of a medicament for the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

In one embodiment, the present invention relates to a compound of the present invention for use in the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTSD; dementia and agitation and delirium in the elderly. In one embodiment, the present invention relates to a compound of the present invention for use in the treatment of schizophrenia. In particular, said treatment includes the treatment of the positive, negative and/or cognitive symptoms of schizophrenia.

In one embodiment, the present invention relates to a compound of the present invention for use in the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In one embodiment, the invention relates to a pharmaceutical composition comprising a compound of the present invention together with a second anti-psychotic agent. In one embodiment, said second anti-psychotic agent is selected from antagonists/inverse agonists/negative modulators/partial agonists of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or from agonists/positive modulators/partial agonists of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor. In one embodiment, said second anti-psychotic agent is selected from typical anti-psychotics, atypical anti-psychotics, D2 antagonists, partial D2 agonists, PDE10 antagonists, 5-$HT_{2A}$ antagonists, 5-$HT_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

In one embodiment, the invention relates to a pharmaceutical kit comprising a container comprising a compound of the present invention and a separate container comprising an anti-psychotic drug. Typical anti-psychotics, atypical anti-psychotics, D2 antagonists, partial D2 agonists, PDE10 antagonists, 5-HT$_{2A}$ antagonists, 5-HT$_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

The compounds of the present invention of the general formula I, wherein R$^1$-R$^8$, A, X, Q, and Y are as defined above can be prepared by the methods outlined in the following reaction schemes and examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

In the intermediate compounds of the general formulae II-XII, R$^1$-R$^8$, A, X, Q, and Y are as defined under formula I.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers. Such compounds include, but not limited to enamines of the general formula X, which may exist in equilibrium between keto or enol forms and the latter may also exist in isomeric Z- and E-forms as well-known to chemists skilled in the art. Such compounds also include compounds of the present invention of the general formula I, which may exist as a mixture of atropisomers due to restricted rotation around carbon-carbon single bonds similar to atropisomerism in ortho, ortho'-disubstituted biaryl compounds also well-known to the person skilled in the art.

Starting materials of the general formulae III, IV, VI, and X are obtained from commercial sources as summarised in the Table 3 or they can be readily prepared by standard methods or their modifications described in the literature.

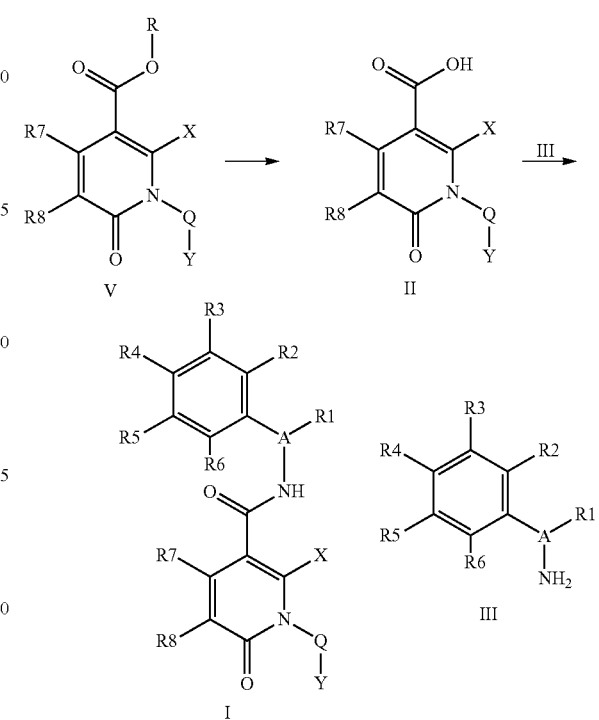

Scheme 1

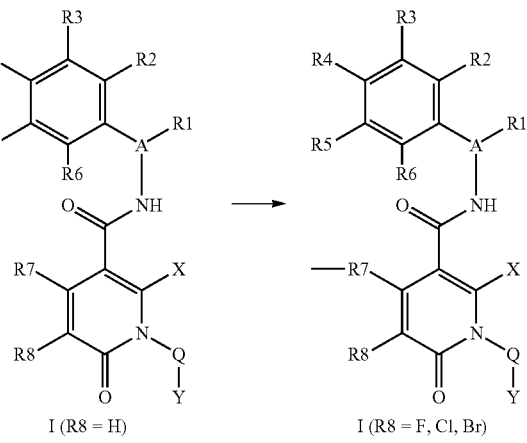

Scheme 2

Scheme 3
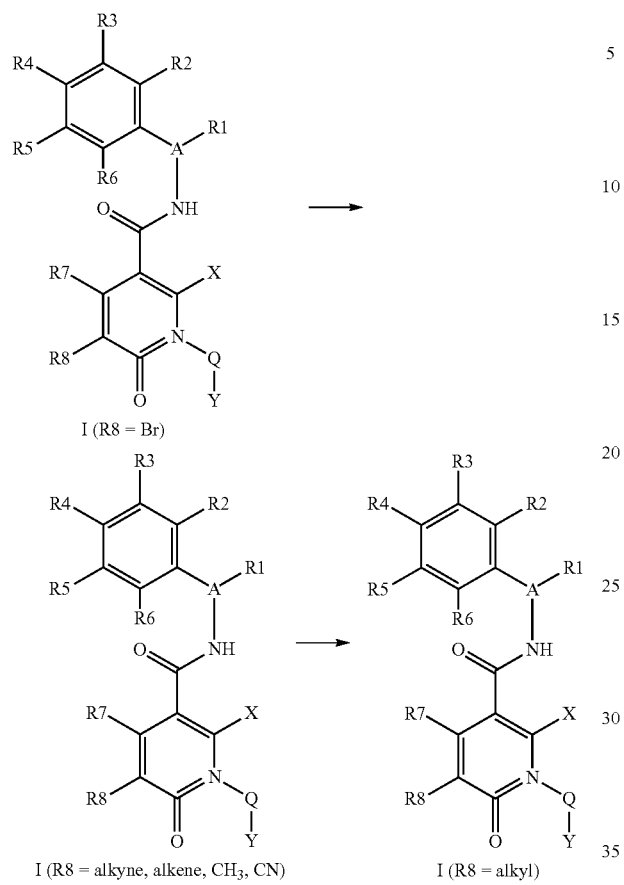
I (R8 = Br)
I (R8 = alkyne, alkene, CH3, CN) → I (R8 = alkyl)
Scheme 4
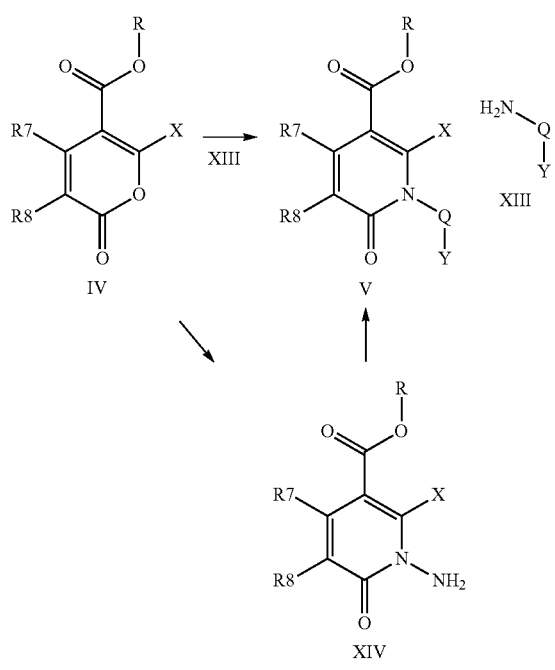
Scheme 5
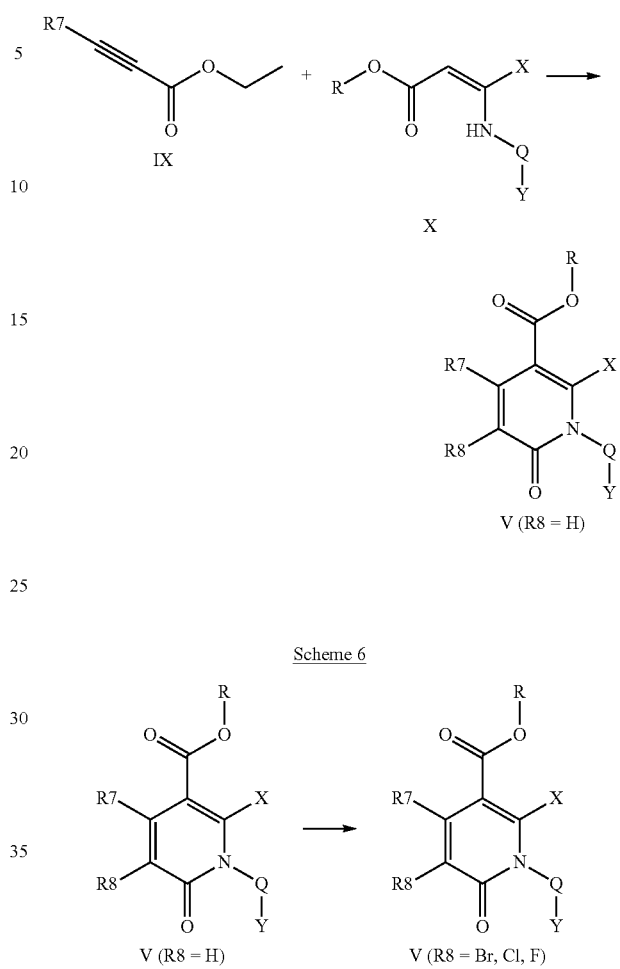
V (R8 = H)
Scheme 6
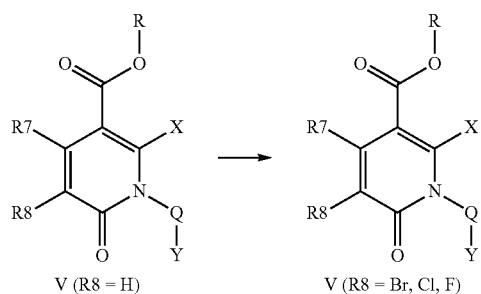
V (R8 = H) → V (R8 = Br, Cl, F)
Scheme 7
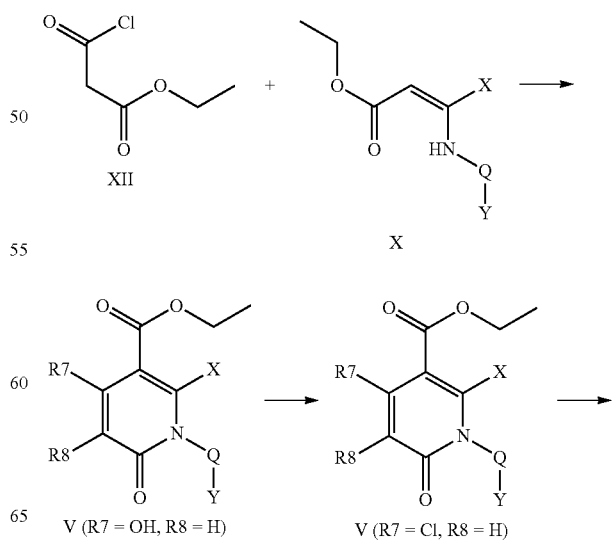
V (R7 = OH, R8 = H) → V (R7 = Cl, R8 = H)

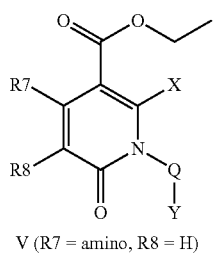

V (R7 = amino, R8 = H)

Scheme 8

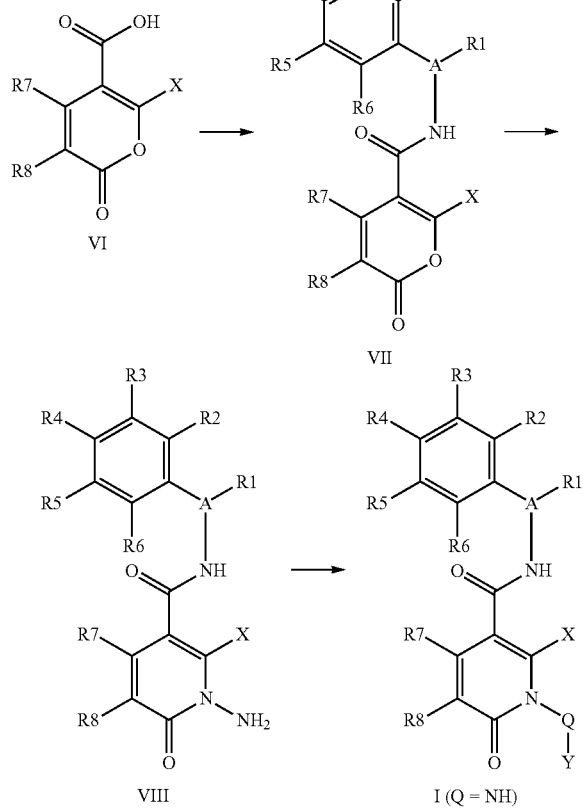

Pyridinone esters of the general formula V are readily hydrolyzed to acids of the general formula II under conditions for ester hydrolysis well known to chemists skilled in the art. The subsequent coupling with amines of the general formula III leads to the formation of the compounds of the invention of the general formula I (Scheme 1). Such an amide coupling reactions are usually performed via activation of the acid with an appropriate coupling or activation reagent such as but not limited to thionyl chloride with the formation of corresponding acid chloride or in the presence EDC/HOBT or HATU reagent (Scheme 1).

Pyridinone esters of the general formula V can be prepared from corresponding pyranone-carboxylic acid esters of the general formula IV by condensation with amino compounds of the general formula XIII under heating conditions with or without a catalyst such as acetic acid. Alternatively, such condensation can be performed with hydrazine or hydrazine salts with the formation of N-aminopyridinones of the general formula XIV which are further converted to desired compounds of the general formula V (where Q=NH) by an alkylation reaction such as reductive alkylation as well known to chemists skilled in the art (Scheme 4).

Enamine-carboxylic esters of the general formula X can be condensed with alkynes of the general formula IX under basic conditions with spontaneous cyclisation into pyridinone esters of the general formula V where $R^8$=H (Scheme 5). Enamines X can be also condensed with ethyl malonyl chloride XII with formation of pyridinone esters of the general formula V where $R^7$=OH. The hydroxyl group can be readily converted into chloride and then to substituted amino group by chlorination reaction with phosphoryl chloride followed by nucleophilic substitution with the corresponding amine (Scheme 7).

Pyridinone esters of the general formula V where $R^8$=H can be converted into corresponding chloro-, bromo-, or fluoro-derivatives by electrophilic substitution reactions with N-bromosuccinimide or N-chlorosuccinimide, or electrophilic fluorine reagents such as Selectfluor, respectively (Scheme VI). Compounds of the invention of the general formula I where $R^8$=Cl, Br, or F are prepared by the same method from corresponding compounds of the same general formula I with $R^8$=H (Scheme 2).

Pyranone-carboxylic acids of general formula VI are coupled with amines of the formula III under conditions for amide coupling reactions as described above with formation of pyranone-carboxamides of the general formula VII. The latter can be condensed with amino compounds of the general formula XIII or with hydrazine with formation of the compounds of the general formula I or VIII, respectively (Scheme 8), in a similar way as described above for the Scheme 4. Amino compounds of the general formula VIII can be converted into compounds of the general formula I (Q=NH) by reductive alkylation reaction.

Compounds of the invention of the general formula I with $R^8$=Br can be further converted into corresponding alkyne-, cyano-, or methyl derivatives (Scheme III) by well-known transition metal catalysed carbon-carbon bond formation reactions. Alkyne substituents ($R^8$) could be further reduced into alkane by hydrogenation reaction.

EXAMPLES

Analytical LC-MS, method A: data were obtained on a Sciex API 150EX analytical LC/MS system equipped with Applied Biosystems API150EX single qaudrupole mass spectrometer and atmospheric pressure photo ionisation (APPI) ion source, Shimadzu LC10ADvp LC pumps (3×), Shimadzu SPD-M20A photodiode array detector, SEDERE Sedex 85-low temperature Evaporative Light Scattering Detector (ELSD), Shimadzu CBM-20A system controller, Gilson 215 autosampler and Gilson 864 degasser controlled by Analyst Software. Column: 30×4.6 mm Waters Symmetry C18 column with 3.5 μm particle size; Injection Volume: 15 μL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 2.4 minutes then with 10% B in 0.4 minutes and with a flow rate of 3.3 mL/minute. The retention times ($t_R$) are expressed in minutes based on UV-trace at 254 nm.

Analytical LC-MS, method B: data were obtained on a Sciex API300 analytical LC/MS system equipped with Applied Biosystems API300 triple qaudrupole mass spectrometer with atmospheric pressure photo ionisation (APPI)

ion source, Shimadzu LC10ADvp LC pumps (3×), Shimadzu SPD-M20A photodiode array detector, Polymer Labs PL-ELS 2100-low temperature Evaporative Light Scattering Detector (ELSD), Shimadzu SCL10A VP system controller, Gilson 215 autosampler and Gilson 864 degasser controlled by Analyst Software. Column: Symmetry C18 3.5 µm, 4.6× 30 mm 30×4.6 mm; Injection Volume: 5 µL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 1.45 minutes then with 10% B in 0.55 minutes and with a flow rate of 5.5 mL/minute:

| Time, min. | % B |
|---|---|
| 0.00 | 10.0 |
| 1.45 | 100.0 |
| 1.55 | 10.0 |
| 2.0 | 10.0 |

The retention times ($t_R$) are expressed in minutes based on UV-trace at 254 nm.

Analytical LC-MS, method C: the same instrument and the column was used as in the method A, except 100% methanol with 0.035% trifluoroacetic acid was used for the solvent system B; Flow: 3.0 ml/min; injection volume: 10 µl (1 µl injected on the column).

Gradient:

| | |
|---|---|
| 0.01 min | 17% B (v/v) |
| 0.27 min | 28% B |
| 0.53 min | 39% B |
| 0.80 min | 50% B |
| 1.07 min | 59% B |
| 1.34 min | 68% B |
| 1.60 min | 78% B |
| 1.87 min | 86% B |
| 2.14 min | 93% B |
| 2.38 min | 100% B |
| 2.40 min | 17% B |
| 2.80 min | 17% B |
| Total run time: 2.8 min | |

Total run time: 2.8 min
The retention times ($t_R$) are expressed in minutes based on UV-trace at 254 nm.

Preparative LC-MS purification was performed on the same Sciex API 150EX system equipped with Gilson 333 and 334 pumps, Gilson GX 281 autosampler/fraction collector, Shimadzu LC10ADvp pump, Gilson UV/VIS 155 UV detector, Gilson 506C system interface, Gilson 864 degasser, Passive flowsplitters (approx. 1:1000). The MS and fraction collector were controlled by Masschrom software (Macintosh PC). The LC system was controlled by Trilution software version 2.0 (HP Compaq). The MS was controlled by Analyst (PC-Dell 390). For a small scale (<20 mg) purification fractions were collected in 4 ml vials using Sunfire Prep C18 5 µm, 10×100 mm, injection volume of 0-200 µL, flow rate of 15 ml/min and duration of 7.5 min, temperature +40° C. For a larger scale purification fractions were collected in 10 ml testtubes using Sunfire Prep C18 5 µm, 19×50 mm, injection volume of 0-200 µL, flow rate of 15 ml/min, temperature +40° C.

Solvents: A: Water containing 0.05% v/v TFA; B: Methanol containing 0.05% v/v TFA

| Time, min. | % B |
|---|---|
| 0.00 | 10.0 |
| 3.00 | 100.0 |
| 3.20 | 100.0 |
| 3.21 | 10.0 |

LC-High resolution MS was performed on Bruker Daltonics micrOTOF instrument with electrospray ion source and time-of-flight mass detector.

$^1$H NMR spectra were recorded at 500.13 MHz on a Bruker Avance DRX-500 instrument at T=303.3 K or at 600 MHz on a Bruker Avance AV-III-600 instrument. $^{13}$C NMR were recorded on both instruments. $^{19}$F NMR and variable temperature $^1$H NMR were recorded on the Bruker Avance DRX-500 instrument. Deuterated dimethyl sulfoxide (DMSO-$d_6$, 99.8% D) was used as solvent unless noted otherwise. Tetramethylsilane was used as internal reference standard unless noted otherwise. Chemical shift values are expressed in ppm-values relative to tetramethylsilane unless noted otherwise. The following abbreviations or their combinations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and br=broad or broad singlet.

Microwave experiments were performed in sealed process vials or reactors using an Emrys Synthesizer or Emrys Optimizer EXP from Personal Chemistry or a Milestone Microsynth instrument from Milestone. When a reaction was heated in a microwave instrument, it was cooled to 25° C. before the next process step.

Preparation of Intermediates

Synthesis of Chiral and Racemic Amines of the General Formula III.

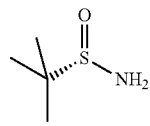

(S)-(−)-2-Methyl-2-propanesulfinamide

The title chiral auxiliary was prepared according to a described procedure for the (R)-(+)-enantiomer by D. J. Weix and J. A. Ellman *Organic Syntheses* 2005, 82, 157.

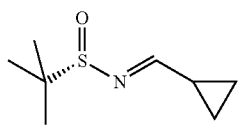

(S)-2-Methyl-2-propanesulfinic acid 1-cyclopropyl-methylideneamide

The title compound was prepared according to a general procedure described by G. Liu, D. A. Cogan, T. D. Owens, T. P. Tang, and J. A. Ellman *J. Org. Chem.* 1999, 64, 1278: A mixture of cyclopropanecarboxaldehyde (35.0 g, 0.5 mol), (S)-(−)-2-methyl-2-propanesulfinamide (30 g, 0.25 mol) and anhydrous CuSO$_4$ (120 g, 0.75 mol) in CH$_2$Cl$_2$ (1500 mL) was stirred at room temperature overnight. The reaction mixture was filtered and evaporated to give the title compound (39 g, yield 95%), which was used in the next step without further purification.

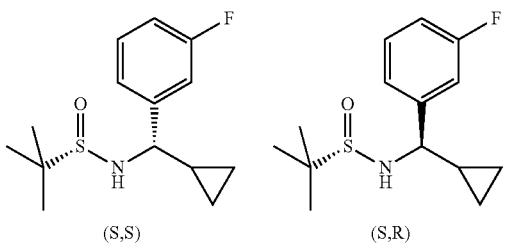

(S)-2-Methyl-2-propanesulfinic acid [(S)-cyclopropyl-(3-fluoro-phenyl)-methyl]-amide and (S)-2-Methyl-2-propanesulfinic acid [(R)-cyclopropyl-(3-fluoro-phenyl)-methyl]-amide The title compounds were obtained according to a general described procedure for 1,2-stereoselective addition of organometallic reagents to sulfinyl imines by D. A. Cogan, G. Liu, J. A. Ellman, *Tetrahedron* 1999, 55, 8883.

Procedure A: To an anhydrous lithium chloride (1.7 g, 40 mmol), THF (20 ml) was added under nitrogen followed by slow addition of i-PrMgCl (22 mL, 2 M in THF) and the obtained mixture was stirred at r.t. overnight. The obtained i-PrMgCl.LiCl solution was added dropwise to a stirred solution of 1-bromo-3-fluorobenzene (5.6 g, 33 mmol) in THF (25 ml) at 0° C. and stirring continued for 2 hours. The obtained Grignard reagent was added to a solution of (S)-2-methyl-2-propanesulfinic acid 1-cyclopropyl-methylideneamide (2.5 g, 14 mmol) in CH$_2$Cl$_2$ (60 mL) at −48° C. The mixture was stirred at −48° C. for 5 hours and then at room temperature overnight. The reaction mixture was quenched by addition of aq. sat. NH$_4$Cl (50 mL) and extracted with CH$_2$Cl$_2$ (3×100 mL). The combined organic solution was dried (Na$_2$SO$_4$) and evaporated to give a crude mixture, which was purified by column chromatography on silica gel (EtOAc/petroleum ether=1/10). The obtained mixture of diastereoisomers was resolved by SFC to give the title (S,S)-isomer as the major product (1.5 g, yield 37.5%) and the title (S,R)-isomer (0.16 g, yield: 4.0%).

Procedure B: Alternatively, to a suspension of Mg (13.4 g, 0.55 mol) in 50 mL of anhydrous THF at 50° C. a solution of 1-bromo-3-fluorobenzene (89.0 g, 0.50 mol) was added dropwise. The mixture was stirred for 2 hours at 50° C. and then added dropwise to a solution of (S)-2-methyl-2-propanesulfinic acid 1-cyclopropyl-methylideneamide (78.0 g, 0.46 mol) in 100 mL of THF at 50-60° C. and stirred for 2 hours. It was quenched with aq. sat. NH$_4$Cl (100 ml), water (300 mL), filtered, and the solid and filtrate were extracted with hot ethyl acetate (600 mL) and evaporated in vacuo. The residue was crystallized from a mixture of ethyl acetate and petroleum ether (1:1, 200 mL) at −20° C. to give 80 g of the title (S,S)-isomer as a white powder, 66% yield, de 100% according to chiral HPLC. $^1$H NMR (CDCl$_3$, 400 MHz, TMS=0 ppm): 7.34-7.28 (m, 1H), 7.16-7.12 (m, 2H), 7.00-6.96 (m, 1H), 3.68 (dd, J=8.8 Hz, 3.2 Hz, 1H), 3.52 (s, 1H), 1.42 (s, 9H), 1.15-1.08 (m, 1H), 0.84-0.75 (m, 1H), 0.69-0.61 (m, 1H), 0.55-0.46 (m, 1H), 0.28-0.21 (m, 1H).

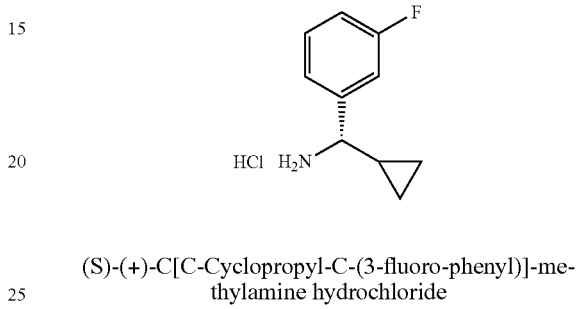

(S)-(+)-C[C-Cyclopropyl-C-(3-fluoro-phenyl)]-methylamine hydrochloride

To a saturated solution of HCl in anhydrous dioxane (400 ml) (S)-2-methyl-2-propanesulfinic acid [(S)-cyclopropyl-(3-fluoro-phenyl)-methyl]-amide (80 g, 0.3 mol) was added at 0° C. The mixture was allowed to warm to r.t. After stirring for 1 hour, the reaction mixture was evaporated in vacuo. The residue was washed with anhydrous ether (2×100 ml) and dried in vacuo to give 56 g of the title compound as a white solid, yield 93%, ee >99.9% according to chiral HPLC. $[\alpha]^{20}{}_D$=+52.69 (c=10 mg/mL, CH$_3$OH). $^1$H NMR (CD$_3$OD, 400 MHz): 7.44-7.39 (m, 1H), 7.25-7.19 (m, 2H), 7.12-7.07 (m, 1H), 3.56 (d, J=10.0 Hz, 1H), 1.37-1.28 (m, 1H), 0.78-0.75 (m, 1H), 0.61-0.55 (m, 2H), 0.39-0.36 (m, 1H).

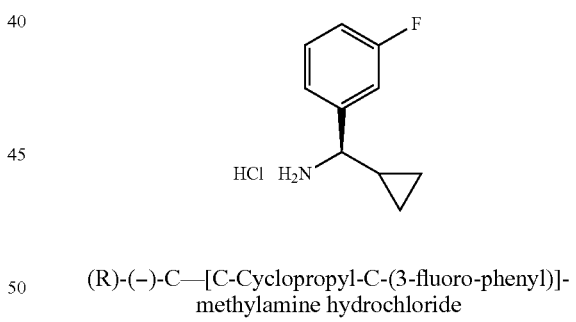

(R)-(−)-C—[C-Cyclopropyl-C-(3-fluoro-phenyl)]-methylamine hydrochloride

The title compound was prepared according to the above procedure from (S)-2-methyl-2-propanesulfinic acid [(R)-cyclopropyl-(3-fluoro-phenyl)-methyl]-amide (0.16 g, 0.6 mmol) to give 0.116 g of the title compound as a white solid. $[\alpha]^{20}{}_D$=−49.18 (c=10 mg/mL, CH$_3$OH), ee >99.9%. $^1$H NMR (CD$_3$OD, 400 MHz): identical with (S)-enantiomer.

The following enantiomerically pure amine hydrochlorides were obtained analogously in three-step procedure starting from condensation of the corresponding aldehyde with chiral auxiliary, stereoselective Grignard addition where the mixture of diastereoisomers was resolved either by recrystallisation or by chromatography (SFC or column) and the major (S,S)-diastereoisomer was finally converted to a chiral amine with HCl.

| Structure (HCl salt) | Chemical name | [α]²⁰D, (10 mg/ml) | ee (chiral HPLC) | ¹H NMR (CD₃OD, 400 MHz) |
|---|---|---|---|---|
| | C-[(S)-C-Cyclopropyl-C-(4-fluoro-phenyl)]-methylamine | +47.25 | 98.9 | 7.50-7.46 (m, 2H), 7.19-7.14 (m, 2H), 3.56 (d, J = 10.0 Hz, 1H), 1.40-1.31 (m, 1H), 0.83-0.76 (m, 1H), 0.67-0.54 (m, 2H), 0.40-0.31 (m, 1H) |
| | C-[(S)-C-(2-Chloro-phenyl)-C-cyclopropyl]-methylamine | +20.56 | 100 | 7.68 (dd, J = 7.6 Hz, 1.6 Hz, 1H), 7.52-7.38 (m, 3H), 4.12 (d, J = 9.6 Hz, 1H), 1.51-1.42 (m, 1H), 0.86-0.80 (m, 1H), 0.68-0.58 (m, 2H), 0.49-0.41 (m, 1H) |
| | C-[(S)-C-(3-Chloro-phenyl)-C-cyclopropyl]-methylamine | +54.25 | 96.9 | 7.55 (s, 1H), 7.50-7.42 (m, 3H), 3.61 (d, J = 10.0 Hz, 1H), 1.42-1.34 (m, 1H), 0.89-0.83 (m, 1H), 0.74-0.62 (m, 2H). |
| | C-[(S)-C-(4-Chloro-phenyl)-C-cyclopropyl]-methylamine | +59.1 | 96.2 | 7.47 (s, 4H), 3.60 (d, J = 10.4 Hz, 1H), 1.41-1.34 (m, 1H), 0.86-0.81 (m, 1H), 0.71-0.66 (m, 2H), 0.43-0.39 (m, 1H). |
| | (S)-1-(2-Fluoro-phenyl)-propylamine | −9.71 | 100 | 7.54-7.46 (m, 2H), 7.34-7.22 (m, 2H), 4.49 (dd, J = 9.2 Hz, 6.0 Hz, 1H), 2.13-1.96 (m, 2H), 0.95 (t, J = 6.8 Hz, 3H). |
| | (S)-1-(3-Fluoro-phenyl)-propylamine | +13.9 | 100 | 7.51-7.46 (m, 1H), 7.27-7.14 (m, 3H), 4.20 (dd, J = 9.2 Hz, 6.0 Hz, 1H), 2.07-1.89 (m, 2H), 0.89 (t, J = 7.2 Hz, 3H). |
| | (S)-1-(4-Fluoro-phenyl)-propylamine | +14.83 | 98.7 | 7.53-7.50 (m, 2H), 7.24-7.19 (m, 2H), 4.21 (dd, J = 9.2 Hz, 5.6 Hz, 1H), 2.13-1.91 (m, 2H), 0.89 (t, J = 7.2 Hz, 3H). |
| | (S)-1-(3-Chloro-phenyl)-propylamine | +14.46 | 100 | 7.48-7.35 (m, 4H), 4.17 (dd, J = 9.2 Hz, 6.0 Hz, 1H), 2.06-1.88 (m, 2H), 0.88 (t, J = 7.2 Hz, 3H). |
| | (S)-1-(4-Chloro-phenyl)-propylamine | +14.73 | 100 | 7.50-7.47 (m, 2H), 7.44-7.41 (m, 2H), 4.18 (dd, J = 9.6 Hz, 6.0 Hz, 1H), 2.07-1.90 (m, 2H), 0.89 (t, J = 7.6 Hz, 3H). |
| | (S)-2-Methyl-1-phenyl-propylamine | +7.12 | 100 | 7.47-7.37 (m, 5H), 3.91 (d, J = 9.2 Hz, 1H), 2.21-2.16 (m, 1H), 1.13 (d, J = 6.8 Hz, 3H), 0.78 (d, J = 6.8 Hz, 3H). |

| Structure (HCl salt) | Chemical name | [α]²⁰D, (10 mg/ml) | ee (chiral HPLC) | ¹H NMR (CD₃OD, 400 MHz) |
|---|---|---|---|---|
| | C-((S)-C-Cyclobutyl-C-phenyl)-methylamine | +17.57 | 95.4 | 7.37-7.31 (m, 5H), 4.12 (d, J = 10.4 Hz, 1H), 2.84-2.75 (m, 1H), 2.21-2.13 (m, 1H), 1.99-1.64 (m, 5H). |
| | C-((S)-C-Cyclopentyl-C-phenyl)-methylamine | +6.97 | 99.2 | 7.43 (br, 5H), 3.99 (d, J = 10.4 Hz, 1H), 2.46-2.40 (m, 1H), 2.02 (br, 1H), 1.76-1.08 (m, 8H). |
| | C-[(S)-C-Cyclobutyl-C-(3-fluoro-phenyl)]-methylamine | +19.45 | 100 | 7.48-7.44 (m, 1H), 7.24-7.15 (m, 3H), 4.26 (d, J = 10.4 Hz, 1H), 2.87-2.84 (m, 1H), 2.25-2.24 (m, 1H), 2.05-1.76 (m, 5H). |
| | C-[(S)-C-Cyclobutyl-C-(4-fluoro-phenyl)]-methylamine | +26.98 | 100 | 7.45-7.41 (m, 2H), 7.18-7.14 (m, 2H), 4.22 (d, J = 10.6 Hz, 1H), 2.89-2.81 (m, 1H), 2.28-2.21 (m, 1H), 2.05-1.71 (m, 5H). |
| | C-((S)-C-Cyclohexyl-C-phenyl)-methylamine | +4.8 | 100 | 7.46-7.34 (m, 5H), 3.92 (d, J = 9.2 Hz, 1H), 1.97-1.94 (m, 1H), 1.86-1.83 (m, 2H), 1.68-1.66 (m, 2H), 1.33-1.30 (m, 2H), 1.20-1.11 (m, 3H), 0.91-0.88 (m, 1H). |
| | C-[(S)-C-Cyclopropyl-C-(3,4-difluoro-phenyl)]-methylamine | +44.26 | 96 | 7.50-7.32 (m, 3H), 3.62 (d, J = 10.4 Hz, 1H), 1.38 (m, 1H), 0.86 (m, 1H), 0.68 (m, 1H), 0.62 (m, 1H), 0.45 (m, 1H) |
| | C-[(S)-C-Cyclobutyl-C-(3,4-difluoro-phenyl)]-methylamine | +27.22 | >99 | 7.41-7.32 (m, 2H), 7.25 (m, 1H), 4.26 (d, J = 10.4 Hz, 1H), 2.48 (m, 1H), 2.24 (m, 1H), 2.05-1.72 (m, 5H) |
| | C-[(S)-C-Cyclobutyl-C-(3,5-difluoro-phenyl)]-methylamine | +31.07 | 100 | 7.00-6.91 (m, 3H), 4.19 (d, J = 10.4 Hz, 1H), 2.79-2.68 (m, 1H), 2.18-2.11 (m, 1H), 1.98-1.69 (m, 5H) |

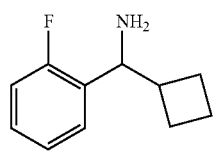

C-Cyclobutyl-C-(2-fluoro-phenyl)-methylamine

One third of a solution of cyclobutyl bromide (5.0 g, 41.3 mmol) in anhydrous tetrahydrofuran (24 mL) was stirred with magnesium (1.11 g, 46.3 mmol) under reflux. The remaining solution was added dropwise over a period of 15 minutes, and the stirring at reflux continued for 30 min. To the obtained solution 2-fluorobenzonitrile (1.2 g) in THF (15 ml) was added dropwise at 0° C. The mixture was stirred for 5.5 h at 0°

C. followed by addition of methanol (30 ml) and sodium borohydride (1.13 g). The reaction mixture was stirred for 16 hours at ambient temperature and concentrated. The residue was partitioned between chloroform (3×100 ml) and water, and the pH was adjusted to 1. The mixture was extracted with chloroform. The aqueous phase was adjusted to pH=10, and extracted with chloroform (3×100 ml). The combined organic layers were dried, evaporated and purified by column chromatography on silica gel (ethyl acetate/petroleum ether=1/1) to afford the title amine (0.45 g, yield: 7.9%) $^1$H NMR (CD$_3$OD, 400 MHz) 7.49-7.38 (m, 2H), 7.30-7.15 (m, 2H), 4.50 (d, J=10.4 Hz, 1H), 3.00-2.90 (m, 1H), 2.29-2.21 (m, 1H), 2.09-1.71 (m, 5H).

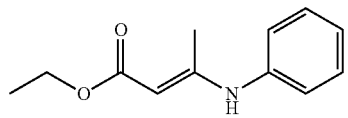

Ethyl 3-anilinobut-2-enoate

The title compound is commercially available. A mixture of aniline (9.785 mL, 107.4 mmol), ethyl acetoacetate (13.69 mL, 107.4 mmol), and acetic acid (0.6 mL, 10 mmol) was stirred at ambient temperature overnight. It was partitioned between heptane (50 mL) and sat. aq. NaHCO$_3$ solution (50 mL). The organic layer was dried and evaporated to give the title compound of >90% purity that was used in the next steps without further purification.

The following compounds were prepared analogously:

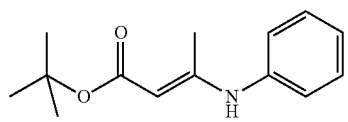

tert-Butyl 3-anilinobut-2-enoate $^1$H NMR (500 MHz, DMSO-d$_6$): 1.43 (s, 9H), 1.97 (s, 3H, Me), 4.59 (s, 1H), 7.14 (t, J=7.4 Hz, 1H, para-H of Ph), 7.16 (d, J=7.5 Hz, 2H, two ortho-H of Ph), 7.34 (t, J=7.5 Hz, 2H, two meta-H of Ph).

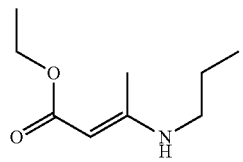

(E)-3-Propylamino-but-2-enoic acid ethyl ester

The product was used in the next step without purification.

Synthesis of Pyridones of the General Formula V According to Scheme 4:

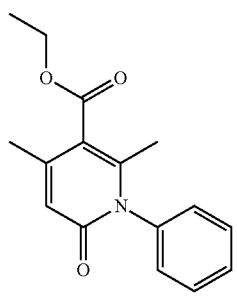

2,4-Dimethyl-6-oxo-1-phenyl-1,6-dihydro-pyridine-3-carboxylic acid ethyl ester

A mixture of 4,6-dimethyl-2-oxo-2H-pyran-5-carboxylic acid ethyl ester (=ethyl isodehydroacetate, 1.967 g, 10.02 mmol), aniline (1.865 g, 20.03 mmol) and acetic acid (0.5 mL, 9 mmol) was shaken at 90 C for 5 hours, then at 55° C. for 3 days. The excess of volatiles were removed in vacuo (0.1 mbar, 70 C, 30 min). It was transferred on to a SiO$_2$ column (50 g) with 1,2-dichloroethane/heptane 1:3 purified by flash chromatography with gradient 20% to 100% of ethyl acetate in heptane. The pure fractions gave 906 mg of the title compound as pale yellow oil, yield 33% (non-pure additional fractions gave 886 mg of the title compound contaminated with acetanilide and 4'-acetamidoacetophenone). LC-MS (m/z) 272.4 (MH+); t$_R$=1.07. $^1$H NMR (600 MHz, DMSO-d$_6$): 1.28 (t, J=7.1 Hz, 3H, Me of Et), 1.9 (s, 3H, 2-Me), 2.16 (d, J=0.9 Hz, 3H, 4-Me), 4.28 (q, J=7.1 Hz, 2H, CH$_2$ of Et), 6.3 (s, 1H, 5-H), 7.27 (dm, J=7.7 Hz, J<1.5 Hz, 2H, two ortho-H of Ph), 7.47 (tt, J=7.4 Hz, J=1.2 Hz, 1H, para-H of Ph), 7.53 (tm, J=7.5 Hz, J<1.7 Hz, 2H, two meta-H of Ph).

The following compounds were prepared analogously:

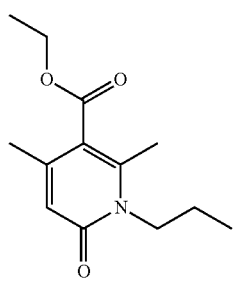

2,4-Dimethyl-6-oxo-1-propyl-1,6-dihydro-pyridine-3-carboxylic acid ethyl ester $^1$H NMR (400 MHz, CDCl$_3$): 0.93 (t, 3H, J=8 Hz), 1.31 (t, 3H, J=7.2 Hz), 1.63 (m, 2H), 2.12 (s, 3H), 2.37 (s, 3H), 3.95 (t, 2H, J=8 Hz), 4.29 (q, 2H, J=7.1 Hz), 6.39 (s, 1H).

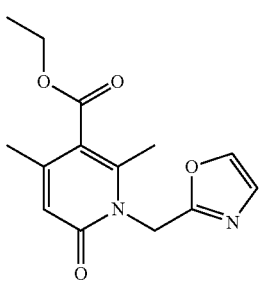

2,4-Dimethyl-1-oxazol-2-ylmethyl-6-oxo-1,6-dihydro-pyridine-3-carboxylic acid ethyl ester $^1$H NMR (400 MHz, CDCl$_3$): 1.30 (t, 3H, J=7 Hz), 2.12 (s, 3H), 2.38 (s, 3H), 4.27 (q, 2H, J=7 Hz), 5.36 (s, 2H), 6.30 (s, 1H), 7.00 (s, 1H), 7.54 (s, 1H).

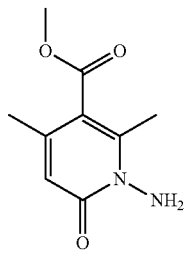

1-Amino-2,4-dimethyl-6-oxo-1,6-dihydro-pyridine-3-carboxylic acid methyl ester

A mixture of methyl isodehydroacetate (24.0 g, 132 mmol) and hydrazine monohydrochloride (9.6 g, 140 mmol) in ethanol (30 mL) was heated under microwave irradiation at 160° C. for 2 hours. It was filtered and the obtained solution was evaporated. The oil was partitioned between sat. aq. Na$_2$CO$_3$ and ethyl acetate (3×250 mL). The combined organic solution was washed with brine, dried (Na$_2$SO$_4$) and evaporated. The title product was purified by flash chromatography (yield 2.8 g, 10%). LC-MS (m/z) 197.0 (MH+); t$_R$=0.57 (method C). $^1$H NMR (600 MHz, CDCl$_3$): 2.20 (s, 3H, Me), 2.52 (s, 3H, Me), 3.88 (s, 3H, OMe), 5.16 (s, 2H, NH$_2$), 6.35 (s, 1H, C5-H).

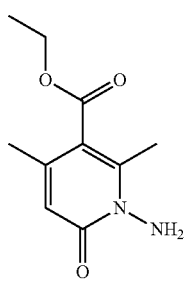

1-Amino-2,4-dimethyl-6-oxo-1,6-dihydro-pyridine-3-carboxylic acid ethyl ester

A mixture of 4,6-dimethyl-2-oxo-2H-pyran-5-carboxylic acid ethyl ester (3.2 mL, 19 mmol) and hydrazine monohydrochloride (1.4 g, 20 mmol) in methanol (16 mL, 0.39 mmol) was heated under microwave irradiation for 2.5 hrs at 150° C. Reaction was taken up in sat. aq. K$_2$CO$_3$ (40 mL) and extracted with ethyl acetate (3×40 mL). The combined organic phases were washed with brine, dried over MgSO$_4$, evaporated and purified by flash chromatography. Yield 7%. $^1$H NMR (500 MHz, CDCl$_3$): 6.35 (s, 1H), 5.12 (s, 2H), 4.35 (q, J=7.1 Hz, 2H), 2.53 (s, 3H), 2.21 (s, 3H), 1.37 (t, J=7.1 Hz, 3H).

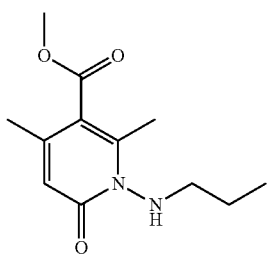

2,4-Dimethyl-6-oxo-1-propylamino-1,6-dihydro-pyridine-3-carboxylic acid methyl ester A mixture of 1-amino-2,4-dimethyl-6-oxo-1,6-dihydro-pyridine-3-carboxylic acid methyl ester (2.8 g, 14 mmol), propionaldehyde (5.1 mL, 71 mmol) and molecular sieves (size 4 Å, 5 g) in methanol (50 mL) was stirred overnight at room temperature. The solution was cooled to 5° C. and sodium tetrahydroborate (2.2 g, 57 mmol) was added in small portions. It was stirred for 1 hour at 5° C., then filtered and evaporated. The residue was partitioned between water (100 mL) and ethyl acetate (3×100 mL). The combined organic solution was dried (MgSO$_4$) and evaporated. The residue was treated with hot n-heptane, cooled to 10° C. and the unreacted starting material was removed by filtration. The heptane solution was purified by flash chromatography to give the title compound. LC-MS (m/z) 239.1 (MH+); t$_R$=1.20 (method C). $^1$H NMR (600 MHz, CDCl$_3$): 1.01 (t, J=7.4 Hz, 3H, Me of Pr), 1.61 (sextet, J=7.3 Hz, 2H, CH$_2$ of Pr), 2.19 (d, J=0.9 Hz, 3H, Me), 2.53 (s, 3H, Me), 2.56-3.1 (very br. coalescing d, 2H, CH$_2$N), 3.87 (s, 3H, OMe), 5.92 (t, J=7.3 Hz, 1H, NH), 6.35 (s, 1H, C5-H).

2,4-Dimethyl-6-oxo-1-propylamino-1,6-dihydro-pyridine-3-carboxylic acid ethyl ester To a mixture of 1-amino-2,4-dimethyl-6-oxo-1,6-dihydro-pyridine-3-carboxylic acid ethyl ester (220 mg, 1.0 mmol), propionaldehyde (0.301 mL, 4.18 mmol) and acetic acid (1 mL, 20 mmol) in methanol (10 mL, 300 mmol) was added sodium cyanoborohydride (0.263 g, 4.18 mmol) and the mixture was stirred at room temperature for 24 hrs. More propionaldehyde (0.301 mL, 4.18 mmol) and sodium cyanoborohydride (0.263 g, 4.18 mmol) were added and the mixture was stirred for 7 days at room temperature. The reaction mixture was concentrated in vacuo, poured into 2 M aq. NaOH (20 mL) and extracted with ethyl acetate (4×20 mL). The combined organic phases were washed with brine, dried over $MgSO_4$, evaporated and purified by flash chromatography. Yield 33%. LC-MS (m/z) 253.5 (MH$^+$); $t_R$=1.38 (method C). $^1$H NMR (600 MHz, CDCl$_3$): 6.34 (s, 1H), 5.91 (t, J=7.3 Hz, 1H), 4.35 (q, J=7.1 Hz, 2H), 3.14-2.58 (m, 2H), 2.53 (s, 3H), 2.20 (s, 3H), 1.61 (h, J=7.3 Hz, 2H), 1.38 (t, J=7.1 Hz, 3H), 1.01 (t, J=7.4 Hz, 3H). $^{13}$C NMR (151 MHz, CDCl$_3$): 167.36, 161.07, 147.65, 147.34, 116.25, 113.82, 61.39, 52.97, 21.10, 20.74, 16.55, 14.22, 11.55.

Synthesis of Pyridones of the General Formula V According to Scheme 5:

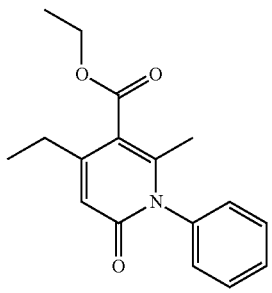

4-Ethyl-2-methyl-6-oxo-1-phenyl-1,6-dihydro-pyridine-3-carboxylic acid ethyl ester To a stirred solution of ethyl 3-anilinobut-2-enoate (50 mg, 0.2 mmol) in tetrahydrofuran (1 mL, 10 mmol) sodium hydride (60% NaH in mineral oil, 9.7 mg) was added. After 15 min ethyl 2-pentynoate (0.039 mL, 0.292 mmol) was added. After 60 min it was partitioned between ether (9 mL) and sat. aq. NaHCO$_3$ (3 mL). The organic phase was washed twice with sat. aq. NaHCO$_3$, dried (MgSO$_4$) and evaporated. LC-MS (m/z) 286.3 (MH+); $t_R$=1.27 (method C). $^1$H NMR (500 MHz, DMSO-d$_6$): 1.13 (t, J=7.4 Hz, 3H, Me of Et), 1.28 (t, J=7.1 Hz, 3H, Me of EtO), 1.89 (s, 3H, 2-Me), 2.49 (q (overlapping with DMSO), J=7.4 Hz, 2H, CH$_2$ of Et), 4.28 (q, J=7.1 Hz, 2H, CH$_2$ of EtO), 6.28 (s, 1H, C5-H), 7.27 (t, J=7.3 Hz, 2H, two ortho-H of Ph), 7.47 (t, J=7.3 Hz, 1H, para-H of Ph), 7.53 (t, J=7.5 Hz, 2H, two meta-H of Ph).

The following compounds were prepared analogously:

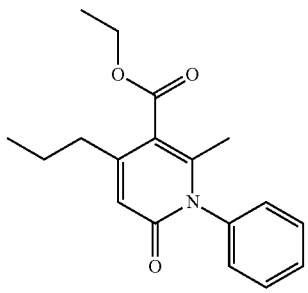

2-Methyl-6-oxo-1-phenyl-4-propyl-1,6-dihydropyridine-3-carboxylic acid ethyl ester LC-MS (m/z) 300.5 (MH+); $t_R$=1.42 (method C). $^1$H NMR (500 MHz, DMSO-d$_6$): 0.92 (t, J=7.3 Hz, 3H, Me of Pr), 1.28 (t, J=7.1 Hz, 3H, Me of EtO), 1.53 (sextet, J=7.5 Hz, 2H, CH$_2$ of Pr), 1.89 (s, 3H, 2-Me), 2.45 (t, J=7.6 Hz, 2H, CH$_2$ of Pr), 4.28 (q, J=7.1 Hz, 2H, CH$_2$ of EtO), 6.27 (s, 1H, C5-H), 7.27 (t, J=7.3 Hz, 2H, two ortho-H of Ph), 7.46 (t, J=7.3 Hz, 1H, para-H of Ph), 7.52 (t, J=7.4 Hz, 2H, two meta-H of Ph).

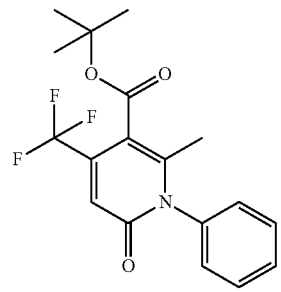

2-Methyl-6-oxo-1-phenyl-4-trifluoromethyl-1,6-dihydro-pyridine-3-carboxylic acid tert-butyl ester The title compound was prepared analogously from 3-phenylamino-but-2-enoic acid tert-butyl ester (500 mg, 2 mmol) and [B]ethyl 4,4,4-trifluoro-2-butynoate (0.12 mL, 0.84 mmol). Yield 177 mg, 60%. LC-MS (m/z) 354.5 (MH$^+$); $t_R$=1.62 (method C).).

$^1$H NMR (500 MHz, DMSO-d$_6$): 1.49 (s, 9H), 1.96 (s, 3H, Me), 6.86 (s, 1H, C5-H), 7.38 (d, J=7.2 Hz, 2H, two ortho-H of Ph), 7.50 (t, J=7.3 Hz, 1H, para-H of Ph), 7.56 (t, J=7.5 Hz, 2H, two meta-H of Ph).

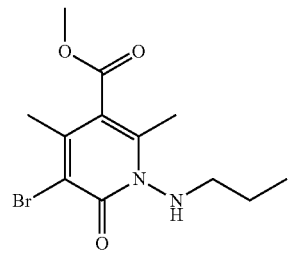

5-Bromo-2,4-dimethyl-6-oxo-1-propylamino-1,6-dihydro-pyridine-3-carboxylic acid methyl ester To a solution of 2,4-dimethyl-6-oxo-1-propylamino-1,6-dihydro-pyridine-3-carboxylic acid methyl ester (1.5 g, 6.3 mmol) in N,N-dimethylformamide (50 mL) N-bromosuccinimide (1.22 g, 6.85 mmol) was added. It was stirred overnight at room temperature then partitioned between water (250 mL) and ethyl acetate (3×100 mL). The combined organic solution was washed with brine (100 mL), dried (MgSO$_4$) and evaporated. The title compound was purified by flash chromatography (yield 1.9 g, 93%). LC-MS (m/z) 317.0 (MH+, $^{79}$Br); $t_R$=1.39 (method C). $^1$H NMR (600 MHz, CDCl$_3$): 1.01 (t, 3H, Me of Pr), 1.62 (sextet, 2H, CH$_2$ of Pr), 2.33 (s, 3H, Me), 2.48 (s, 3H, Me), 2.5-3.1 (very br. coalescing d, 2H, CH$_2$N), 3.90 (s, 3H, OMe), 5.89 (t, J=7.3 Hz, 1H, NH).

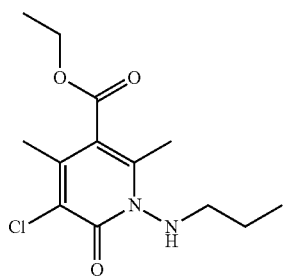

5-Chloro-2,4-dimethyl-6-oxo-1-propylamino-1,6-dihydro-pyridine-3-carboxylic acid ethyl ester The title compound was prepared analogously using N-chlorosuccinimide. Yield 59%. LC-MS (m/z) 289.0 (MH+); $t_R$=0.74 (method B). $^1$H NMR (600 MHz, CDCl$_3$): 5.88 (t, J=7.2 Hz, 1H), 4.37 (q, J=7.1 Hz, 2H), 2.86 (very br., 2H), 2.49 (s, 3H), 2.30 (s, 3H), 1.62 (h, J=7.3 Hz, 2H), 1.39 (t, J=7.2 Hz, 3H), 1.02 (t, J=7.4 Hz, 3H). $^{13}$C NMR (151 MHz, CDCl$_3$): 166.93, 157.93, 144.20, 143.66, 121.78, 113.92, 61.83, 52.87, 21.03, 18.34, 16.36, 14.15, 11.48.

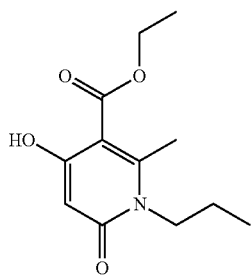

4-Hydroxy-2-methyl-6-oxo-1-propyl-1,6-dihydro-pyridine-3-carboxylic acid ethyl ester Step 1: To a stirred solution of 3-propylamino-but-2-enoic acid ethyl ester (15.99 g, 93.4 mmol) in methylene chloride (300 mL, 4000 mmol) triethylamine (14.3 mL, 103 mmol) was added and the mixture was allowed to cool on ice-water bath. Ethyl malonyl chloride (12.9 mL, 103 mmol) was added dropwise and the mixture was stirred at r.t. for 3 hours then kept in refrigerator overnight. It was diluted with 300 mL water and stirred thoroughly. The organic layer was dried (MgSO$_4$) and evaporated. LC-MS (m/z) 286.4 (MH+); $t_R$=1.28 (method C). The crude product was used in the next step without further purification.

Step 2: Sodium metal pieces (1.96 g, 85.1 mmol) were added to abs. ethanol (500 mL) with caution, followed by the product from step 2 (24.28 g, 85.09 mmol). The obtained mixture was refluxed for 90 min, allowed to cool, diluted with water (4 L) and acidified with 2M HCl to pH 5. Ethanol was evaporated and the remaining aqueous solution was extracted with ethyl acetate (3×300 mL), washed with brine, dried (MgSO$_4$) and evaporated. Flash chromatography afforded 13.4 g, 66% yield. LC-MS (m/z) 240.0 (MH+); $t_R$=0.98 (method C). $^1$H NMR (500 MHz, CD$_3$OD, CHD$_2$OD=3.34 ppm): 0.87 (t, J=7.4 Hz, 3H, Me of Pr), 1.25 (t, J=7.1 Hz, 3H, Me of Et), 1.73 (sextet, J=7.7 Hz, 2H), 2.31 (s, 3H, Me), 3.83 (m, 2H, CH$_2$N), 4.22 (q, J=7.1 Hz, 2H, CH$_2$ of Et), 5.58 (s, 1H, C5-H), 10.89 (s, 1H, OH).

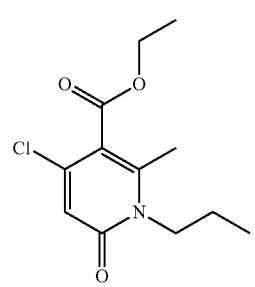

4-Chloro-2-methyl-6-oxo-1-propyl-1,6-dihydro-pyridine-3-carboxylic acid ethyl ester To a mixture of 4-hydroxy-2-methyl-6-oxo-1-propyl-1,6-dihydro-pyridine-3-carboxylic acid ethyl ester (2.00 g, 8.36 mmol) and phosphoryl chloride (4.67 mL, 50.2 mmol), triethylamine (1.16 mL, 8.36 mmol) and methylene chloride (2 mL) were added and the mixture was stirred at r.t. overnight. It was concentrated in vacuo, poured into ice and carefully neutralised with sat.aq. K$_2$CO$_3$ solution. It was extracted with ethyl acetate (3×300 mL), the combined organic solution was washed with brine (20 mL), dried (MgSO$_4$) and evaporated. The title compound was purified by flash chromatography, yield 0.6 g, 30%. LC-MS (m/z) 258.5 (MH+); $t_R$=1.21 (method C).

$^1$H NMR (500 MHz, CD$_3$OD, CHD$_2$OD=3.34 ppm): 1.03 (t, J=7.4 Hz, 3H, Me of Pr), 1.39 (t, J=7.1 Hz, 3H, Me of Et), 1.73 (sextet, J=7.7 Hz, 2H), 2.50 (s, 3H, Me), 4.06 (m, 2H, CH$_2$N), 4.40 (q, J=7.2 Hz, 2H, CH$_2$ of Et), 6.57 (s, 1H, C5-H).

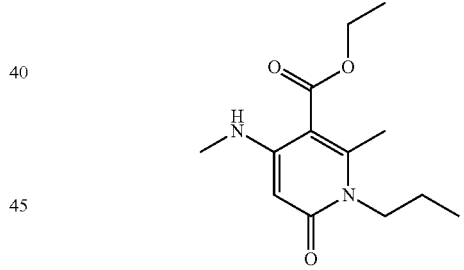

2-Methyl-4-methylamino-6-oxo-1-propyl-1,6-dihydro-pyridine-3-carboxylic acid ethyl ester A mixture of 4-chloro-2-methyl-6-oxo-1-propyl-1,6-dihydro-pyridine-3-carboxylic acid ethyl ester (166 mg, 0.644 mmol), 8 M methylamine in ethanol (0.7 mL) and ethanol (1.3 mL) was heated under microwave irradiation at 150° C. for 10 min and concentrated in vacuo. It was partitioned between ethyl acetate (15 mL) and sat. Na$_2$CO$_3$ (2×3 mL), washed with brine, dried (MgSO$_4$) and evaporated. Yield 108 mg, 66%. LC-MS (m/z) 253.4 (MH+); $t_R$=1.06 (method C). $^1$H NMR (500 MHz, CDCl$_3$): 0.97 (t, J=7.4 Hz, 3H, Me of Pr), 1.37 (t, J=7.1 Hz, 3H, Me of Et), 1.68 (sextet, J=7.7 Hz, 2H), 2.51 (s, 3H, Me), 2.78 (d, J=4.9 Hz, 3H Me-NH), 3.98 (br. t, 2H, CH$_2$N), 4.33 (q, J=7.2 Hz, 2H, CH$_2$ of Et), 5.46 (s, 1H, C5-H), 6.43 (br., 1H, NH-Me).

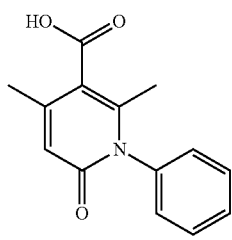

2,4-Dimethyl-6-oxo-1-phenyl-1,6-dihydro-pyridine-3-carboxylic acid

A mixture of 2,4-dimethyl-6-oxo-1-phenyl-1,6-dihydro-pyridine-3-carboxylic acid ethyl ester (108 mg, 0.398 mmol) in methanol (0.8 mL) and 32% aq. NaOH (0.25 mL) was shaken at 60° for 22 hrs (after 5 hours only 70% conversion was observed). The reaction mixture was quenched with water (5 ml), extracted with ether (3×2 ml), and acidified 3M HCl (1 mL, pH=0). The title compound was separated by filtration to give 52.1 mg of colorless solid, yield 54%. LC-MS (m/z) 244.5 (MH+); $t_R$=0.54. $^1$H NMR (600 MHz, DMSO-$d_6$): 1.94 (s, 3H, 2-Me), 2.19 (d, J=0.9 Hz, 3H, 4-Me), 6.29 (s, 1H, 5-H), 7.25 (dm, J=7.7 Hz, J<1.5 Hz, 2H, two ortho-H of Ph), 7.47 (tt, J=7.4 Hz, J=1.2 Hz, 1H, para-H of Ph), 7.53 (tm, J=7.5 Hz, J<1.7 Hz, 2H, two meta-H of Ph), 13.26 (br. s, 1H, CO$_2$H).

The following compounds were obtained analogously:

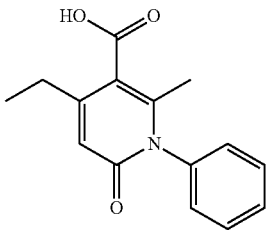

4-Ethyl-2-methyl-6-oxo-1-phenyl-1,6-dihydro-pyridine-3-carboxylic acid

The reaction was not finished after 16 hours at 60° C., then the temperature was increased to 80° C. LC-MS (m/z) 258.5 (MH+); $t_R$=0.77 (method C). $^1$H NMR (500 MHz, DMSO-$d_6$): 1.16 (t, J=7.5 Hz, 3H, Me of Et), 1.92 (s, 3H, 2-Me), 2.54 (q, J=7.4 Hz, 2H, CH$_2$ of Et), 6.27 (s, 1H, C5-H), 7.26 (t, J=7.6 Hz, 2H, two ortho-H of Ph), 7.47 (t, J=7.2 Hz, 1H, para-H of Ph), 7.53 (t, J=7.5 Hz, 2H, two meta-H of Ph).

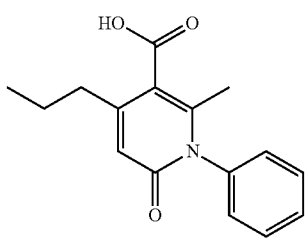

2-Methyl-6-oxo-1-phenyl-4-propyl-1,6-dihydro-pyridine-3-carboxylic acid

The reaction was run at 90° C. for 6 hours. LC-MS (m/z) 272.5 (MH+); $t_R$=0.89 (method C). $^1$H NMR (500 MHz, DMSO-$d_6$): 0.93 (t, J=7.3 Hz, 3H, Me of Pr), 1.57 (sextet, J=7.5 Hz, CH$_2$ of Pr), 1.92 (s, 3H, 2-Me), 2.50 (t (overlapping with DMSO), J=7.5 Hz, 2H, CH$_2$ of Pr), 6.25 (s, 1H, C5-H), 7.26 (d, J=7.5 Hz, 2H, two ortho-H of Ph), 7.46 (t, J=7.2 Hz, 1H, para-H of Ph), 7.53 (t, J=7.6 Hz, 2H, two meta-H of Ph).

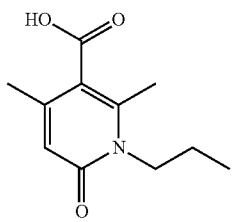

2,4-Dimethyl-6-oxo-1-propyl-1,6-dihydro-pyridine-3-carboxylic acid

LC-MS (m/z) 209.9 (MH+); $t_R$=0.61 (method C).

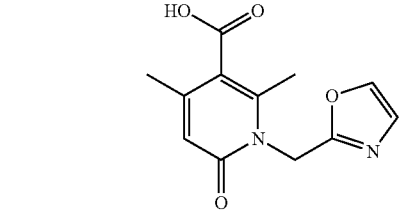

2,4-Dimethyl-1-oxazol-2-ylmethyl-6-oxo-1,6-dihydro-pyridine-3-carboxylic acid

LC-MS (m/z) 249.4 (MH+); $t_R$=0.34 (method C).

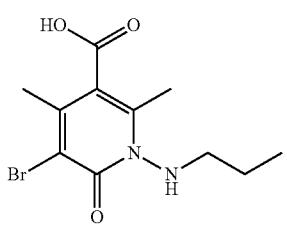

5-Bromo-2,4-dimethyl-6-oxo-1-propylamino-1,6-dihydro-pyridine-3-carboxylic acid

Before acidification the unreacted ester was extracted with ethyl acetate. LC-MS (m/z) 303.3 & 305.0 (MH+); $t_R$=1.07 (method C). $^1$H NMR (600 MHz, D$_2$O, DHO=4.80 ppm): 0.94 (t, 3H, Me of Pr), 1.56 (sextet, 2H, CH$_2$ of Pr), 2.31 (s, 3H, Me), 2.42 (s, 3H, Me), 2.87 (t, 2H, CH$_2$N).

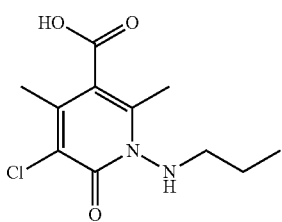

5-Chloro-2,4-dimethyl-6-oxo-1-propylamino-1,6-dihydro-pyridine-3-carboxylic acid Yield 94%. LC-MS (m/z) 259.0 (MH+); $t_R$=0.49 (method B).

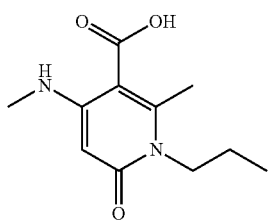

2-Methyl-4-methylamino-6-oxo-1-propyl-1,6-dihydro-pyridine-3-carboxylic acid

Yield 54 mg, 56%. LC-MS (m/z) 225.2 (MH+); $t_R$=0.60 (method C).

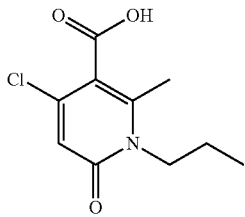

4-Chloro-2-methyl-6-oxo-1-propyl-1,6-dihydro-pyridine-3-carboxylic acid

Yield 178 mg, >98%. LC-MS (m/z) 230.5 (MH+); $t_R$=0.77 (method C).

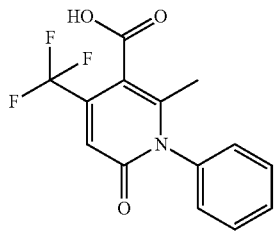

2-Methyl-6-oxo-1-phenyl-4-trifluoromethyl-1,6-dihydro-pyridine-3-carboxylic acid Trifluoroacetic acid (100 uL, 1 mmol) in 1,2-dichloroethane (200 uL, 2 mmol) was added to 2-methyl-6-oxo-1-phenyl-4-trifluoromethyl-1,6-dihydro-pyridine-3-carboxylic acid tert-butyl ester (50 mg, 0.1 mmol). The obtained solution was stirred at r.t. overnight and evaporated. The residue was partitioned between 2M NaOH (4 mL) ethyl acetate (2×2 mL) to remove traces of the unreacted ester. The aqueous phase was acidified and the product extracted with ethyl acetate (2×3 mL). The combined organic solution was washed with brine, dried (MgSO$_4$) and evaporated, yield 19.4 mg, 50%. LC-MS (m/z) 298.4 (MH+); $t_R$=0.80 (method C).). $^1$H NMR (500 MHz, DMSO-d$_6$): 1.99 (s, 3H, Me), 3.56 (br., CO$_2$H+H$_2$O), 6.86 (s, 1H, C5-H), 7.36 (d, J=7.3 Hz, 2H, two ortho-H of Ph), 7.50 (t, J=7.4 Hz, 1H, para-H of Ph), 7.56 (t, J=7.5 Hz, 2H, two meta-H of Ph).

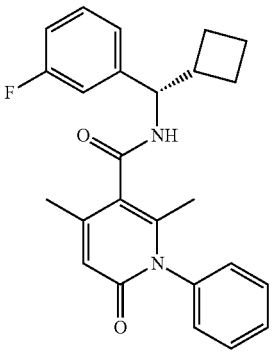

2,4-Dimethyl-6-oxo-1-phenyl-1,6-dihydro-pyridine-3-carboxylic acid [(S)-cyclobutyl-(3-fluoro-phenyl)-methyl]-amide A mixture of 2,4-dimethyl-6-oxo-1-phenyl-1,6-dihydro-pyridine-3-carboxylic acid (52.1 mg, 0.214 mmol), C—[(S)—C-cyclobutyl-C-(3-fluoro-phenyl)]-methylamine hydrochloride (85.9 mg, 0.398 mmol), N-(3-dimethylaminopropyl)-N'-ethylcarbodiimide hydrochloride (=EDC, 76.3 mg, 0.398 mmol), 1-hydroxybenzotriazole (=HOBt, 0.0538 g, 0.398 mmol) in N,N-dimethylformamide (4 mL) was stirred for 5 min followed by addition of N,N-diisopropylethylamine (0.200 mL, 1.15 mmol). It was stirred at ambient temperature for 17 hours. The reaction mixture was poured into 3M HCl (10 ml) with ice, allowed to stir for 10 min, filtered, washed with water and dried in vacuo to give 60 mg of the title compound as a colourless solid, yield 37%. LC-MS (m/z) 405.4 (MH+); $t_R$=1.38. $^1$H NMR (600 MHz, DMSO-d$_6$): 1.64-1.87 (m, 8H), 2.01 (br. m, 4H), 2.58 (m, 1H, CH of Cb), 4.89 (dd, J=9.0 Hz, J=9.8 Hz, CH—N), 6.26 (s, 1H, C5-H), 7.04 (dt, J(t)=8.5 Hz, J(d)=2.2 Hz, 1H), 7.13-7.2 (m, 4H), 7.35 (q (unres. Dt), J(t)=7.8 Hz, J(d)=6.2 Hz, 1H), 7.46 (tt, J=7.4 Hz, J=1.0 Hz, 1H, para-H of Ph), 7.53 (m, 2H, two meta-H of Ph), 8.88 (d, J=8.6 Hz, 1H, NH).

The following compounds were obtained analogously:

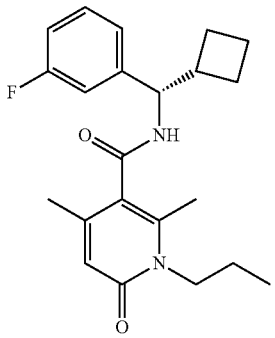

2,4-Dimethyl-6-oxo-1-propyl-1,6-dihydro-pyridine-3-carboxylic acid [(S)-cyclobutyl-(3-fluoro-phenyl)-methyl]-amide The title compound was purified by preparative LC-MS. LC-MS (m/z) 371.3 (MH+); $t_R$=1.49 (method C).

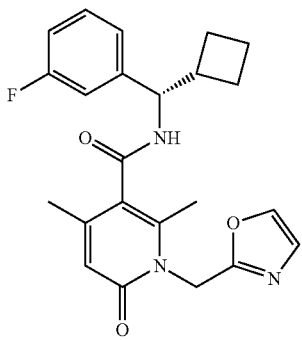

2,4-Dimethyl-1-oxazol-2-ylmethyl-6-oxo-1,6-dihydro-pyridine-3-carboxylic acid [(S)-cyclobutyl-(3-fluoro-phenyl)-methyl]-amide The title compound was purified by preparative LC-MS. LC-MS (m/z) 410.5 (MH+); $t_R$=1.37 (method C).

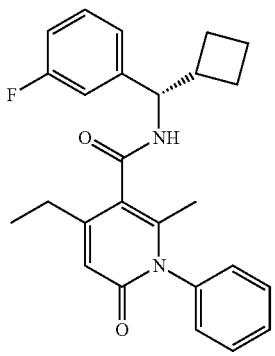

4-Ethyl-2-methyl-6-oxo-1-phenyl-1,6-dihydro-pyridine-3-carboxylic acid [(S)-cyclobutyl-(3-fluoro-phenyl)-methyl]-amide LC-MS (m/z) 419.7 (MH+); $t_R$=1.59 (method C). $^1$H NMR (500 MHz, DMSO-$d_6$): 1.08 (br., 3H, Me of Et), 1.59-1.88 (br., 8H), 2.03 (br., 1H), 2.36 (br., 2H, CH$_2$ of Et), 2.60 (m, 1H, CH of Cb), 4.90 (t (unresolved dd), J=9.4 Hz, CH—N), 6.24 (s, 1H, C5-H), 7.04 (br. t, J(t)=7.8 Hz, 1H), 7.11-7.23 (br. m, 4H), 7.34 (br. q), J=7 Hz, 1H), 7.46 (t, J=7.4 Hz, 1H, para-H of Ph), 7.53 (br. m, 2H, two meta-H of Ph), 8.88 (d, J=8.5 Hz, 1H, NH).

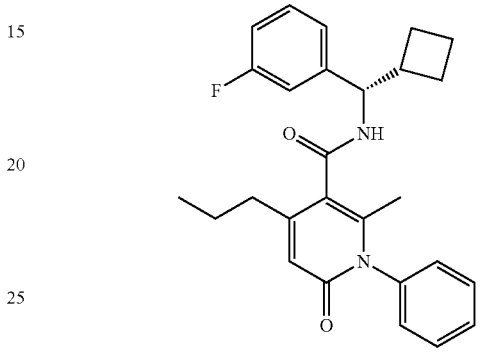

2-Methyl-6-oxo-1-phenyl-4-propyl-1,6-dihydro-pyridine-3-carboxylic acid [(S)-cyclobutyl-(3-fluoro-phenyl)-methyl]-amide LC-MS (m/z) 433.5 (MH+); $t_R$=1.66 (method C).

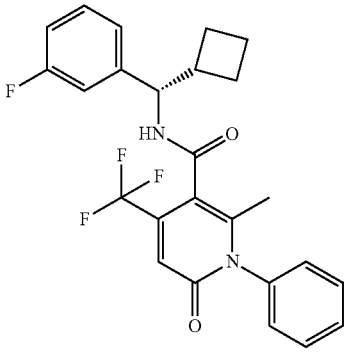

2-Methyl-6-oxo-1-phenyl-4-trifluoromethyl-1,6-dihydro-pyridine-3-carboxylic acid [(S)-cyclobutyl-(3-fluoro-phenyl)-methyl]-amide A mixture of 2-methyl-6-oxo-1-phenyl-4-trifluoromethyl-1,6-dihydro-pyridine-3-carboxylic acid (102 mg, 0.343 mmol), C—[(S)—C-cyclobutyl-C-(3-fluoro-phenyl)]-methylamine (95 mg, 0.53 mmol, generated from its HCl salt), 1-hydroxybenzotriazole (70 mg, 0.5 mmol), N-(3-dimethylaminopropyl)-N'-ethylcarbodiimide hydrochloride (100 mg, 0.5 mmol), and N,N-diisopropylethylamine (0.180 mL, 1.0 mmol) in tetrahydrofuran (10 mL) was stirred at r.t. overnight, then evaporated. It was purified by flash chromatography and the title compound was eluted with 80% ethyl acetate in heptane to yield 11 mg. LC-MS (m/z) 459.6 (MH+); $t_R$=1.61 (method C).

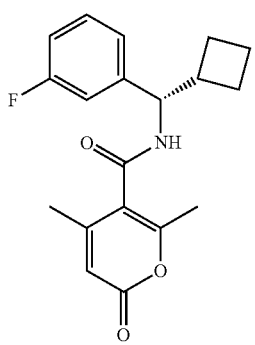

2,4-Dimethyl-6-oxo-6H-pyran-3-carboxylic acid [(S)-cyclobutyl-(3-fluoro-phenyl)-methyl]-amide Prepared from isodehydroacetic acid, yield 33%. LC-MS (m/z) 330.4 (MH$^+$); $t_R$=1.37. $^1$H NMR (500 MHz, CDCl$_3$): 7.35-7.27 (m, 1H), 7.21 (d, J=8.6 Hz, 1H), 7.14 (d, J=7.7 Hz, 1H), 7.06 (d, J=9.7 Hz, 1H), 6.97 (td, J=8.3, 2.1 Hz, 1H), 5.84 (s, 1H), 5.03 (t, J=9.4 Hz, 1H), 2.81-2.68 (m, 1H), 2.25-2.13 (m, 4H), 2.06 (s, 3H), 2.02-1.72 (m, 5H). $^{13}$C NMR (126 MHz, CDCl$_3$): 164.72, 164.12, 162.23, 159.66, 155.40, 143.50 (d, J=6.5 Hz), 130.37 (d, J=8.1 Hz), 122.81, 117.97, 114.64 (d, J=21.1 Hz), 113.90 (d, J=21.7 Hz), 111.17, 58.91, 40.14, 26.19, 25.78, 19.78, 18.39, 17.67.

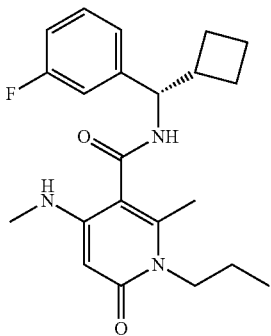

5-Bromo-2-methyl-4-methylamino-6-oxo-1-propyl-1,6-dihydro-pyridine-3-carboxylic acid [(S)-cyclobutyl-(3-fluoro-phenyl)-methyl]-amide 2-Methyl-4-methylamino-6-oxo-1-propyl-1,6-dihydro-pyridine-3-carboxylic acid (54 mg, 0.24 mmol) was dissolved in N,N-dimethylformamide (8 mL). C—[(S)—C-Cyclobutyl-C-(3-fluoro-phenyl)]-methylamine hydrochloride (51.9 mg) was added and the mixture was cooled on an ice/water bath. N,N-Diisopropylethylamine (0.21 mL, 1.2 mmol) was added followed by HATU (=2-(7-aza-1H-benzotriazole-1-yl)-1,1,3,3-tetramethyluronium hexafluorophosphate, 91.6 mg, 0.241 mmol). It was stirred at r.t. for 3 hrs and partitioned between water (50 mL) and ethyl acetate (3×50 mL). The combined organic solution was washed with brine, dried over MgSO$_4$ and evaporated. The title compound was purified by flash chromatography, yield 67 mg, 72%. LC-MS (m/z) 386.3 (MH+); $t_R$=1.57 (method C). $^1$H NMR (500 MHz, DMSO-d$_6$): 0.87 (t, J=7.4 Hz, 3H), 1.51 (sextet, J=7.8 Hz, 2H), 1.73 (m, 2H), 1.79 (m, 2H), 1.91 (m, 1H), 2.00 (br. m, 1H), 2.15 (s, 3H, Me), 2.60 (overlapping d, J=4.8 Hz, 3H Me-NH), 2.60 (m, 1H, CH of Cb), 3.76 (dd, J=6.6, 9.1 Hz, 2H, CH$_2$N), 4.90 (dd, J=8.8, 9.9 Hz, 1H, CH—N), 5.14 (s, 1H, C5-H), 5.42 (q, J=4.8 Hz, 1H, NH-Me), 7.06 (dt, J(t)=8.4 Hz, J(d)=2.6 Hz, 1H), 7.14 (overlapping m, 1H), 7.16 (overlapping d, J=8.5 Hz, 1H), 7.37 (dt, J(d)=6.3 Hz, J(t)=8 Hz, 1H), 8.77 (d, J=8.4 Hz, 1H, NHCO).

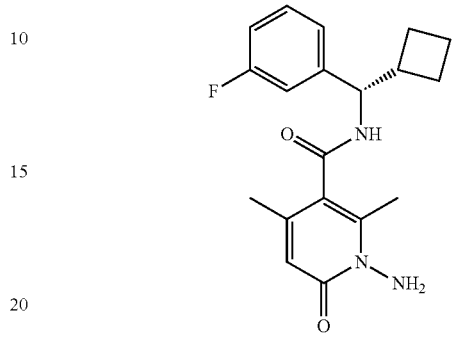

1-Amino-2,4-dimethyl-6-oxo-1,6-dihydro-pyridine-3-carboxylic acid [(S)-cyclobutyl-(3-fluoro-phenyl)-methyl]-amide To a solution of 2,4-dimethyl-6-oxo-6H-pyran-3-carboxylic acid [(S)-cyclobutyl-(3-fluoro-phenyl)-methyl]-amide (419 mg, 1.27 mmol) in ethanol (4.0 mL, 70 mmol) were added hydrazine hydrate (370 uL, 7.6 mmol) and acetic acid (4.0 mL, 70 mmol). The mixture was heated at 80° C. for 24 hrs. More hydrazine hydrate (371 uL, 7.63 mmol) was added and stirring continued for 7 hrs. The reaction mixture was adjusted to neutral pH by addition of aq. Sat. Na$_2$CO$_3$. The crude mixture was extracted with dichloromethane (4×40 mL), combined organic phases were washed with brine, dried over MgSO$_4$ and evaporated. The residue was purified by flash chromatography to give the title compound, yield 33%. LC-MS (m/z) 344.4 (MH$^+$); $t_R$=1.32 (method C). $^1$H NMR (600 MHz, CDCl$_3$): 7.84 (d, J=8.6 Hz, 1H), 7.34 (td, J=7.9, 6.0 Hz, 1H), 7.20 (d, J=7.7 Hz, 1H), 7.17-7.11 (m, 1H), 6.99 (td, J=8.3, 2.0 Hz, 1H), 6.02 (s, 1H), 5.22 (s, 2H), 5.11-5.02 (m, 1H), 2.87-2.75 (m, 1H), 2.29 (s, 3H), 2.24 (m, 1H), 2.05 (s, 3H), 2.00-1.75 (m, 5H). $^{13}$C NMR (151 MHz, CDCl$_3$) 166.34, 162.14, 159.96, 146.98, 143.64, 142.71, 130.10 (d, J=8.2 Hz, 1C), 122.78, 118.63, 114.34 (d, J=21.0 Hz, 1C), 114.14, 113.79 (d, J=21.6 Hz, 1C), 58.74, 40.05, 26.17, 25.59, 19.48, 17.49, 16.63.

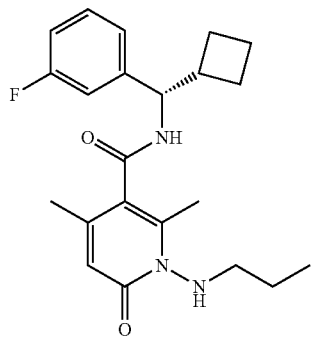

2,4-Dimethyl-6-oxo-1-propylamino-1,6-dihydro-pyridine-3-carboxylic acid [(S)-cyclobutyl-(3-fluoro-phenyl)-methyl]-amide To a mixture of 1-amino-2,4-dimethyl-6-oxo-1,6-dihydro-pyridine-3-carboxylic acid [(S)-cyclobutyl-(3-fluoro-phenyl)-methyl]-amide (415 mg, 1.21 mmol), propionaldehyde (0.52 mL, 7.3 mmol) and acetic acid (0.5 mL, 9 mmol) in methanol (10 mL) was added sodium cyanoborohydride (0.27 g, 4.2 mmol) and the mixture was stirred under argon atmosphere for 3 days at room temperature. The crude reaction mixture was concentrated in vacuo, diluted with $H_2O$ (30 mL) and extracted with dichloromethane (3×30 mL). The combined organic phases were washed with brine, dried over $MgSO_4$ and evaporated. The crude mixture was purified by flash chromatography, yield 34%. LC-MS (m/z) 386.5 (MH+); $t_R$=1.63 (method C).

The following compound was prepared analogously:

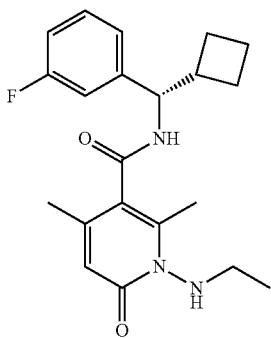

1-Ethylamino-2,4-dimethyl-6-oxo-1,6-dihydro-pyridine-3-carboxylic acid [(S)-cyclobutyl-(3-fluoro-phenyl)-methyl]-amide Yield 57%. LC-MS (m/z) 372.4 (MH+); $t_R$=1.51 (method C).

EXAMPLES

Example 1

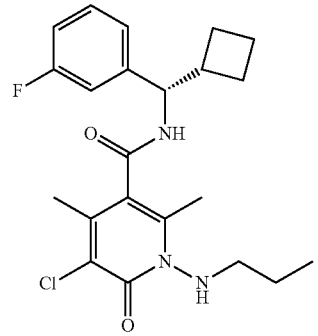

1a 5-Chloro-2,4-dimethyl-6-oxo-1-propylamino-1,6-dihydro-pyridine-3-carboxylic acid [(S)-cyclobutyl-(3-fluoro-phenyl)-methyl]-amide To an ice cold mixture of 5-chloro-2,4-dimethyl-6-oxo-1-propylamino-1,6-dihydro-pyridine-3-carboxylic acid (48 mg, 0.18 mmol), C—[(S)—C-cyclobutyl-C-(3-fluoro-phenyl)]-methylamine hydrochloride (30 mg, 0.14 mmol), 1-hydroxybenzotriazole (25 mg, 0.19 mmol) and N-(3-dimethylaminopropyl)-N'-ethylcarbodiimide hydrochloride (36 mg, 0.19 mmol) in tetrahydrofuran (2 mL, 20 mmol) was slowly added N,N-diisopropylethylamine (0.130 mL, 0.744 mmol). The reaction was allowed to warm to RT and stirred overnight. The reaction mixture was poured into $H_2O$ (20 mL) and extracted with ethylacetate (3×20 mL), the combined organic phases were washed with brine, dried over $MgSO_4$ and evaporated. The title compound was purified by flash chromatography, yield 41%. LC-MS (m/z) 420.5 (MH+); $t_R$=1.71 (method C).

Table 2. The following compounds were prepared analogously from the corresponding acids and amines. The products were separated by preparative LC-MS. For analytical LC-MS method C has been used for all the compounds. For all the compounds containing Cl or Br, the corresponding isotope distributions (e.g. ca. 1:1 for $^{79}$Br and $^{81}$Br or ca. 3:1 for $^{35}$Cl and $^{37}$Cl) were observed. However, in the table below, the m/z ratio is reported only for the most intensive molecular ion peak:

| | Chemical name | Structure | $t_R$ (min) | MW | m/z (MH+) |
|---|---|---|---|---|---|
| 1a | 5-Chloro-2,4-dimethyl-6-oxo-1-propylamino-1,6-dihydro-pyridine-3-carboxylic acid [(S)-cyclobutyl-(3-fluoro-phenyl)-methyl]-amide | 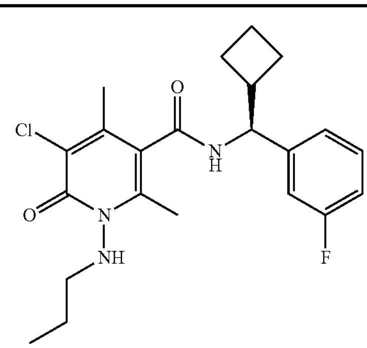 | 1.71 | 419.93 | 420.5 |

| | Chemical name | Structure | $t_R$ (min) | MW | m/z (MH⁺) |
|---|---|---|---|---|---|
| 1b | 5-Bromo-2,4-dimethyl-6-oxo-1-propylamino-1,6-dihydro-pyridine-3-carboxylic acid [(S)-cyclopropyl-(4-fluoro-phenyl)-methyl]-amide | 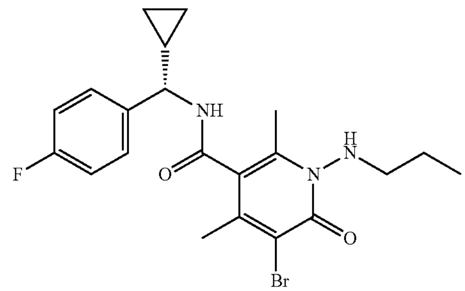 | 1.59 | 450.35 | 450.1 |
| 1c | 5-Bromo-2,4-dimethyl-6-oxo-1-propylamino-1,6-dihydro-pyridine-3-carboxylic acid [(S)-(3-chloro-phenyl)-cyclopropyl-methyl]-amide | 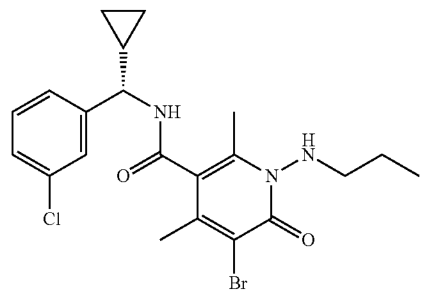 | 1.7 | 466.80 | 468.3 |
| 1d | 5-Bromo-2,4-dimethyl-6-oxo-1-propylamino-1,6-dihydro-pyridine-3-carboxylic acid [(S)-(4-chloro-phenyl)-cyclopropyl-methyl]-amide | 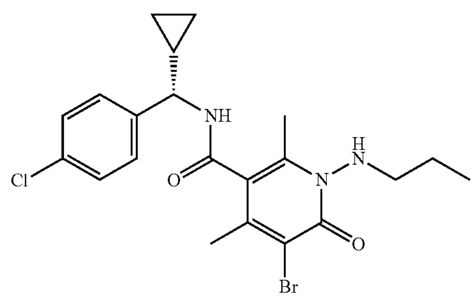 | 1.72 | 466.80 | 468.5 |
| 1e | 5-Bromo-2,4-dimethyl-6-oxo-1-propylamino-1,6-dihydro-pyridine-3-carboxylic acid [(S)-1-(2-fluoro-phenyl)-propyl]-amide | 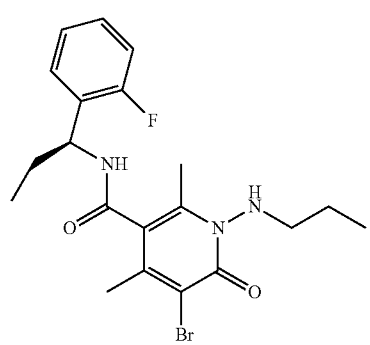 | 1.55 | 438.34 | 440.2 |
| 1f | 5-Bromo-2,4-dimethyl-6-oxo-1-propylamino-1,6-dihydro-pyridine-3-carboxylic acid [(S)-1-(3-fluoro-phenyl)-propyl]-amide | 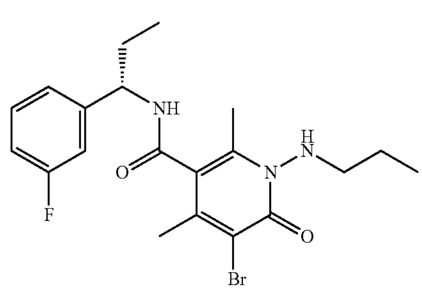 | 1.58 | 438.34 | 440.2 |

-continued

| | Chemical name | Structure | t$_R$ (min) | MW | m/z (MH$^+$) |
|---|---|---|---|---|---|
| 1g | 5-Bromo-2,4-dimethyl-6-oxo-1-propylamino-1,6-dihydro-pyridine-3-carboxylic acid [(S)-1-(4-fluoro-phenyl)-propyl]-amide | 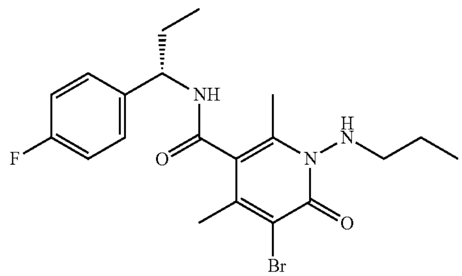 | 1.57 | 438.34 | 440.1 |
| 1h | 5-Bromo-2,4-dimethyl-6-oxo-1-propylamino-1,6-dihydro-pyridine-3-carboxylic acid ((S)-2-methyl-1-phenyl-propyl)-amide | 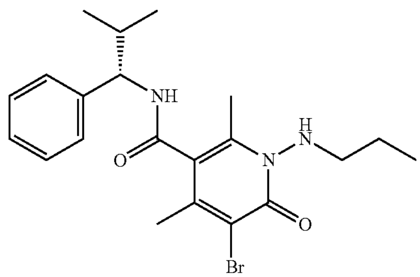 | 1.63 | 434.38 | 434.4 |
| 1i | 5-Bromo-2,4-dimethyl-6-oxo-1-propylamino-1,6-dihydro-pyridine-3-carboxylic acid ((S)-cyclobutyl-phenyl-methyl)-amide | 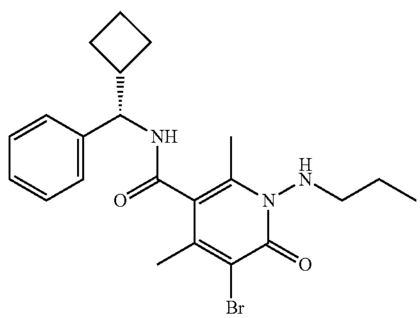 | 1.68 | 446.39 | 446.6 |
| 1j | 5-Bromo-2,4-dimethyl-6-oxo-1-propylamino-1,6-dihydro-pyridine-3-carboxylic acid ((S)-cyclopentyl-phenyl-methyl)-amide | 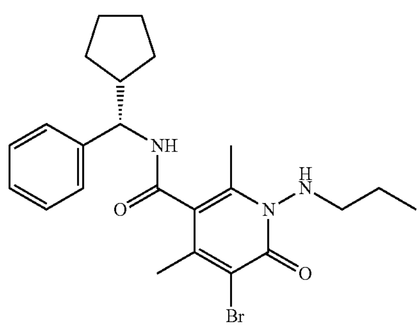 | 1.78 | 460.41 | 460.7 |
| 1k | 5-Bromo-2,4-dimethyl-6-oxo-1-propylamino-1,6-dihydro-pyridine-3-carboxylic acid [(S)-cyclobutyl-(4-fluoro-phenyl)-methyl]-amide | 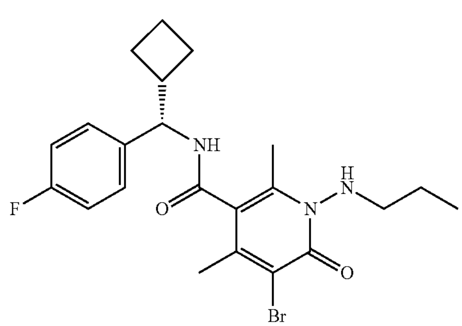 | 1.72 | 464.38 | 466.2 |

-continued

| | Chemical name | Structure | $t_R$ (min) | MW | m/z (MH⁺) |
|---|---|---|---|---|---|
| 1l | 5-Bromo-2,4-dimethyl-6-oxo-1-propylamino-1,6-dihydro-pyridine-3-carboxylic acid [(S)-cyclopropyl-(3-fluoro-phenyl)-methyl]-amide | 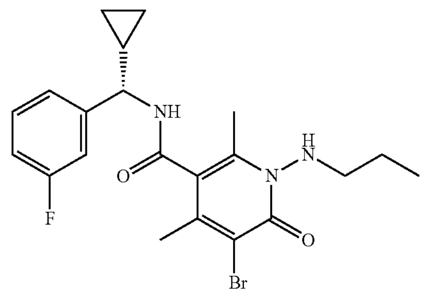 | 1.6 | 450.35 | 450.2 |
| 1m | 5-Bromo-2,4-dimethyl-6-oxo-1-propylamino-1,6-dihydro-pyridine-3-carboxylic acid ((S)-cyclopropyl-phenyl-methyl)-amide | 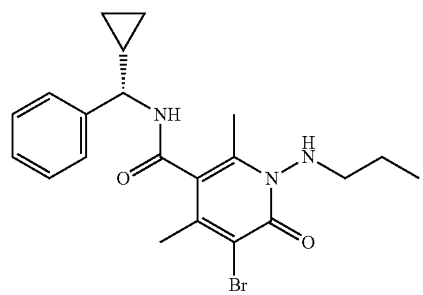 | 1.56 | 432.36 | 434.4 |
| 1n | 5-Bromo-2,4-dimethyl-6-oxo-1-propylamino-1,6-dihydro-pyridine-3-carboxylic acid [(S)-1-(4-chloro-phenyl)-propyl]-amide | 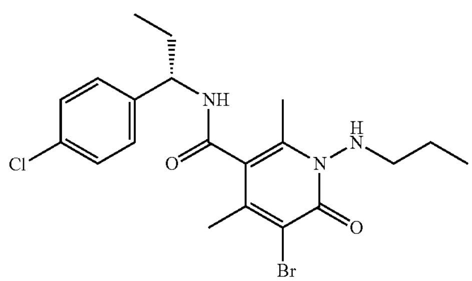 | 1.7 | 454.79 | 456.2 |
| 1o | 5-Bromo-2,4-dimethyl-6-oxo-1-propylamino-1,6-dihydro-pyridine-3-carboxylic acid [(S)-1-(3-chloro-phenyl)-propyl]-amide | 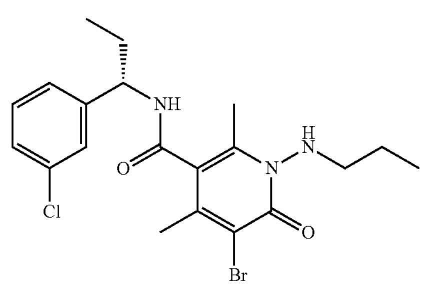 | 1.69 | 454.79 | 456.2 |
| 1p | 5-Bromo-2,4-dimethyl-6-oxo-1-propylamino-1,6-dihydro-pyridine-3-carboxylic acid ((S)-cyclohexyl-phenyl-methyl)-amide | 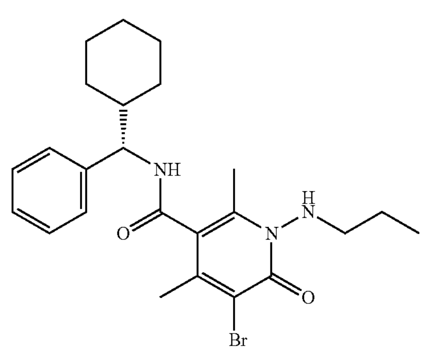 | 1.86 | 474.44 | 476.4 |

-continued

| | Chemical name | Structure | $t_R$ (min) | MW | m/z (MH+) |
|---|---|---|---|---|---|
| 1q | 5-Bromo-2,4-dimethyl-6-oxo-1-propylamino-1,6-dihydro-pyridine-3-carboxylic acid ((S)-1-phenyl-propyl)-amide | 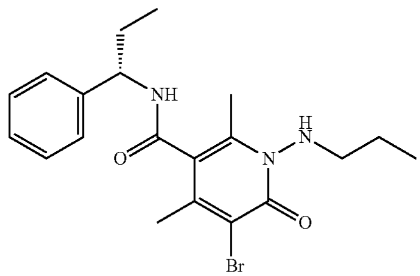 | 1.54 | 420.35 | 420.4 |
| 1r | 5-Bromo-2,4-dimethyl-6-oxo-1-propyl-1,6-dihydro-pyridine-3-carboxylic acid [(S)-cyclopropyl-(4-fluoro-phenyl)-methyl]-amide | 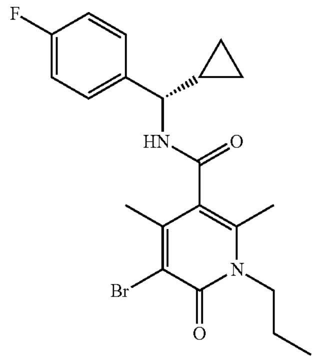 | 1.45 | 435.33 | 435.4 |
| 1s | 5-Bromo-2,4-dimethyl-6-oxo-1-propyl-1,6-dihydro-pyridine-3-carboxylic acid [(S)-(2-chloro-phenyl)-cyclopropyl-methyl]-amide | 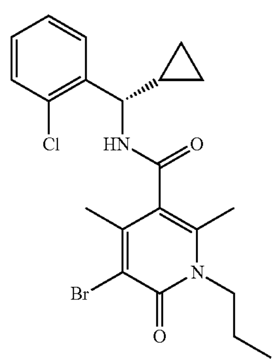 | 1.51 | 451.79 | 453.3 |
| 1t | 5-Bromo-2,4-dimethyl-6-oxo-1-propyl-1,6-dihydro-pyridine-3-carboxylic acid [(S)-(3-chloro-phenyl)-cyclopropyl-methyl]-amide | 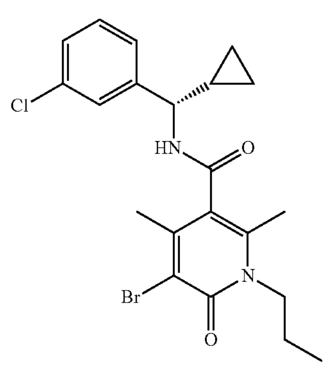 | 1.57 | 451.79 | 453.3 |

| | Chemical name | Structure | $t_R$ (min) | MW | m/z (MH⁺) |
|---|---|---|---|---|---|
| 1u | 5-Bromo-2,4-dimethyl-6-oxo-1-propyl-1,6-dihydro-pyridine-3-carboxylic acid [(S)-(4-chloro-phenyl)-cyclopropyl-methyl]-amide | 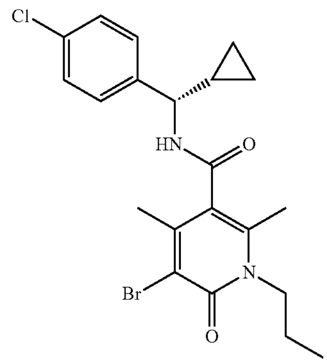 | 1.59 | 451.79 | 453.3 |
| 1v | 5-Bromo-2,4-dimethyl-6-oxo-1-propyl-1,6-dihydro-pyridine-3-carboxylic acid [(S)-1-(2-fluoro-phenyl)-propyl]-amide | 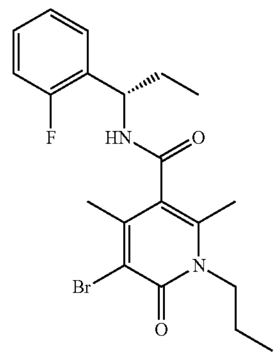 | 1.41 | 423.32 | 423.2 |
| 1w | 5-Bromo-2,4-dimethyl-6-oxo-1-propyl-1,6-dihydro-pyridine-3-carboxylic acid [(S)-1-(3-fluoro-phenyl)-propyl]-amide | 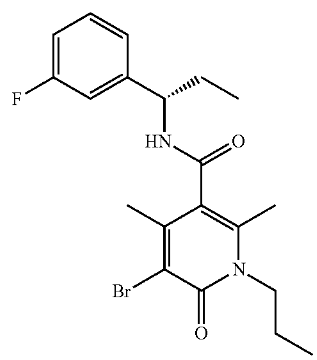 | 1.43 | 423.32 | 423.2 |
| 1x | 5-Bromo-2,4-dimethyl-6-oxo-1-propyl-1,6-dihydro-pyridine-3-carboxylic acid [(S)-1-(4-fluoro-phenyl)-propyl]-amide | 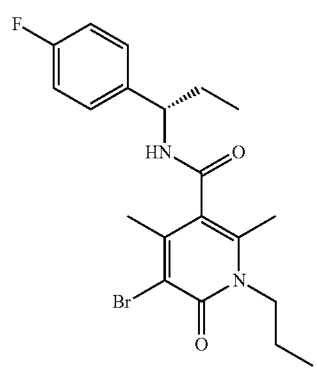 | 1.44 | 423.32 | 423.2 |

-continued

| | Chemical name | Structure | $t_R$ (min) | MW | m/z (MH+) |
|---|---|---|---|---|---|
| 1y | 5-Bromo-2,4-dimethyl-6-oxo-1-propyl-1,6-dihydro-pyridine-3-carboxylic acid ((S)-2-methyl-1-phenyl-propyl)-amide | 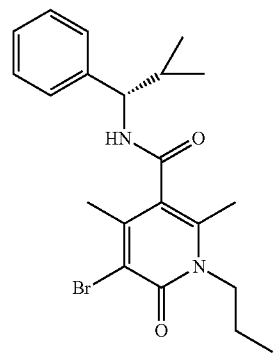 | 1.5 | 419.36 | 421.2 |
| 1z | 5-Bromo-2,4-dimethyl-6-oxo-1-propyl-1,6-dihydro-pyridine-3-carboxylic acid ((S)-cyclobutyl-phenyl-methyl)-amide | 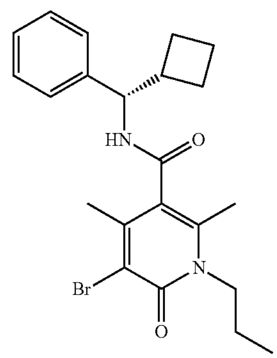 | 1.56 | 431.37 | 431.3 |
| 1aa | 5-Bromo-2,4-dimethyl-6-oxo-1-propyl-1,6-dihydro-pyridine-3-carboxylic acid ((S)-cyclopentyl-phenyl-methyl)-amide | 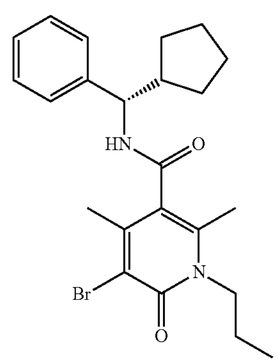 | 1.67 | 445.40 | 445.6 |
| 1ab | 5-Bromo-2,4-dimethyl-6-oxo-1-propyl-1,6-dihydro-pyridine-3-carboxylic acid [cyclobutyl-(2-fluoro-phenyl)-methyl]-amide | 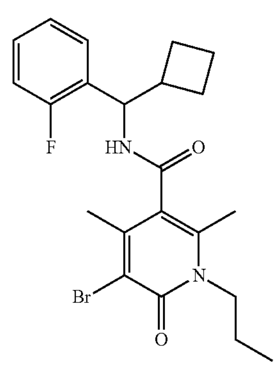 | 1.57 | 449.36 | 449.3 |

-continued

| | Chemical name | Structure | $t_R$ (min) | MW | m/z (MH+) |
|---|---|---|---|---|---|
| 1ac | 5-Bromo-2,4-dimethyl-6-oxo-1-propyl-1,6-dihydro-pyridine-3-carboxylic acid [(S)-cyclobutyl-(4-fluoro-phenyl)-methyl]-amide | 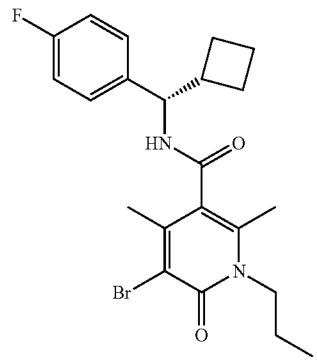 | 1.6 | 449.36 | 449.3 |
| 1ad | 5-Bromo-2,4-dimethyl-6-oxo-1-propyl-1,6-dihydro-pyridine-3-carboxylic acid [(S)-cyclopropyl-(3-fluoro-phenyl)-methyl]-amide | 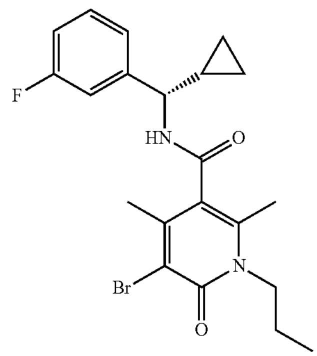 | 1.45 | 435.33 | 435.5 |
| 1ae | 5-Bromo-2,4-dimethyl-6-oxo-1-propyl-1,6-dihydro-pyridine-3-carboxylic acid ((S)-cyclopropyl-phenyl-methyl)-amide | 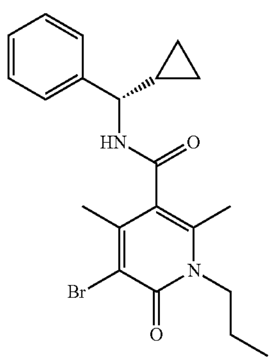 | 1.41 | 417.34 | 417.4 |
| 1af | 5-Bromo-2,4-dimethyl-6-oxo-1-propyl-1,6-dihydro-pyridine-3-carboxylic acid [(S)-1-(4-chloro-phenyl)-propyl]-amide | 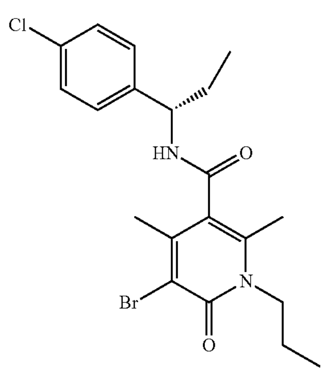 | 1.58 | 439.78 | 441.0 |

| Chemical name | | Structure | t_R (min) | MW | m/z (MH+) |
|---|---|---|---|---|---|
| 1ag | 5-Bromo-2,4-dimethyl-6-oxo-1-propyl-1,6-dihydro-pyridine-3-carboxylic acid [(S)-1-(3-chloro-phenyl)-propyl]-amide | 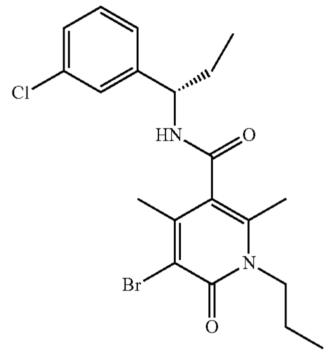 | 1.56 | 439.79 | 441.1 |
| 1ah | 5-Bromo-2,4-dimethyl-6-oxo-1-propyl-1,6-dihydro-pyridine-3-carboxylic acid ((S)-1-phenyl-propyl)-amide | 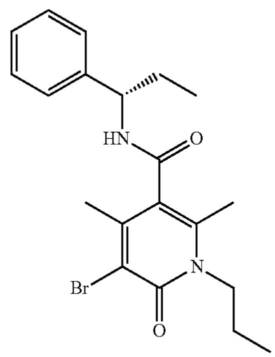 | 1.39 | 405.33 | 405.4 |
| 1ai | 5-Bromo-2,4-dimethyl-6-oxo-1-propyl-1,6-dihydro-pyridine-3-carboxylic acid [(S)-cyclobutyl-(3,4-difluoro-phenyl)-methyl]-amide | 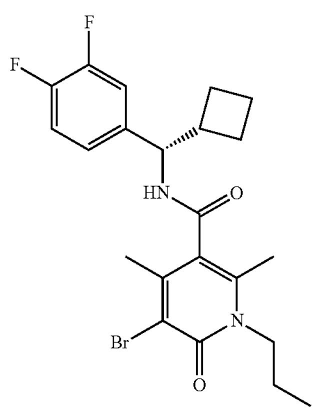 | 1.65 | 467.35 | 467.2 |
| 1aj | 5-Bromo-2,4-dimethyl-6-oxo-1-propyl-1,6-dihydro-pyridine-3-carboxylic acid ((S)-cyclohexyl-phenyl-methyl)-amide | 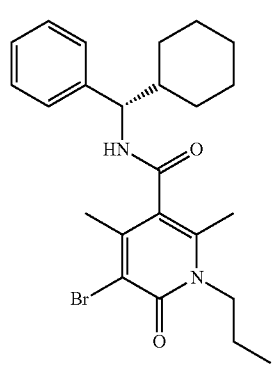 | 1.76 | 459.42 | 461.5 |

-continued

| | Chemical name | Structure | $t_R$ (min) | MW | m/z (MH$^+$) |
|---|---|---|---|---|---|
| 1ak | 5-Bromo-2,4-dimethyl-6-oxo-1-propyl-1,6-dihydro-pyridine-3-carboxylic acid [(S)-cyclobutyl-(3,5-difluoro-phenyl)-methyl]-amide | 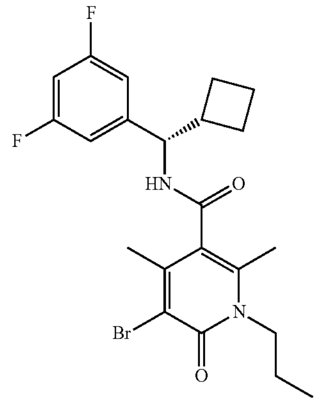 | 1.66 | 467.35 | 467.2 |
| 1al | 5-Bromo-2,4-dimethyl-6-oxo-1-propyl-1,6-dihydro-pyridine-3-carboxylic acid [(S)-cyclopropyl-(3,4-difluoro-phenyl)-methyl]-amide | 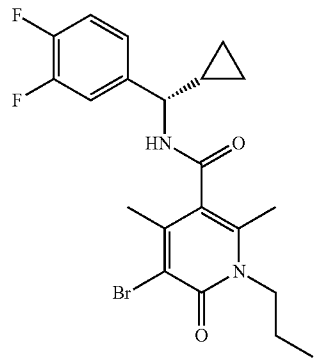 | 1.51 | 453.32 | 453.3 |
| 1am | 5-Bromo-2,4-dimethyl-6-oxo-1-propyl-1,6-dihydro-pyridine-3-carboxylic acid [(R)-cyclopropyl-(3-fluoro-phenyl)-methyl]-amide | 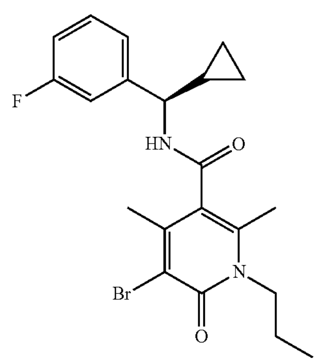 | 1.45 | 435.33 | 435.5 |

1an 4-Chloro-2-methyl-6-oxo-1-propyl-1,6-dihydro-pyridine-3-carboxylic acid [(S)-cyclobutyl-(3-fluoro-phenyl)-methyl]-amide

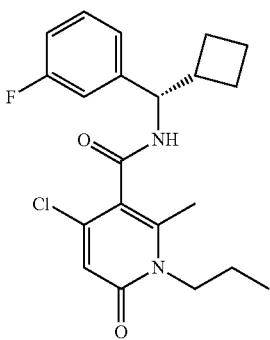

4-Chloro-2-methyl-6-oxo-1-propyl-1,6-dihydro-pyridine-3-carboxylic acid (170 mg, 0.74 mmol) was dissolved in N,N-dimethylformamide (24 mL). C—[(S)—C-Cyclobutyl-C-(3-fluoro-phenyl)]-methylamine hydrochloride (160 mg, 0.74 mmol) was added and the mixture was cooled on an ice/water bath. N,N-Diisopropylethylamine (0.650 mL, 3.7 mmol) was added followed by HATU (=2-(7-aza-1H-benzotriazole-1-yl)-1,1,3,3-tetramethyluronium hexafluorophosphate, 281 mg, 0.74 mmol). The mixture was stirred at room temperature for 2 hours and partitioned between water (30 mL) and ethyl acetate (3×20 mL). The combined organic solution was washed with brine, dried over MgSO$_4$ and evaporated. The title compound was purified by flash chromatography, yield 225 mg, 78%. LC-MS (m/z) 391.5 (MH+); $t_R$=1.71 (method C).

Example 2

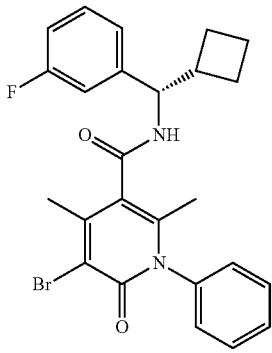

2a 5-Bromo-2,4-dimethyl-6-oxo-1-phenyl-1,6-dihydro-pyridine-3-carboxylic acid [(S)-cyclobutyl-(3-fluoro-phenyl)-methyl]-amide.

A mixture of 2,4-dimethyl-6-oxo-1-phenyl-1,6-dihydro-pyridine-3-carboxylic acid [(S)-cyclobutyl-(3-fluoro-phenyl)-methyl]-amide (11.8 mg, 0.0292 mmol) and N-bromo-succinimide (5.7 mg, 0.032 mmol) in N,N-dimethylformamide (0.2 mL) was shaken at 40° C. for 30 min. It was quenched and shaken with diluted aq. HCl (ca 0.1 M, 4 ml) then filtered to give the title compound as colourless solid (9.0 mg, 64% yield). LC-MS (m/z) 483.2 & 485.3 (MH+); $t_R$=1.54. $^1$H NMR (T=+70° C., 500 MHz, DMSO-$d_6$, DMSO-$d_5$=2.50 ppm): 1.75 (overlapping s, 3H, Me), 1.72-1.93 (overlapping m, 5H), 2.07 (br. m, 1H), 2.2 (s, 3H, Me), 2.67 (m, 1H, CH of Cb), 4.93 (t, J=9.2 Hz, CH—N), 7.02 (dt, J(t)=8.3 Hz, J(d)=1.9 Hz, 1H), 7.13 (br. d, J=10.1 Hz, 1H), 7.17 (d, J=7.5 Hz, 1H), 7.22 (br. m, 2H, Ph), 7.35 (q (unres. Dt), J(t)=7.6 Hz, J(d)=6.6 Hz, 1H), 7.49 (t, J=7.3 Hz, 1H, para-H of Ph), 7.55 (t, J=6.8 Hz, 2H, two meta-H of Ph), 8.68 (d, J=8.3 Hz, 1H, NH).

The following compounds were prepared analogously:

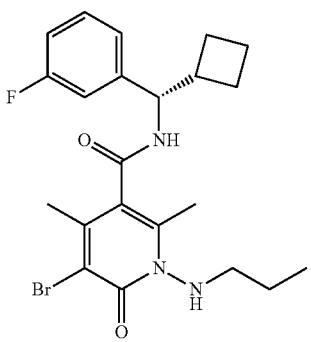

2b 5-Bromo-2,4-dimethyl-6-oxo-1-propylamino-1,6-dihydro-pyridine-3-carboxylic acid [(S)-cyclobutyl-(3-fluoro-phenyl)-methyl]-amide LC-MS (m/z) 466.3 (MH$^+$, $^{81}$Br); $t_R$=1.73 (method C).

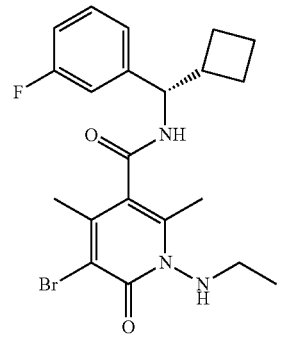

2c 5-Bromo-1-ethylamino-2,4-dimethyl-6-oxo-1,6-dihydro-pyridine-3-carboxylic acid [(S)-cyclobutyl-(3-fluoro-phenyl)-methyl]-amide LC-MS (m/z) 450.2 (MH$^+$, $^{79}$Br); $t_R$=1.64 (method C).

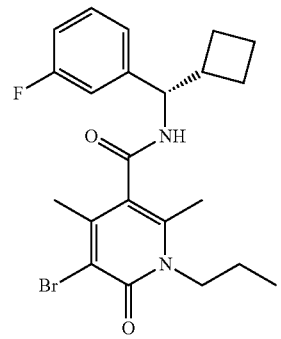

2d 5-Bromo-2,4-dimethyl-6-oxo-1-propyl-1,6-dihydro-pyridine-3-carboxylic acid [(S)-cyclobutyl-(3-fluoro-phenyl)-methyl]-amide The title compound was purified by preparative LC-MS. LC-MS (m/z) 449.3 (MH+, $^{79}$Br); $t_R$=1.6.

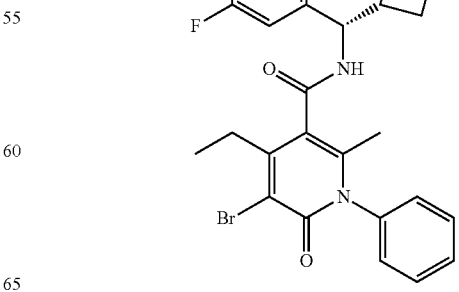

2e 5-Bromo-4-ethyl-2-methyl-6-oxo-1-phenyl-1,6-dihydro-pyridine-3-carboxylic acid [(S)-cyclobutyl-(3-fluoro-phenyl)-methyl]-amide The title compound was separated by extraction from the reaction mixture after aqueous work-up with ethyl acetate. LC-MS (m/z) 497.4 & 499.5 (MH+); $t_R$=1.7 (method C).

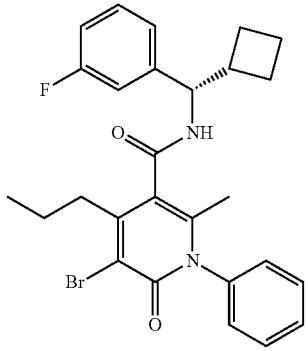

2f 5-Bromo-2-methyl-6-oxo-1-phenyl-4-propyl-1,6-dihydro-pyridine-3-carboxylic acid [(S)-cyclobutyl-(3-fluoro-phenyl)-methyl]-amide The title compound was separated by extraction from the reaction mixture after aqueous work-up with ethyl acetate. LC-MS (m/z) 511.3 & 513.6 (MH+); $t_R$=1.77 (method C).

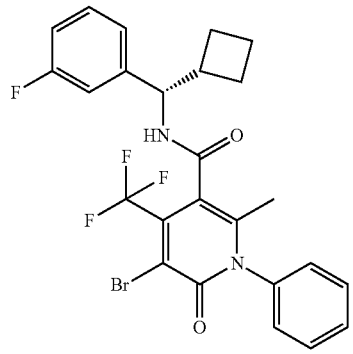

2g 5-Bromo-2-methyl-6-oxo-1-phenyl-4-trifluoromethyl-1,6-dihydro-pyridine-3-carboxylic acid [(S)-cyclobutyl-(3-fluoro-phenyl)-methyl]-amide The reaction mixture was stirred overnight at r.t. and the product was purified by flash chromatography. LC-MS (m/z) 539.3 (MH+, $^{81}$Br); $t_R$=1.70 (method C).

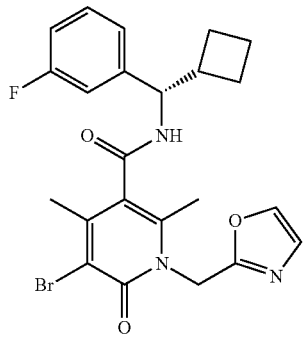

2h 5-Bromo-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide The reaction mixture was stirred overnight at r.t. and the product was purified by flash chromatography. LC-MS (m/z) 488.4 (MH+, $^{79}$Br); $t_R$=1.51 (method C).

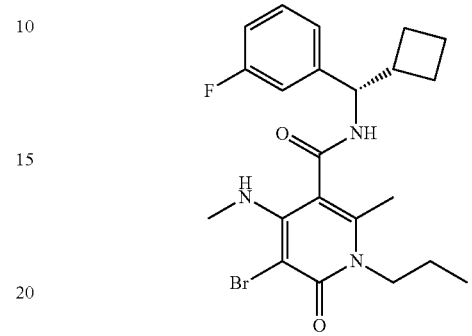

2i 5-Bromo-2-methyl-4-methylamino-6-oxo-1-propyl-1,6-dihydro-pyridine-3-carboxylic acid [(S)-cyclobutyl-(3-fluoro-phenyl)-methyl]-amide The title compound was purified by preparative LC-MS. LC-MS (m/z) 464.4 & 466.3 (MH+); $t_R$=1.72 (method C).

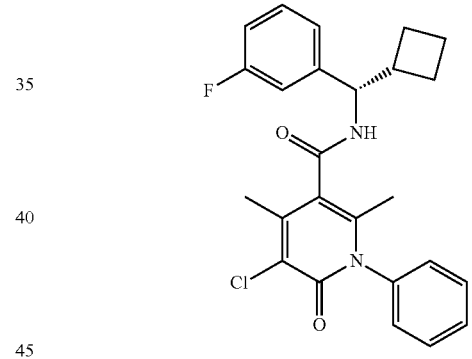

2j 5-Chloro-2,4-dimethyl-6-oxo-1-phenyl-1,6-dihydro-pyridine-3-carboxylic acid [(S)-cyclobutyl-(3-fluoro-phenyl)-methyl]-amide A mixture of 2,4-dimethyl-6-oxo-1-phenyl-1,6-dihydro-pyridine-3-carboxylic acid [(S)-cyclobutyl-(3-fluoro-phenyl)-methyl]-amide (13.9 mg, 0.0343 mmol) and N-chlorosuccinimide (5.33 mg, 0.0399 mmol) in N,N-dimethylformamide (0.3 mL, 4 mmol) was stirred at r.t. for 30 min. It was quenched and stirred with water (4 ml) for 5 min, then filtered, washed with water and dried in vacuo to give 10.1 mg of the title compound as a colourless solid, yield 67%. LC-MS (m/z) 439.4 & 441.6 (3:1, MH+); $t_R$=1.52 (method C). $^1$H NMR (T=+70° C., 500 MHz, DMSO-$d_6$, DMSO-$d_5$=2.50 ppm): 1.77 (overlapping s, 3H, Me), 1.70-1.92 (overlapping m, 5H), 2.07 (br. m, 1H), 2.17 (s, 3H, Me), 2.67 (m, 1H, CH of Cb), 4.94 (t, J=8.3 Hz, CH—N), 7.03 (br. t, 1H), 7.14 (br. d, J=9.8 Hz, 1H), 7.18 (br. d, J=7.7 Hz, 1H), 7.22 (br., 2H, Ph), 7.35 (br. m, 1H), 7.5 (br. t, 1H, para-H of Ph), 7.55 (br. m, 2H, two meta-H of Ph), 8.68 (br. d, 1H, NH).

The following compounds were prepared analogously:

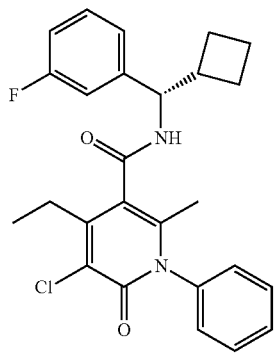

2k 5-Chloro-4-ethyl-2-methyl-6-oxo-1-phenyl-1,6-dihydro-pyridine-3-carboxylic acid [(S)-cyclobutyl-(3-fluoro-phenyl)-methyl]-amide

The title compound was separated from the reaction mixture after aqueous work-up with ethyl acetate and purified by preparative LC-MS. LC-MS (m/z) 453.3 & 455.5 (3:1, MH+); $t_R$=1.69.

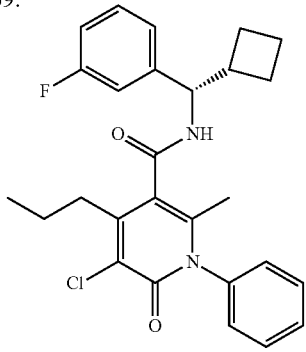

2l 5-Chloro-2-methyl-6-oxo-1-phenyl-4-propyl-1,6-dihydro-pyridine-3-carboxylic acid [(S)-cyclobutyl-(3-fluoro-phenyl)-methyl]-amide

The title compound was separated by extraction from the reaction mixture after aqueous work-up with ethyl acetate and purified by preparative LC-MS. LC-MS (m/z) 467.5 & 469.6 (3:1, MH+); $t_R$=1.77.

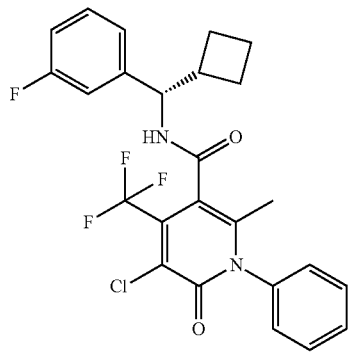

2m 5-Chloro-2-methyl-6-oxo-1-phenyl-4-trifluoromethyl-1,6-dihydro-pyridine-3-carboxylic acid [(S)-cyclobutyl-(3-fluoro-phenyl)-methyl]-amide

The reaction mixture was stirred overnight at r.t. and the product was purified by flash chromatography. LC-MS (m/z) 493.3 (MH+, $^{35}$Cl); $t_R$=1.69 (method C).

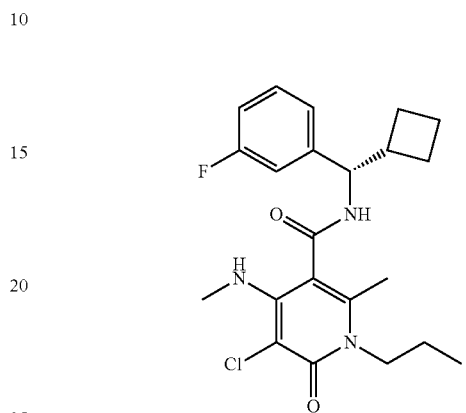

2n 5-Chloro-2-methyl-4-methylamino-6-oxo-1-propyl-1,6-dihydro-pyridine-3-carboxylic acid [(S)-cyclobutyl-(3-fluoro-phenyl)-methyl]-amide

The title compound was purified by preparative LC-MS. LC-MS (m/z) 420.6 (MH+); $t_R$=1.70 (method C).

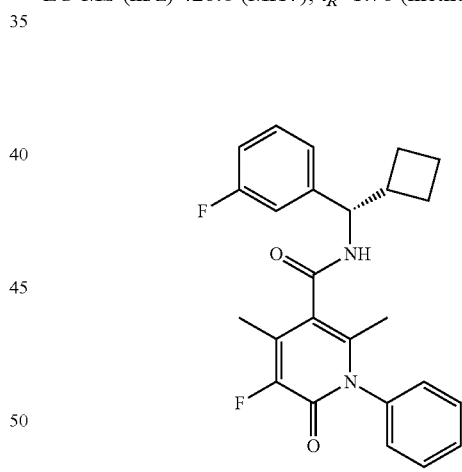

2o 5-Fluoro-2,4-dimethyl-6-oxo-1-phenyl-1,6-dihydro-pyridine-3-carboxylic acid [(S)-cyclobutyl-(3-fluoro-phenyl)-methyl]-amide

A suspension of 2,4-dimethyl-6-oxo-1-phenyl-1,6-dihydro-pyridine-3-carboxylic acid [(S)-cyclobutyl-(3-fluoro-phenyl)-methyl]-amide (9.91 mg, 0.0245 mmol and select-fluor (10.0 mg, 0.0282 mmol) in acetonitrile (0.1 mL) was sonicated for 3 hrs at 40° C. then allowed to stand for 3 days. It was quenched with water (3 ml) and extracted with ethyl acetate (3×1 mL). The combined organic solution was transferred to a preparative TLC plate (SiO$_2$, 0.25 mm×20 cm×20 cm) and eluted with ethyl acetate to give the crude title product (4 mg, 19% yield). LC-MS (m/z) 423.2 (MH+); $t_R$=1.44.

Example 3

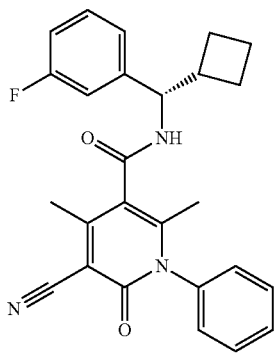

3a 5-Cyano-2,4-dimethyl-6-oxo-1-phenyl-1,6-dihydro-pyridine-3-carboxylic acid [(S)-cyclobutyl-(3-fluoro-phenyl)-methyl]-amide A mixture of 5-bromo-2,4-dimethyl-6-oxo-1-phenyl-1,6-dihydro-pyridine-3-carboxylic acid [(S)-cyclobutyl-(3-fluoro-phenyl)-methyl]-amide (2a, 12.7 mg, 0.0263 mmol), copper cyanide (20.0 mg, 0.223 mmol) and N-methylpyrrolidinone (0.200 mL) was heated at 220° C. under microwave irradiation for 20 min. It was partitioned between water (2 mL) and ethyl acetate (3×2 mL). The combined organic solution was filtered through a plug of silica gel (2 g), eluted with ethyl acetate and concentrated in vacuo (<1 mbar, 70° C., 60 min) to give 15 mg of a residue. It was transferred into a 5 g silica gel column with 1,2-dichloroethane and purified by flash chromatography with gradient heptane-ethylacetate to give the title compound as a white solid (8.7 mg, yield 77%). LC-MS (m/z) 430.3 (MH$^+$); $t_R$=1.45 (method A); $t_R$=0.77 (method B).

The following compounds were prepared analogously:

3b 5-Cyano-2,4-dimethyl-6-oxo-1-propylamino-1,6-dihydro-pyridine-3-carboxylic acid [(S)-cyclobutyl-(3-fluoro-phenyl)-methyl]-amide LC-MS (m/z) 430.3 (MH+); $t_R$=1.45 (method A); $t_R$=0.77 (method B).

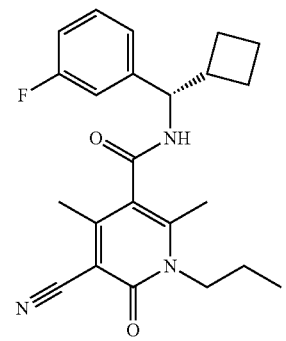

3c 5-Cyano-2,4-dimethyl-6-oxo-1-propyl-1,6-dihydro-pyridine-3-carboxylic acid [(S)-cyclobutyl-(3-fluoro-phenyl)-methyl]-amide LC-MS (m/z) 396.4 (MH+); $t_R$=1.47 (method C).

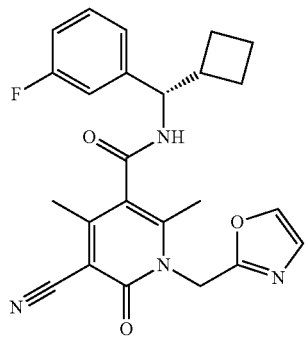

3d 5-Cyano-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide LC-MS (m/z) 434. (MH+); $t_R$=0.7 (method B).

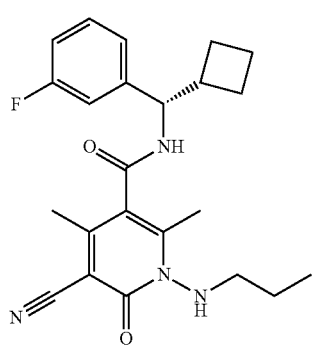

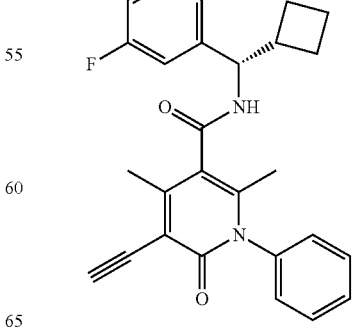

3e 5-Ethynyl-2,4-dimethyl-6-oxo-1-phenyl-1,6-dihydro-pyridine-3-carboxylic acid [(S)-cyclobutyl-(3-fluoro-phenyl)-methyl]-amide The title compound was made according to a general procedure for Sonogashira coupling described by M. Erdlyi and A. Gogoll, *J. Org. Chem.*, 2001, 66 (12), 4165-4169 "Rapid Homogeneous-Phase Sonogashira Coupling Reactions Using Controlled Microwave Heating" (method C).

Step 1: A mixture of 5-bromo-2,4-dimethyl-6-oxo-1-phenyl-1,6-dihydro-pyridine-3-carboxylic acid [(S)-cyclobutyl-(3-fluoro-phenyl)-methyl]-amide (2a, 60.0 mg, 0.124 mmol), N,N-dimethylformamide (0.6 mL), copper(I) iodide (4.5 mg, 0.024 mmol), bis(triphenylphosphine)palladium(II) chloride (9.1 mg, 0.013 mmol), triphenylphosphine (20.0 mg, 0.0762 mmol), N-ethylethanamine (0.6 mL, 6 mmol) and (trimethylsilyl)acetylene (0.052.6 mL, 0.372 mmol) was flushed with Argon and heated under microwave irradiation for 30 min at 120° C. It was evaporated in vacuo, transferred to 20 g silica gel column with 1,2-dichloroethane and separated by flash chromatography with gradient heptane-ethyl acetate to give 2,4-dimethyl-6-oxo-1-phenyl-5-trimethylsilanylethynyl-1,6-dihydro-pyridine-3-carboxylic acid [(S)-cyclobutyl-(3-fluoro-phenyl)-methyl]-amide (33 mg; yield=53%) as a pale yellow-brown solid. LC-MS (m/z) 501.7 (MH$^+$); $t_R$=1.94 (method C).

Step 2: A solution of the obtained compound (24.0 mg, 0.0479 mmol) from step 1 in methanol (2 mL) was stirred at r.t. in the presence of potassium carbonate (50 mg, 0.4 mmol) under argon overnight. It was poured into water (6 mL) and the yellow precipitate was filtered off to give the title compound (17 mg; yield=83%). LC-MS (m/z) 429.2 (MH$^+$); $t_R$=1.58 (method C). $^1$H NMR (T=+70° C., 500 MHz, DMSO-d$_6$, DMSO-d$_5$=2.50 ppm): 1.78 (overlapping s, 3H, Me), 1.72-1.92 (overlapping m, 5H), 2.06 (br. m, 1H), 2.17 (s, 3H, Me), 2.67 (m, 1H, CH of Cb), 4.24 (s, 1H, HC≡C), 4.94 (t, J=9 Hz, CH—N), 7.02 (br. t, 1H), 7.13 (br. d, J=10 Hz, 1H), 7.15-7.24 (br. m, 3H), 7.35 (br. q, 1H), 7.48 (br. t, 1H, para-H of Ph), 7.55 (br. m, 2H, two meta-H of Ph), 8.64 (br. d, J=8.4 Hz, 1H, NH).

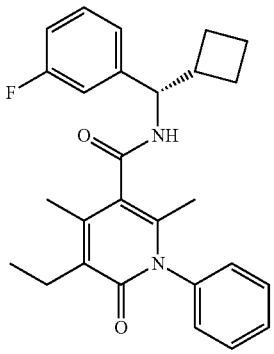

3f 5-Ethyl-2,4-dimethyl-6-oxo-1-phenyl-1,6-dihydro-pyridine-3-carboxylic acid [(S)-cyclobutyl-(3-fluoro-phenyl)-methyl]-amide To a solution of 5-ethynyl-2,4-dimethyl-6-oxo-1-phenyl-1,6-dihydro-pyridine-3-carboxylic acid [(S)-cyclobutyl-(3-fluoro-phenyl)-methyl]-amide (12.6 mg, 0.0294 mmol) in methanol (2 mL) 10% palladium on charcoal (9.1 mg) was added, It was degassed in vacuo and filled with hydrogen for 3 times then stirred vigorously for 90 min. It was evaporated, sonicated with ethyl acetate, filtered through a 2 g plug of silica gel, eluted with ethyl acetate and evaporated to give the title compound as a pale yellow solid residue (11.3 mg, yield=89%). LC-MS (m/z) 433.6 (MH$^+$); $t_R$=1.67 (method C). $^1$H NMR (T=+70° C., 500 MHz, DMSO-d$_6$, DMSO-d$_5$=2.50 ppm): 1.02 (t, J=7.3 Hz, 3H, Me of Et), 1.72 (overlapping s, 3H, Me), 1.74-1.85 (overlapping m, 4H), 1.89 (overlapping m, 1H), 2.04 (overlapping s, 3H, Me), 2.06 (overlapping br. m, 1H), 2.52 (overlapping with DMSO-d$_5$ m, 2H, CH$_2$ of Et), 2.68 (m, 1H, CH of Cb), 4.94 (t (unresolved dd), J=9.0; 9.5 Hz, CH—N), 7.01 (dt, J(d)=2 Hz, J(t)=8 Hz, 1H), 7.11-7.20 (m, 4H), 7.34 (q (unresolved dt), J(d)=6.3 Hz, J(t)=7.8 Hz, 1H), 7.45 (t, J=7.4 Hz, 1H, para-H of Ph), 7.52 (br. t, 2H, two meta-H of Ph), 8.60 (br. d, J=8.3 Hz, 1H, NH).

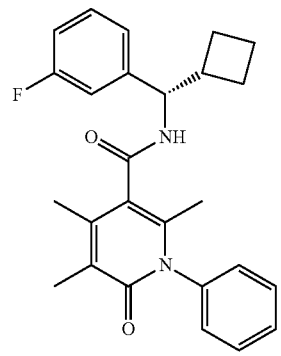

3g 2,4,5-Trimethyl-6-oxo-1-phenyl-1,6-dihydro-pyridine-3-carboxylic acid [(S)-cyclobutyl-(3-fluoro-phenyl)-methyl]-amide A mixture of 5-bromo-2,4-dimethyl-6-oxo-1-phenyl-1,6-dihydro-pyridine-3-carboxylic acid (S)-cyclobutyl-(3-fluoro-phenyl)-methyl]-amide (2a, 20.0 mg, 0.0414 mmol) 07), hexamethylphosphoramide (0.500 mL, 2.87 mmol), tetramethyltin (22.8 uL, 0.166 mmol) and benzylbis(triphenylphosphine)palladium(II) chloride (1.44 mg, 0.00190 mmol) was heated at 140° C. under microwave irradiation for 90 min. It was partitioned between water (2 mL) and ethyl acetate (3×2 mL). The combined organic solution was washed with brine (1 mL), dried (MgSO$_4$) and evaporated. The title compound (5.3 mg, yield 31%) was separated by flash chromatography on silica gel. LC-MS (m/z) 419.8 (MH$^+$); $t_R$=1.59 (method C.). $^1$H NMR (T=+70° C., 500 MHz, DMSO-d$_6$, DMSO-d$_5$=2.50 ppm): 1.72 (overlapping s, 3H, Me), 1.78 (overlapping s, 3H, Me), 1.74-1.84 (overlapping m, 4H), 1.88 (overlapping m, 1H), 1.99 (overlapping s, 3H, Me), 2.06 (overlapping br. m, 1H), 2.66 (m, 1H, CH of Cb), 4.93 (t, J=9.2 Hz, CH—N), 7.01 (dt, J(d)=2 Hz, J(t)=8.5 Hz, 1H), 7.11-7.20 (m, 4H), 7.34 (q (unresolved dt), J(d)=6.5 Hz, J(t)=7.7 Hz, 1H), 7.45 (t, J=7.4 Hz, 1H, para-H of Ph), 7.52 (br. t, 2H, two meta-H of Ph), 8.60 (br. d, J=8.3 Hz, 1H, NH).

TABLE 3

Reagents used for the preparation of the compounds.

| Name | Supplier | CAS no. | Cat. no. |
|---|---|---|---|
| Ethyl isodehydroacetate | Sigma-Aldrich | 3385-34-0 | E33408 |
| Methyl isodehydroacetate | Acros | 41264-06-6 | 18381-0500 |
| Isodehydroacetic acid | Fisher | 480-65-9 | 351520050 |
| Hydrazine monohydrochloride hydrazine hydrate | Sigma-Aldrich | 2644-70-4 | 216194 |
| Oxazol-2-ylmethylamine hydrochloride | JW Pharmlab | 907544-38-1 | 56-0002 |
| 1-Ethyl-3-(3-dimethylaminopropyl)carbodiimide hydrochloride (EDC) | Aldrich | 25952-53-8 | 16,146-2 |
| 1-Hydroxybenzotriazole (HOBT) | ABCR | 2592-95-2 | AV21700 |
| HATU (=2-(7-aza-1H-benzotriazole-1-yl)-1,1,3,3-tetramethyluronium hexafluorophosphate) | Sigma-Aldrich | 148893-10-1 | 11373 |
| N-bromosuccinimide | Aldrich | 128-08-5 | B8,125-5 |
| N-Chromosuccinimide | Aldrich | 128-09-6 | 10,968-1 |
| Selectfluor (=N-Fluoro-N'-(chloromethyl)triethylenediamine bis(tetrafluoroborate)) | Aldrich | 140681-55-6 | 439479 |
| Hexamethylphosphoramide | Sigma-Aldrich | 680-31-9 | H11602 |
| Tetramethyltin | Sigma-Aldrich | 594-27-4 | 481394 |
| Benzylbis(triphenylphosphine)palladium (II) chloride | Sigma-Aldrich | 22784-59-4 | 277665 |
| Ethyl 3-anilinobut-2-enoate | ABCR | 6287-35-0 | AB133469 |
| Ethyl 2-pentynoate | Sigma-Aldrich | 55314-57-3 | 632112 |
| Ethyl-2-hexynoate | ABCR | 16205-90-6 | AB177994 |
| Ethyl 4,4,4-trifluoro-2-butynoate | Sigma-Aldrich | 79424-03-6 | 401455 |
| Phosphoryl chloride | | | |
| Ethyl malonyl chloride | | | |
| (S)-(−)-1-Phenylpropylamine | Lancaster | 3789-59-1 | 16320 |
| Sodium hydride | Aldrich | 7646-69-7 | 45,291-2 |
| C-((S)-C-Cyclopropyl-C-phenyl)-methylamine | Acesys | | A5011S |

Example 4

NK3 Receptor Binding Assay

Membrane Preparation:

BHK cells stably expressing the human NK3 receptor were seeded in harvesting plates in Dulbeccos MEM containing GlutaMax (862 mg/l), 1 mM sodium pyruvate, 10% fetal calf serum, 1% Pen/Strep, 1 mg/ml G418 and were grown at 34° C. in a humidified atmosphere containing 10% $CO_2$. To increase receptor expression, 10 μM trichotatin A was added to the media 24 hours before harvest of the cells at a confluency of app 90%. Prior to the harvesting, the cells were washed twice with PBS without $Mg^{2+}$ of $Ca^{2+}$ and subsequently scrapped of in 10 ml PBS pr harvesting plate. The cells suspension were centrifuged at 1500×G in three minutes before resuspension in 15 mM Tris-HCl buffer pH 7.5 containing 2 mM $MgCl_2$; 0.3 mM EDTA and 1 mM EGTA (buffer A). The cell suspension was homogenised and subsequently centrifuged at 40000×G in 30 minutes. The membrane-pellet was resuspended in buffer A containing 250 mM sucrose, aliquoted and stored at −80° C.

Affinity Assay Description:

The assay is performed as a filter-based competition-binding in a 50 mM Tris pH 7.4 assay buffer containing 120 mM NaCl and 3 mM $MnCl_2$. App 0.05 nM $^3$H-AE93103 was mixed with test compounds before addition of 0.15 μg of a homogenised NK3 membrane preparation in a total volume of 300 μl. The assay plate is incubated for 90 min at RT before content of the wells is transferred using a cell-harvester to GF/C filter plates, which has been pretreated with 0.1% PEI.

The filter is washed 3 times with 1 ml an ice-cold 50 mM Tris buffer, pH 7.4. The filter is dried and added scintillation liquid before the plate is counted in a topcounter 5 minutes pr well.

The total binding, which comprised less than 10% of added radioligand, was defined using assay buffer whereas the non-specific binding was defined in the presence of 1 μM SR142801. The non-specific binding constituted ~10% of the total binding.

Data points are expressed in percent of the specific binding of $^3$H-AE93103 and the 1050 values (concentration causing 50% inhibition of $^3$H-AE93103 specific binding) are determined by non-linear regression analysis using a sigmoidal variable slope curve fitting. The dissociation constant ($K_i$) were calculated from the Cheng Prusoff equation ($K_i=IC_{50}/(1+(L/K_d))$), where the concentration of free radioligand L is approximated to the concentration of added $^3$H-AE93103 in the assay (~0.05 nM) and Kd equals the affinity of the $^3$H-AE93103 for the NK3 receptor. The Kd of $^3$H-AE93103 was determined to be 0.072 nM from four independent saturation assays each performed with duplicate determinations. Bmax was ~15 μmol/mg.

The compounds of the present invention generally have $K_i$ values of 1000 nM or less, such as 500 nM. Many compounds, in fact, have $K_i$ values below 100 nM.

Example 5

NK3 Receptor Efficacy and Potency Assay

BHK cells stably expressing the human NK3 receptor were seeded in 100 μl media in black walled clear-base 96-wells plates (Costar) aiming at a confluency of 95-100% at the day of assay. The assay was performed according to the Calcium 4 Assay kit (Molecular Devices). At the day of the assay, the media was removed and the cells were washed once with the HBSS buffer (Hanks BSS buffer, pH 7.4 containing 20 mM Hepes) before 100 μl of a solution of the calcium assay reagent dissolved in the HBSS buffer containing 2.5 mM probinicid was added to the cells. The plates were incubated for 60 min at 34° C., 10% $CO_2$ before use in the FDSS 7000 for examination of fluorescence.

One representative plate was examined with a dose-response curve with NKB in a setup in which the wells initially were added HBSS buffer and 15 min later the various concentrations of NKB were added in order to determine the $EC_{50}$ and $EC_{85}$ of NKB. All compound plates used for NKB were precoated with a 1% BSA solution and subsequently washed three times with $H_2O$, NKB was diluted in HBSS buffer containing 0.1% BSA.

For efficacy and potency evaluation of compounds, these were diluted in HBSS buffer prior to test. For test of agonist activity, 25 μl of the diluted compound solution was added and the plate was analyzed for 5 minutes in the FDSS 7000. For test of antagonist activity, the plate was incubated for another 45 minutes before addition of 25 μl of the $EC_{85}$ concentration of NKB (app. 2 nM) as described above. The plates were subsequently analyzed for 5 minutes before the assay was terminated. The maximal increase in fluorescence over background following each ligand addition was determined. The $IC_{50}$ value was calculated using sigmoidal variable slope curve fitting, and the $cIC_{50}$ value was determined using the equation $(cIC_{50}=IC_{50}/(1+(EC_{85}/EC_{50})))$, where $EC_{85}$ and $EC_{50}$ for NKB were determined as described above.

All pyridones of the present invention characterized in the NK3 receptor efficacy and potency assay have been antagonists without any observed significant agonist activity at relevant doses. The table shows affinity data (obtained as described in Example 4) and potency data obtained with compounds of the invention.

| Example | Affinity (Ki/nM) | Potency (cIC50/nM) |
|---------|------------------|--------------------|
| 1ak | 49 | 150 |
| 1i | 16 | 69 |
| 1s | 67 | 360 |
| 1z | 36 | 180 |
| 2a | 52 | 79 |
| 2c | 24 | 35 |
| 2d | 30 | 120 |
| 2e | 50 | 240 |
| 2f | 90 | 270 |
| 2g | 7 | 70 |
| 2m | 24 | 78 |
| 3b | 22 | 39 |
| 3d | 34 | 52 |
| 3e | 240 | 620 |

The invention claimed is:

1. A compound according to formula I

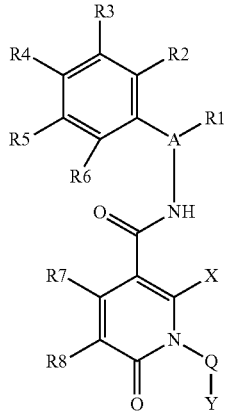

wherein A is N, CH or $CR^1$;
each $R^1$ is independently $C_{1-6}$alkyl, $C_{2-6}$alkenyl, or $C_{2-6}$alkynyl;
X is $C_{1-6}$alkyl;
Q is a bond, —$CH_2$— or —NH—;
Y is $C_{1-6}$ alkyl, or Y is heteroaryl with 5 ring atoms, wherein 1, 2 or 3 ring atoms are selected from the group consisting of O, N and S, or Y is phenyl provided that Q is not —$CH_2$—, wherein said heteroaryl or phenyl may be substituted with one or more substituents selected from the group consisting of halogen, $C_{1-6}$alkyl, $C_{2-6}$alkenyl and $C_{2-6}$alkynyl;
each of $R^2$-$R^6$ are independently hydrogen, $C_{1-6}$alkyl, $C_{2-6}$alkenyl, $C_{2-6}$alkynyl or halogen;
each of $R^7$-$R^8$ are independently $C_{1-6}$alkyl, $C_{2-6}$alkenyl, $C_{2-6}$alkynyl, halogen, cyano, or amine, wherein said $C_{1-6}$alkyl, $C_{2-6}$alkenyl or $C_{2-6}$alkynyl is optionally substituted with one or more halogen;
or a pharmaceutically acceptable salt thereof.

2. The compound according to claim 1, wherein A is CH.

3. The compound according to claim 1, wherein $R^1$ is $C_{1-6}$alkyl.

4. The compound according to claim 3, wherein $R^1$ is ethyl, 2-propyl, cyclopropyl, cyclobutyl, cyclopentyl or cyclohexyl.

5. The compound according to claim 1, wherein X is methyl.

6. The compound according to claim 1, wherein Y is $C_{1-6}$alkyl, phenyl or oxazole.

7. The compound according to claim 6, wherein Q is a bond and Y is $C_{1-4}$alkyl or phenyl.

8. The compound according to claim 6, wherein Q is —NH— and Y is $C_{1-4}$alkyl.

9. The compound according to claim 1, wherein each of $R^2$-$R^6$ are independently hydrogen or halogen.

10. The compound according to claim 9, wherein all of $R^2$-$R^6$ are hydrogen.

11. The compound according to claim 9, wherein one or two of $R^2$-$R^6$ are halogen.

12. The compound according to claim 1, wherein $R^7$ is $C_{1-4}$alkyl or amine, wherein said $C_{1-4}$alkyl is optionally substituted with one or more halogen.

13. The compound according to claim 1, wherein $R^8$ is halogen, cyano or ethynyl.

14. The compound according to claim 1, wherein $R^7$ is $C_{1-4}$alkyl and $R^8$ is halogen.

15. The compound according to claim 1 according to formula I'

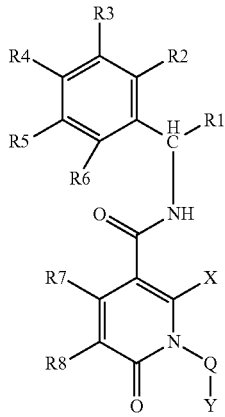

[I']

wherein each $R^1$ is independently $C_{1-6}$alkyl, $C_{2-6}$alkenyl, or $C_{2-6}$alkynyl;
X is $C_{1-6}$alkyl;
Q is a bond or —NH;
Y is phenyl or $C_{1-6}$ alkyl;
one or two of $R^2$-$R^6$ are halogen;
$R^7$ is $C_{1-4}$alkyl;
$R^8$ is halogen, cyano or ethynyl;
or a pharmaceutically acceptable salt thereof.

16. The compound according to claim 1 selected from the group consisting of:

5-Chloro-2,4-dimethyl-6-oxo-1-propylamino-1,6-dihydro-pyridine-3-carboxylic acid [(S)-cyclobutyl-(3-fluoro-phenyl)-methyl]-amide;
5-Bromo-2,4-dimethyl-6-oxo-1-propylamino-1,6-dihydro-pyridine-3-carboxylic acid [(S)-cyclopropyl-(4-fluoro-phenyl)-methyl]-amide;
5-Bromo-2,4-dimethyl-6-oxo-1-propylamino-1,6-dihydro-pyridine-3-carboxylic acid [(S)-(3-chloro-phenyl)-cyclopropyl-methyl]-amide;
5-Bromo-2,4-dimethyl-6-oxo-1-propylamino-1,6-dihydro-pyridine-3-carboxylic acid [(S)-(4-chloro-phenyl)-cyclopropyl-methyl]-amide;
5-Bromo-2,4-dimethyl-6-oxo-1-propylamino-1,6-dihydro-pyridine-3-carboxylic acid [(S)-1-(2-fluoro-phenyl)-propyl]-amide;
5-Bromo-2,4-dimethyl-6-oxo-1-propylamino-1,6-dihydro-pyridine-3-carboxylic acid [(S)-1-(3-fluoro-phenyl)-propyl]-amide;
5-Bromo-2,4-dimethyl-6-oxo-1-propylamino-1,6-dihydro-pyridine-3-carboxylic acid [(S)-1-(4-fluoro-phenyl)-propyl]-amide;
5-Bromo-2,4-dimethyl-6-oxo-1-propylamino-1,6-dihydro-pyridine-3-carboxylic acid ((S)-2-methyl-1-phenyl-propyl)-amide;
5-Bromo-2,4-dimethyl-6-oxo-1-propylamino-1,6-dihydro-pyridine-3-carboxylic acid ((S)-cyclobutyl-phenyl-methyl)-amide;
5-Bromo-2,4-dimethyl-6-oxo-1-propylamino-1,6-dihydro-pyridine-3-carboxylic acid ((S)-cyclopentyl-phenyl-methyl)-amide;
5-Bromo-2,4-dimethyl-6-oxo-1-propylamino-1,6-dihydro-pyridine-3-carboxylic acid [(S)-cyclobutyl-(4-fluoro-phenyl)-methyl]-amide;
5-Bromo-2,4-dimethyl-6-oxo-1-propylamino-1,6-dihydro-pyridine-3-carboxylic acid [(S)-cyclopropyl-(3-fluoro-phenyl)-methyl]-amide;
5-Bromo-2,4-dimethyl-6-oxo-1-propylamino-1,6-dihydro-pyridine-3-carboxylic acid ((S)-cyclopropyl-phenyl-methyl)-amide;
5-Bromo-2,4-dimethyl-6-oxo-1-propylamino-1,6-dihydro-pyridine-3-carboxylic acid [(S)-1-(4-chloro-phenyl)-propyl]-amide;
5-Bromo-2,4-dimethyl-6-oxo-1-propylamino-1,6-dihydro-pyridine-3-carboxylic acid [(S)-1-(3-chloro-phenyl)-propyl]-amide;
5-Bromo-2,4-dimethyl-6-oxo-1-propylamino-1,6-dihydro-pyridine-3-carboxylic acid ((S)-cyclohexyl-phenyl-methyl)-amide;
5-Bromo-2,4-dimethyl-6-oxo-1-propylamino-1,6-dihydro-pyridine-3-carboxylic acid ((S)-1-phenyl-propyl)-amide;
5-Bromo-2,4-dimethyl-6-oxo-1-propyl-1,6-dihydro-pyridine-3-carboxylic acid [(S)-cyclopropyl-(4-fluoro-phenyl)-methyl]-amide;
5-Bromo-2,4-dimethyl-6-oxo-1-propyl-1,6-dihydro-pyridine-3-carboxylic acid [(S)-(2-chloro-phenyl)-cyclopropyl-methyl]-amide;
5-Bromo-2,4-dimethyl-6-oxo-1-propyl-1,6-dihydro-pyridine-3-carboxylic acid [(S)-(3-chloro-phenyl)-cyclopropyl-methyl]-amide;
5-Bromo-2,4-dimethyl-6-oxo-1-propyl-1,6-dihydro-pyridine-3-carboxylic acid [(S)-(4-chloro-phenyl)-cyclopropyl-methyl]-amide;
5-Bromo-2,4-dimethyl-6-oxo-1-propyl-1,6-dihydro-pyridine-3-carboxylic acid [(S)-1-(2-fluoro-phenyl)-propyl]-amide;
5-Bromo-2,4-dimethyl-6-oxo-1-propyl-1,6-dihydro-pyridine-3-carboxylic acid [(S)-1-(3-fluoro-phenyl)-propyl]-amide;
5-Bromo-2,4-dimethyl-6-oxo-1-propyl-1,6-dihydro-pyridine-3-carboxylic acid [(S)-1-(4-fluoro-phenyl)-propyl]-amide;
5-Bromo-2,4-dimethyl-6-oxo-1-propyl-1,6-dihydro-pyridine-3-carboxylic acid ((S)-2-methyl-1-phenyl-propyl)-amide;
5-Bromo-2,4-dimethyl-6-oxo-1-propyl-1,6-dihydro-pyridine-3-carboxylic acid ((S)-cyclobutyl-phenyl-methyl)-amide;
5-Bromo-2,4-dimethyl-6-oxo-1-propyl-1,6-dihydro-pyridine-3-carboxylic acid ((S)-cyclopentyl-phenyl-methyl)-amide;
5-Bromo-2,4-dimethyl-6-oxo-1-propyl-1,6-dihydro-pyridine-3-carboxylic acid [cyclobutyl-(2-fluoro-phenyl)-methyl]-amide;
5-Bromo-2,4-dimethyl-6-oxo-1-propyl-1,6-dihydro-pyridine-3-carboxylic acid [(S)-cyclobutyl-(4-fluoro-phenyl)-methyl]-amide;
5-Bromo-2,4-dimethyl-6-oxo-1-propyl-1,6-dihydro-pyridine-3-carboxylic acid [(S)-cyclopropyl-(3-fluoro-phenyl)-methyl]-amide;
5-Bromo-2,4-dimethyl-6-oxo-1-propyl-1,6-dihydro-pyridine-3-carboxylic acid ((S)-cyclopropyl-phenyl-methyl)-amide;
5-Bromo-2,4-dimethyl-6-oxo-1-propyl-1,6-dihydro-pyridine-3-carboxylic acid [(S)-1-(4-chloro-phenyl)-propyl]-amide;
5-Bromo-2,4-dimethyl-6-oxo-1-propyl-1,6-dihydro-pyridine-3-carboxylic acid [(S)-1-(3-chloro-phenyl)-propyl]-amide;

5-Bromo-2,4-dimethyl-6-oxo-1-propyl-1,6-dihydro-pyridine-3-carboxylic acid ((S)-1-phenyl-propyl)-amide;

5-Bromo-2,4-dimethyl-6-oxo-1-propyl-1,6-dihydro-pyridine-3-carboxylic acid [(S)-cyclobutyl-(3,4-difluorophenyl)-methyl]-amide;

5-Bromo-2,4-dimethyl-6-oxo-1-propyl-1,6-dihydro-pyridine-3-carboxylic acid ((S)-cyclohexyl-phenyl-methyl)-amide;

5-Bromo-2,4-dimethyl-6-oxo-1-propyl-1,6-dihydro-pyridine-3-carboxylic acid [(S)-cyclobutyl-(3,5-difluorophenyl)-methyl]-amide;

5-Bromo-2,4-dimethyl-6-oxo-1-propyl-1,6-dihydro-pyridine-3-carboxylic acid [(S)-cyclopropyl-(3,4-difluorophenyl)-methyl]-amide;

5-Bromo-2,4-dimethyl-6-oxo-1-propyl-1,6-dihydro-pyridine-3-carboxylic acid [(R)-cyclopropyl-(3-fluoro-phenyl)-methyl]-amide;

4-Chloro-2-methyl-6-oxo-1-propyl-1,6-dihydro-pyridine-3-carboxylic acid [(S)-cyclobutyl-(3-fluoro-phenyl)-methyl]-amide;

5-Bromo-2,4-dimethyl-6-oxo-1-phenyl-1,6-dihydro-pyridine-3-carboxylic acid [(S)-cyclobutyl-(3-fluoro-phenyl)-methyl]-amide;

5-Bromo-2,4-dimethyl-6-oxo-1-propylamino-1,6-dihydro-pyridine-3-carboxylic acid [(S)-cyclobutyl-(3-fluoro-phenyl)-methyl]-amide;

5-Bromo-1-ethylamino-2,4-dimethyl-6-oxo-1,6-dihydro-pyridine-3-carboxylic acid [(S)-cyclobutyl-(3-fluoro-phenyl)-methyl]-amide;

5-Bromo-2,4-dimethyl-6-oxo-1-propyl-1,6-dihydro-pyridine-3-carboxylic acid [(S)-cyclobutyl-(3-fluoro-phenyl)-methyl]-amide;

5-Bromo-4-ethyl-2-methyl-6-oxo-1-phenyl-1,6-dihydro-pyridine-3-carboxylic acid [(S)-cyclobutyl-(3-fluoro-phenyl)-methyl]-amide;

5-Bromo-2-methyl-6-oxo-1-phenyl-4-propyl-1,6-dihydro-pyridine-3-carboxylic acid [(S)-cyclobutyl-(3-fluoro-phenyl)-methyl]-amide;

5-Bromo-2-methyl-6-oxo-1-phenyl-4-trifluoromethyl-1,6-dihydro-pyridine-3-carboxylic acid [(S)-cyclobutyl-(3-fluoro-phenyl)-methyl]-amide;

5-Bromo-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide;

5-Bromo-2-methyl-4-methylamino-6-oxo-1-propyl-1,6-dihydro-pyridine-3-carboxylic acid [(S)-cyclobutyl-(3-fluoro-phenyl)-methyl]-amide;

5-Chloro-2,4-dimethyl-6-oxo-1-phenyl-1,6-dihydro-pyridine-3-carboxylic acid [(S)-cyclobutyl-(3-fluoro-phenyl)-methyl]-amide;

5-Chloro-4-ethyl-2-methyl-6-oxo-1-phenyl-1,6-dihydro-pyridine-3-carboxylic acid [(S)-cyclobutyl-(3-fluoro-phenyl)-methyl]-amide;

5-Chloro-2-methyl-6-oxo-1-phenyl-4-propyl-1,6-dihydro-pyridine-3-carboxylic acid [(S)-cyclobutyl-(3-fluoro-phenyl)-methyl]-amide;

5-Chloro-2-methyl-6-oxo-1-phenyl-4-trifluoromethyl-1,6-dihydro-pyridine-3-carboxylic acid [(S)-cyclobutyl-(3-fluoro-phenyl)-methyl]-amide;

5-Chloro-2-methyl-4-methylamino-6-oxo-1-propyl-1,6-dihydro-pyridine-3-carboxylic acid [(S)-cyclobutyl-(3-fluoro-phenyl)-methyl]-amide;

5-Fluoro-2,4-dimethyl-6-oxo-1-phenyl-1,6-dihydro-pyridine-3-carboxylic acid [(S)-cyclobutyl-(3-fluoro-phenyl)-methyl]-amide;

5-Cyano-2,4-dimethyl-6-oxo-1-phenyl-1,6-dihydro-pyridine-3-carboxylic acid [(S)-cyclobutyl-(3-fluoro-phenyl)-methyl]-amide;

5-Cyano-2,4-dimethyl-6-oxo-1-propylamino-1,6-dihydro-pyridine-3-carboxylic acid [(S)-cyclobutyl-(3-fluoro-phenyl)-methyl]-amide;

5-Cyano-2,4-dimethyl-6-oxo-1-propyl-1,6-dihydro-pyridine-3-carboxylic acid [(S)-cyclobutyl-(3-fluoro-phenyl)-methyl]-amide;

5-Cyano-2,4-dimethyl-1-oxazol-2-ylmethyl-6-oxo-1,6-dihydro-pyridine-3-carboxylic acid [(S)-cyclobutyl-(3-fluoro-phenyl)-methyl]-amide;

5-Ethynyl-2,4-dimethyl-6-oxo-1-phenyl-1,6-dihydro-pyridine-3-carboxylic acid [(S)-cyclobutyl-(3-fluoro-phenyl)-methyl]-amide;

5-Ethyl-2,4-dimethyl-6-oxo-1-phenyl-1,6-dihydro-pyridine-3-carboxylic acid [(S)-cyclobutyl-(3-fluoro-phenyl)-methyl]-amide; and 2,4,5-Trimethyl-6-oxo-1-phenyl-1,6-dihydro-pyridine-3-carboxylic acid [(S)-cyclobutyl-(3-fluoro-phenyl)-methyl]-amide; or a pharmaceutically acceptable salt thereof.

17. A pharmaceutical composition comprising a compound according to claim 1, and one or more pharmaceutically acceptable carriers or excipients.

18. A pharmaceutical composition comprising a compound according to claim 16, and one or more pharmaceutically acceptable carriers or excipients.

19. A method for the treatment of schizophrenia comprising the administration to a patient in need thereof a therapeutically effective amount of a compound of formula I.

20. A method for the treatment of irritable bowel syndrome comprising the administration to a patient in need thereof a therapeutically effective amount of a compound of formula I.

* * * * *